US012697505B2

(12) United States Patent     (10) Patent No.: US 12,697,505 B2

Muller et al.     (45) Date of Patent: Aug. 4, 2026

(54) SYSTEMS AND METHODS FOR APPLYING AND MONITORING EYE THERAPY

(71) Applicant: Avedro, Inc., Waltham, MA (US)

(72) Inventors: David Muller, Boston, MA (US); John Marshall, Farmborough (GB); Marc D. Friedman, Needham, MA (US); Stephen Blinn, Amherst, NH (US); Ronald Scharf, Waltham, MA (US); Pavel Kamaev, Lexington, MA (US); Radha Pertaub, Watertown, MA (US)

(73) Assignee: Avedro, Inc., Burlington, MA (US)

( * ) Notice: Subject to any disclaimer, the term of this patent is extended or adjusted under 35 U.S.C. 154(b) by 325 days.

(21) Appl. No.: 17/123,089

(22) Filed: Dec. 15, 2020

(65) Prior Publication Data

US 2021/0101020 A1     Apr. 8, 2021

Related U.S. Application Data

(63) Continuation of application No. 13/051,699, filed on Mar. 18, 2011, now abandoned.

(Continued)

(51) Int. Cl.
    *A61F 9/008*     (2006.01)
    *A61B 3/10*     (2006.01)
    (Continued)

(52) U.S. Cl.
    CPC ............ *A61N 5/0625* (2013.01); *A61B 3/101* (2013.01); *A61B 3/107* (2013.01); *A61F 9/00* (2013.01);
    (Continued)

(58) Field of Classification Search
    CPC ......... A61F 9/0079; A61F 9/008; A61N 5/06; A61N 5/062
    See application file for complete search history.

(56) References Cited

U.S. PATENT DOCUMENTS

| | | | |
|---|---|---|---|
| 4,034,750 A | 7/1977 | Seiderman | |
| 4,665,913 A | 5/1987 | L'Esperance, Jr. | |

(Continued)

FOREIGN PATENT DOCUMENTS

| | | | |
|---|---|---|---|
| CN | 1474666 A | 2/2004 | |
| DE | 102008046834 | 3/2010 | |

(Continued)

OTHER PUBLICATIONS

Rocha K., et al., "Comparative Study of Riboflavin-UVA Cross-linking and "Flash-linking" Using Surface Wave Elastometry," Journal of Refractive Surgery, vol. 24 Issue 7, pp. S748-S751; Sep. 2008 (4 pages).

(Continued)

*Primary Examiner* — Lynsey C Eiseman
(74) *Attorney, Agent, or Firm* — K&L Gates

(57)     ABSTRACT

Devices and approaches for activating cross-linking within corneal tissue to stabilize and strengthen the corneal tissue following an eye therapy treatment. A feedback system is provided to acquire measurements and pass feedback information to a controller. The feedback system may include an interferometer system, a corneal polarimetry system, or other configurations for monitoring cross-linking activity within the cornea. The controller is adapted to analyze the feedback information and adjust treatment to the eye based on the information. Aspects of the feedback system may also be used to monitor and diagnose features of the eye. Methods of activating cross-linking according to information provided by a feedback system in order to improve accuracy and safety of a cross-linking therapy are also provided.

17 Claims, 27 Drawing Sheets

100

Related U.S. Application Data

(60) Provisional application No. 61/423,375, filed on Dec. 15, 2010, provisional application No. 61/409,103, filed on Nov. 1, 2010, provisional application No. 61/388,963, filed on Oct. 1, 2010, provisional application No. 61/377,024, filed on Aug. 25, 2010, provisional application No. 61/328,138, filed on Apr. 26, 2010, provisional application No. 61/326,527, filed on Apr. 21, 2010, provisional application No. 61/319,111, filed on Mar. 30, 2010, provisional application No. 61/315,840, filed on Mar. 19, 2010.

(51) Int. Cl.

| | |
|---|---|
| *A61B 3/107* | (2006.01) |
| *A61F 9/00* | (2006.01) |
| *A61N 5/06* | (2006.01) |
| *A61F 9/007* | (2006.01) |
| *A61N 5/067* | (2006.01) |

(52) U.S. Cl.
CPC .............. *A61F 9/008* (2013.01); *A61N 5/062* (2013.01); *A61F 9/0079* (2013.01); *A61F 2009/00844* (2013.01); *A61F 2009/00857* (2013.01); *A61F 2009/00872* (2013.01); *A61N 2005/0643* (2013.01); *A61N 2005/0661* (2013.01); *A61N 5/067* (2021.08)

(56) References Cited

U.S. PATENT DOCUMENTS

| | | | |
|---|---|---|---|
| 4,712,543 A | 12/1987 | Baron | |
| 4,764,007 A | 8/1988 | Task | |
| 4,891,043 A | 1/1990 | Zelmer et al. | |
| 4,969,912 A | 11/1990 | Kelman et al. | |
| 4,994,058 A | 2/1991 | Raven et al. | |
| 5,019,074 A | 5/1991 | Muller | |
| 5,171,318 A | 12/1992 | Gibson et al. | |
| 5,281,211 A | 1/1994 | Parel et al. | |
| 5,332,802 A | 7/1994 | Kelman et al. | |
| 5,461,212 A | 10/1995 | Seiler et al. | |
| 5,490,849 A | 2/1996 | Smith | |
| 5,512,966 A | 4/1996 | Snook | |
| 5,562,656 A | 10/1996 | Sumiya | |
| 5,624,437 A | 4/1997 | Freeman et al. | |
| 5,779,696 A | 7/1998 | Berry et al. | |
| 5,786,893 A | 7/1998 | Fink et al. | |
| 5,891,131 A | 4/1999 | Rajan et al. | |
| 5,910,110 A | 6/1999 | Bastable | |
| 6,030,376 A * | 2/2000 | Arashima ........... | A61F 9/00804 606/4 |
| 6,033,396 A | 3/2000 | Huang et al. | |
| 6,139,876 A | 10/2000 | Kolta | |
| 6,161,544 A | 12/2000 | DeVore et al. | |
| 6,188,500 B1 | 2/2001 | Rudeen et al. | |
| 6,210,401 B1 * | 4/2001 | Lai ...................... | B23K 26/032 606/4 |
| 6,218,360 B1 | 4/2001 | Cintron et al. | |
| 6,270,221 B1 | 8/2001 | Liang et al. | |
| 6,280,436 B1 | 8/2001 | Freeman et al. | |
| 6,293,938 B1 * | 9/2001 | Muller ................ | A61F 9/00817 606/5 |
| 6,319,273 B1 | 11/2001 | Chen et al. | |
| 6,322,557 B1 | 11/2001 | Nikolaevich et al. | |
| 6,325,792 B1 | 12/2001 | Swinger et al. | |
| 6,394,999 B1 | 5/2002 | Williams et al. | |
| 6,478,792 B1 | 11/2002 | Hansel | |
| 6,520,956 B1 | 2/2003 | Huang | |
| 6,520,958 B1 | 2/2003 | Shimmick et al. | |
| 6,537,545 B1 | 3/2003 | Karageozian et al. | |
| 6,571,118 B1 | 5/2003 | Utzinger et al. | |
| 6,617,963 B1 | 9/2003 | Watters et al. | |
| 6,946,440 B1 | 9/2005 | DeWoolfson et al. | |
| 7,001,374 B2 | 2/2006 | Peyman | |

| | | | |
|---|---|---|---|
| 7,004,902 B2 | 2/2006 | Luce | |
| 7,044,945 B2 | 5/2006 | Sand | |
| 7,073,510 B2 | 7/2006 | Redmond et al. | |
| 7,331,350 B2 | 2/2008 | Kochevar et al. | |
| 7,402,562 B2 | 7/2008 | DeWoolfson et al. | |
| 7,731,362 B2 | 6/2010 | Gerlach | |
| 7,753,943 B2 | 7/2010 | Strong | |
| 7,898,656 B2 | 3/2011 | Yun et al. | |
| 7,935,058 B2 | 5/2011 | Dupps et al. | |
| 8,111,394 B1 | 2/2012 | Borysow et al. | |
| 8,115,919 B2 | 2/2012 | Yun et al. | |
| 8,366,689 B2 | 2/2013 | Marshall et al. | |
| 8,414,911 B2 | 4/2013 | Mattson et al. | |
| 8,475,437 B2 | 7/2013 | Mrochen et al. | |
| 2001/0055095 A1 | 12/2001 | D'Souza et al. | |
| 2002/0013577 A1 | 1/2002 | Frey et al. | |
| 2002/0159618 A1 | 10/2002 | Freeman et al. | |
| 2002/0164379 A1 | 11/2002 | Nishihara et al. | |
| 2003/0174281 A1 * | 9/2003 | Herekar ............. | A61F 9/00821 351/200 |
| 2003/0175259 A1 | 9/2003 | Karageozian et al. | |
| 2003/0189689 A1 | 10/2003 | Rathjen | |
| 2003/0231285 A1 | 12/2003 | Ferguson | |
| 2004/0002694 A1 | 1/2004 | Pawlowski et al. | |
| 2004/0021874 A1 * | 2/2004 | Shimmick ........... | G01B 9/0209 356/497 |
| 2004/0093046 A1 | 5/2004 | Sand | |
| 2004/0199079 A1 | 10/2004 | Chuck et al. | |
| 2005/0038471 A1 * | 2/2005 | Chan ...................... | A61B 17/11 128/898 |
| 2005/0096515 A1 | 5/2005 | Geng | |
| 2005/0149006 A1 | 7/2005 | Peyman | |
| 2005/0251114 A1 * | 11/2005 | Muhlhoff ................ | A61F 9/008 606/4 |
| 2005/0271590 A1 | 12/2005 | Schwartz et al. | |
| 2006/0135957 A1 | 6/2006 | Panescu | |
| 2006/0149343 A1 | 7/2006 | Altshuler et al. | |
| 2006/0195076 A1 | 8/2006 | Blumenkranz et al. | |
| 2006/0276777 A1 | 12/2006 | Coroneo | |
| 2007/0024860 A1 | 2/2007 | Tobiason et al. | |
| 2007/0048340 A1 | 3/2007 | Bran et al. | |
| 2007/0123845 A1 * | 5/2007 | Lubatschowski ... | A61F 9/00825 606/5 |
| 2007/0135805 A1 | 6/2007 | Peyman | |
| 2007/0142828 A1 | 6/2007 | Peyman | |
| 2007/0265603 A1 | 11/2007 | Pinelli | |
| 2007/0299429 A1 * | 12/2007 | Amano .............. | G02B 27/0093 606/4 |
| 2008/0009901 A1 | 1/2008 | Redmond et al. | |
| 2008/0015660 A1 * | 1/2008 | Herekar ................. | A61N 5/062 607/88 |
| 2008/0043224 A1 * | 2/2008 | Castonguay ....... | G01B 9/02081 356/73 |
| 2008/0063627 A1 | 3/2008 | Stucke et al. | |
| 2008/0114283 A1 | 5/2008 | Mattson et al. | |
| 2008/0139671 A1 | 6/2008 | Herekar | |
| 2008/0208177 A1 | 8/2008 | Mrochen et al. | |
| 2009/0036879 A1 * | 2/2009 | Dai ...................... | A61F 9/008 351/212 |
| 2009/0116096 A1 | 5/2009 | Zalevsky et al. | |
| 2009/0149842 A1 | 6/2009 | Muller et al. | |
| 2009/0149923 A1 | 6/2009 | Herekar | |
| 2009/0171305 A1 | 7/2009 | El Hage | |
| 2009/0213386 A1 * | 8/2009 | LeBlanc ............ | G01B 11/2441 356/495 |
| 2009/0234335 A1 | 9/2009 | Yee | |
| 2009/0275929 A1 | 11/2009 | Zickler | |
| 2010/0028407 A1 | 2/2010 | Del Priore et al. | |
| 2010/0057060 A1 | 3/2010 | Herekar | |
| 2010/0069894 A1 | 3/2010 | Mrochen et al. | |
| 2010/0082018 A1 | 4/2010 | Panthakey et al. | |
| 2010/0094197 A1 * | 4/2010 | Marshall ................ | A61F 9/008 604/20 |
| 2010/0114109 A1 | 5/2010 | Peyman | |
| 2010/0134801 A1 * | 6/2010 | Millerd .............. | G01B 9/02065 356/492 |
| 2010/0145319 A1 * | 6/2010 | Zimare ............... | A61F 9/00821 606/4 |

(56) References Cited

U.S. PATENT DOCUMENTS

| | | | |
|---|---|---|---|
| 2010/0149487 A1 | 6/2010 | Ribak | |
| 2010/0173019 A1 | 7/2010 | Paik et al. | |
| 2010/0182609 A1* | 7/2010 | Wang ................ | G01B 9/02091 |
| | | | 356/491 |
| 2010/0189817 A1 | 7/2010 | Krueger et al. | |
| 2010/0204584 A1 | 8/2010 | Omberg et al. | |
| 2010/0210996 A1 | 8/2010 | Peyman | |
| 2010/0318017 A1 | 12/2010 | Lewis et al. | |
| 2011/0077624 A1 | 3/2011 | Brady et al. | |
| 2011/0098790 A1 | 4/2011 | Daxer | |
| 2011/0118654 A1* | 5/2011 | Muller ................... | A61K 31/14 |
| | | | 604/20 |
| 2011/0152219 A1 | 6/2011 | Stagni et al. | |
| 2011/0190742 A1 | 8/2011 | Anisimov | |
| 2011/0202114 A1 | 8/2011 | Kessel et al. | |
| 2011/0208300 A1 | 8/2011 | Eugene et al. | |
| 2011/0237999 A1* | 9/2011 | Muller ..................... | A61F 9/00 |
| | | | 351/215 |
| 2011/0264082 A1 | 10/2011 | Mrochen | |
| 2011/0288466 A1 | 11/2011 | Muller et al. | |
| 2011/0301524 A1 | 12/2011 | Bueler et al. | |
| 2012/0083772 A1 | 4/2012 | Rubinfield et al. | |
| 2012/0203161 A1 | 8/2012 | Herekar | |
| 2012/0215155 A1 | 8/2012 | Muller et al. | |
| 2012/0289886 A1 | 11/2012 | Muller et al. | |
| 2012/0302862 A1 | 11/2012 | Yun et al. | |
| 2012/0303008 A1 | 11/2012 | Muller et al. | |
| 2012/0310083 A1 | 12/2012 | Friedman et al. | |
| 2012/0310223 A1 | 12/2012 | Knox et al. | |
| 2013/0060187 A1 | 3/2013 | Friedman et al. | |
| 2013/0085370 A1 | 4/2013 | Friedman et al. | |
| 2013/0116757 A1 | 5/2013 | Russmann | |
| 2014/0194957 A1 | 7/2014 | Rubinfield et al. | |
| 2014/0249509 A1 | 9/2014 | Rubinfield et al. | |

FOREIGN PATENT DOCUMENTS

| | | |
|---|---|---|
| EP | 1561440 | 8/2005 |
| EP | 1790383 | 5/2007 |
| IT | MI2010A001236 | 5/2010 |
| KG | 1376 | 8/2011 |
| RU | 2086215 | 8/1997 |
| RU | 2420330 | 6/2011 |
| RU | 2456971 | 7/2012 |
| WO | 2000074648 | 12/2000 |
| WO | 2001058495 | 8/2001 |
| WO | 0226121 A1 | 4/2002 |
| WO | 2005110397 | 11/2005 |
| WO | 2006012947 | 2/2006 |
| WO | 2006128038 | 11/2006 |
| WO | 2007001926 | 1/2007 |
| WO | 2007053826 | 5/2007 |
| WO | 2007120457 | 10/2007 |
| WO | 2007139927 | 12/2007 |
| WO | 2007143111 | 12/2007 |
| WO | 2008000478 | 1/2008 |
| WO | 2008052081 | 5/2008 |
| WO | 2008095075 | 8/2008 |
| WO | 2009073213 | 6/2009 |
| WO | 2009114513 | 9/2009 |
| WO | 2009146151 | 12/2009 |
| WO | 2010011119 | 1/2010 |
| WO | 2010015255 | 2/2010 |
| WO | 2010023705 | 3/2010 |
| WO | 2010093908 | 8/2010 |
| WO | 2011019940 | 2/2011 |
| WO | 2011116306 | 9/2011 |
| WO | 2012004726 | 1/2012 |
| WO | 2012149570 | 11/2012 |
| WO | 2012174453 | 12/2012 |
| WO | 2013148713 | 10/2013 |
| WO | 2013148895 | 10/2013 |
| WO | 2013148896 | 10/2013 |
| WO | 2013149075 | 10/2013 |
| WO | 2014202736 | 12/2014 |

OTHER PUBLICATIONS

Rolandi et al. Correlation of Collagen-Linked Fluorescence and Tendon Fiber Breaking Time. Gerontology 1991;27 :240-243 (4 pages).

Scarcelli, G. et al., "Brillouin Optical Microscopy for Corneal Biomechanics", Investigative Ophthalmology & Visual Science, Jan. 2012, vol. 53, No. 1, pp. 185-190 (6 pages).

Sheehan M., et al., "Illumination System for Corneal Collagen Crosslinking," Optometry and Vision Science, vol. 88, No. 4, pp. 512-524; Apr. 2011 (13 pages).

Spoerl E. et al., "Safety of UVA-Riboflavin Cross-Linking of the Cornea," Cornea, vol. 26, No. 4, pp. 385-389; May 2007 (5 pages).

Spoerl E., et al., "Artificial Stiffening of the Cornea by Induction of Intrastromal Cross-links," Oer Ophthalmologe, vol. 94, No. 12, pp. 902-906; Dec. 1997 (5 pages).

Spoerl E., et al., "Induction of Cross-links in Corneal Tissue," Experimental Eye Research, vol. 66, Issue 1, pp. 97-103; Jan. 1998 (7 pages).

Spoerl E., et al., "Techniques for Stiffening the Cornea," Journal of Refractive Surgery, vol. 15, Issue 6, pp. 711-713; Nov.-Dec. 1999 (4 pages).

Tessier FJ, et al., "Rigidification of Corneas Treated in vitro with Glyceraldehyde: Characterization of Two Novel Crosslinks and Two Chromophores," Investigative Opthalmology & Visual Science, vol. 43, E-Abstract; 2002 (2 pages).

Thorton, I. et al., "Biomechancial Effects of Intraocular Pressure Elevation on Optic Berve/Lamina Cribrosa before and after Peripapillary Scleral Collagen Cross-Linking." Invest. Ophthalmol. Vis. Sci., Mar. 2009, 50(3): pp. 1227-1233.

UV-X: Radiation System for Treatment of Keratokonus, Peschke Meditrade GmbH; retrieved from http://www.peschkemed.ch/ on Sep. 27, 2011 (1 page) (date unknown, prior to Sep. 16, 2008).

Vasan S., et al., "An agent cleaving glucose-derived protein crosslinks in vitro and in vivo;" Letters to Nature, vol. 382, pp. 275-278; Jul. 18, 1996 (4 pages).

Verzijl et al. Crosslinking by Advanced Glycation End Products Increases the Stiffness of the Collagen Network in Human Articular Cartilage. Arthritis & Rheumatism vol. 46, No. 1, Jan. 2002, pp. 114-123 (10 pages).

Wollensak G., "Crosslinking Treatment of Progressive Keratoconus: New Hope," Current Opinion in Ophthalmology, vol. 17(4), pp. 356-360; Aug. 2006 (5 pages).

Wollensak G., et al., "Biomechanical and Histological Changes After Corneal Crosslinking With and Without Epithelial Debridement," J. Cataract Refract. Surg., vol. 35, Issue 3, pp. 540-546; Mar. 2009 (7 pages).

Wollensak G., et al., "Collagen Crosslinking of Human and Porcine Sclera," J. Cataract Refract. Surg., vol. 30, Issue 3, pp. 689-695; Mar. 2004 (7 pages).

Wollensak G., et al., "Cross-linking of Scleral Collagen in the Rabbit Using Riboflavin and UVA," Acta Ophtalmologica Scandinavica, vol. 83(4), pp. 477-482; Aug. 2005 (6 pages).

Wollensak G., et al., "Hydration Behavior of Porcine Cornea Crosslinked with Riboflavin and Ultraviolet," A.J. Cataract Refract. Surg., vol. 33, Issue 3, pp. 516-521; Mar. 2007 (6 pages).

Wollensak G., et al., "Riboflavin/Ultraviolet-A-induced Collagen Crosslinking for the Treatment of Keratoconus," American Journal of Ophthalmology, vol. 135, No. 5, pp. 620-627; May 2003 (8 pages).

Wollensak, G. et al. "Laboratory Science: Stress-Strain Measurements of Human and Porcine Corneas after Riboflavin-Ultraviolet-A-Induced Cross-Linking." Journal of Cataract and Refractive Surgery. vol. 29, No. 9, Sep. 2003 (pp. 1780-1785).

Wong, J. et al., "Post-Lasik ectasia: PRK following previous stablization and effective management with Riboflavin I ultraviolet A-induced collagen cross-linking," Association for Research in Vision and Ophthalmology, 2006 (1 page).

(56)     References Cited

OTHER PUBLICATIONS

Yang H., et al., "3-D Histomorphometry of the Normal and Early Glaucomatous Monkey Optic Nerve Head: Lamina Cribrosa and Peripapillary Scleral Position and Thickness," Investigative Ophthalmology & Visual Science, vol. 48, No. 10, pp. 4597-4607; Oct. 2007 (11 pages).

Yang N., Oster G. Dye-sensitized photopolymerization in the presence of reversible oxygen carriers. J. Phys. Chem. 74, 856-860 (1970).

Zhang, Y. et al., "Effects of Ultraviolet-A and Riboflavin on the Interaction of Collagen and Proteoglycans during Corneal Cross-linking", Journal of Biological Chemistry, vol. 286, No. 15, dated Apr. 5, 2011 (pp. 13011-13022).

International Patent Application No. PCT/US2011/029033, International Search Report, Nov. 30, 2011 (4 pages).

International Patent Application No. PCT/US2011/029033, Written Opinion of the International Searching Authority, Nov. 30, 2011 (5 pages).

International Patent Application No. PCT/US2012/032024, International Search Report, Sep. 24, 2012 (4 pages).

International Patent Application No. PCT/US2012/032024, Written Opinion of the International Searching Authority, Sep. 24, 2012 (6 pages).

Abahussin, M. "3D Collagen Orientation Study of the Human Cornea Using X-ray Diffraction and Femtosecond Laser Technology" Investigative Ophthalmology & Visual Science, Nov. 2009, vol. 50, No. 11, pp. 5159-5164 (6 pages).

Averianova, O. S., "Nastoyaschee I buduschee kross-linkage." Mir Ofalmologii, 2010, [online] [retrieved on Feb. 13, 2014] Retrieved from the internet: http:/ /miroft.org.ua!publications/.html.

Baier J. et al., "Singlet Oxygen Generation by UVA Light Exposure of Endogenous Photosensitizers," Biophysical Journal, vol. 91(4), pp. 1452-1459; Aug. 15, 2006 (8 pages).

Ballou, D. et al., "Direct Demonstration Of Superoxide Anion Production During The Oxidation Of Reduced Flavin And Of Its Catalytic Decomposition By Erythrocuprein," Biochemical And Biophysical Research Communications vol. 36, No. 6, pp. 898-904, Jul. 11, 1969 (7 pages).

Barbarino, S. et al., "Post-LASIK ectasia: Stabilization and Effective Managmeent with Riboflavin / ultraviolet A-induced collagen cross-linking," Association for Research in Vision and Ophthalmology, 2006 (1 page).

Bruel, A., "Changes In Biomechanical Properties, Composition Of Collagen And Elastin, And Advanced Glycation Endproducts Of The Rat Aorta In Relation To Age," Atherosclerosis 127, Mar. 14, 1996 (11 pages).

Chace, K.V. et al., Abstract for "The role of nonenzymatic glycosylation, transition metals, and free radicals in the formation of collagen aggregates", Arch Biochem Biophys., Aug. 1, 1991, 288(2) pp. 473-480 (1 page).

Chai, D. et al., "Quantitative Assessment of UVA-Riboflavin Corneal Cross-Linking Using Nonlinear Optical Microscopy," Investigative Ophthalmology & Visual Science, Jun. 2011, vol. 52, No. 7, 4231-4238 (8 pages).

Chan B.P., et al., "Effects of photochemical crosslinking on the microstructure of collagen and a feasibility study on controlled protein release;" Acta Biomaterialia, vol. 4, Issue 6, pp. 1627-1636; Jul. 1, 2008 (10 pages).

Clinical Trials.gov, "Riboflavin Mediated Corneal Crosslinking for Stabilizing Progression of Keratoconus (CCL)," University Hospital Freiburg, Feb. 20, 2008; retrieved from http://www.clinicaltrials.gov/ct2/show/NCT00626717, on Apr. 26, 2011 (3 pages).

Coskenseven E. et al., "Comparative Study of Corneal Collagen Cross-linking With Riboflaving and UVA Irradiation in Patients With Keratoconus," Journal of Refractive Surgery, vol. 25, issue 4, pp. 371-376; Apr. 2009 (6 pages).

Erskine H., "Avedro Becomes Sponsor of US FDA Clinical Trials of Corneal Collagen Crosslinking," Press Release, Mar. 16, 2010 (1 page).

Fite et al. Noninvasive Multimodal Evaluation of Bioengineered Cartilage Constructs Combining Time-Resolved Fluorescence and Ultrasound Imaging. Tissue Eng: Part C vol. 17, No. 4, 2011 (10 pages).

Friedman, M. et al. "Advanced Corneal Cross-Linking System with Fluorescence Dosimetry", Journal of Ophthalmology, vol. 2012, Article ID 303459, dated May 7, 2012 (6 pages).

Gibson, Q. et al., "The Oxidation Of Reduced Flavin Mononucleotide By Molecular Oxygen," Biochem. J. (1962) 83, 368-377 (10 pages).

Givens et al. "A Photoactivated Diazpryruvoyl Cross-Linking Agent for Bonding Tissue Containing Type-I Collagen." Photochemistry and Photobiology. vol. 78, No. 1, 2003 (pp. 23-29).

Glenn J.V., et al., "Advanced Glycation End Product (AGE) Accumulation on Bruch's Membrane: Links to Age-Related RPE Dysfunction;" Investigative Ophthalmology & Visual Science, vol. 50, No. 1, pp. 441-451; Jan. 2009 (11 pages).

Hafezi F., et al., "Collagen Crosslinking with Ultraviolet-A and Hypoosmolar Riboflavin Solution in Thin Corneas," J. Catract Refract. Surg., vol. 35, No. 1, pp. 621-624; Apr. 2009 (4 pages).

Hitzenberger et al., "Birefringence Properties Of The Human Cornea Measured With Polarization Sensitive Optical Coherence Tomography," Bull. Soc. Beige Ophtalmol., 302, 153-168, 2006.

Holmstrom, B. et al., "Riboflavin As An Electron Donor In Photochemical Reactions," 1867-1871, Nov. 29, 1960 (5 pages).

Imex, "KXL System: Crosslinking Para Cirugia Corneal Bibliografia Cientifica," Product Literature, Nov. 23, 2010 (24 pages).

Kamaev et al., "Photochemical Kinetics Of Corneal Cross-Linking With Riboflavin," Investigative Ophthalmology & Visual Science, Apr. 2012, vol. 53, No. 4, pp. 2360-2367 (8 pages).

Kampik D. et al., "Influence of Corneal Collagen Crosslinking With Riboflavin and Ultraviolet-A Irradiation on Excimer Laser Surgery," Investigative Opthalmology & Visual Science, vol. 51, No. 8, pp. 3929-3934; Aug. 2010 (6 pages).

Kanellopoulos, A. J., "Collagen Cross-linking in Early Keratoconus With Riboflavin in a Femtosecond Laser-created Pocket: Initial Clinical Results", Journal of Refractive Surgery, Aug. 18, 2009.

Kanellopoulos, A. J., "Keratoconus management: UV A-induced collagen cross-linking followed by a limited topo-guided surface excimer ablation," American Academy of Ophthalmology, 2006 (25 pages).

Kanellopoulos, A. J., "Ultraviolet A cornea collagen cross-linking, as a pre-treatment for surface excimer ablation in the management of keratoconus and post-LASIK ectasia," American Academy of Ophthalmology, 2005 (28 pages).

Kissner Anja, et al., "Pharmacological Modification of the Epithelial Permeability by Benzalkonium Chloride in UVNRiboflavin Corneal Collagen Cross-Linking," Current Eye Research 35(8), pp. 715-721; Mar. 2010 (7 pages).

Koller T., et al., "Therapeutische Quervernetzung der Hornhaut mittels UVA und Riboflavin: Therapeutic Cross-Linking of the Cornea Using Riboflavin/UVA," Klinische Monatsblatter fur Augenheilkunde, val. 224, No. 9, pp. 700-706; Sep. 2007 (7 pages).

Koller, T. et. al., "Complication and failure rates after corneal crosslinking," Journal Cataract and refractive surgery, vol. 35, No. 8, Aug. 2009, pp. 1358-1362.

Kornilovsky, I. M. "Novye neinvazivnye tekhnologii lazernoy modifikatsii optiko-refraksionnykk struktur glaza. Refraktsionnaya khirurgiya I oftalmologiya." vol. 9, No. 3, 2006 (pts. 17-26).

Krueger Ronald R., "Rapid VS Standard Collagen CXL with Equivalent Energy Dosing," presentation slides, (26 pages); available at http://www.slideshare.net/logen/krueger-kerekar-rapid-cross-linking (date unknown, prior to Nov. 9, 2009).

Li, C. et al. "Elastic Properties of Soft Tissue-Mimicking Phantoms Assessed by Combined Use of Laser Ultrasonics and Low Coherence Interferometry." Optics Express. vol. 19, No. 11, May 9, 2011 (pp. 10153-10163).

Li, C. et al. "Noncontact All-Optical Measurement of Corneal Elasticity." Optics Letters. vol. 37, No. 10, May 15, 2012 (pp. 1625-1627).

Li, P. et al. "In Vivo Microstructural and Microvascular Imaging of the Human Corneo-Scleral Limbus Using Optical Coherence Tomography." Biomedical Optics Express. vol. 2, No. 11, Oct. 18, 2011 (pp. 3109-3118).

(56)　　　　　References Cited

OTHER PUBLICATIONS

Marzouky, et al., Tensioactive-mediated Transepithelial Corneal Cross-linking—First Laboratory Report, European Ophthalmic Review, 2009, 3(2), pp. 67-70.

Massey, V., "Activation Of Molecular Oxygen By Flavins And Flavoproteins," The Journal of Biological Chemistry vol. 269, No. 36, Issue of Sep. 9, pp. 22459-22462, 1994 (4 pages).

Meek, K.M. et al. "The Cornea and Sclera", Collagen: Structure and Mechanics, Chapter 13, pp. 359-396, 2008 (38 pages).

Mi S., et al., "The adhesion of LASIK-like flaps in the cornea: effects of cross-linking, stromal fibroblasts and cytokine treatment," presented at British Society for Matrix Biology annual Meeting, Cardiff, UK, Sep. 8-9, 2008 (17 pages).

Muller L., et al., "The Specific Architecture of the Anterior Stroma Accounts for Maintenance of Corneal Curvature," Br. J. Opthalmol., vol. 85, pp. 437-443; Apr. 2001 (8 pages).

Mulroy L., et al., "Photochemical Keratodesmos for repair of Lamellar corneal Incisions;" Investigative Ophthalmology & Visual Science, vol. 41, No. 11, pp. 3335-3340; Oct. 2000 (6 pages).

O'Neil A.C., et al., "Microvascular Anastomosis Using a Photochemical Tissue Bonding Technique;" Lasers in Surgery and Medicine, vol. 39, Issue 9, pp. 716-722; Oct. 2007 (7 pages).

Pinelli R., et al., "C3-Riboflaving Treatments: Where Did We Come From? Where Are We Now?" Cataract & Refractive Surgery Today Europe, Summer 2007, pp. 36-46; Jun. 2007 (10 pages).

Pinelli, R. "Corneal Cross-Linking with Riboflavin: Entering a New Era in Ophthalmology." Ophthalmology Times Europe. vol. 2, No. 7, Sep. 1, 2006 (3 pages).

Pinelli, R., "Panel Discussion: Epithelium On/Off, Corneal abrasion for CCL contra", presented at the 3° International Congress of Corneal Cross Linking on Dec. 7-8, 2007 in Zurich (36 pages).

Ponce C., et al., "Central and Peripheral Corneal Thickness Measured with Optical Coherence Tomography, Scheimpflug Imaging, and Ultrasound Pachymetry in Normal, Keratoconus-suspect and Post-laser in situ Keratomileusis Eyes," J. Cataract Refract. Surgery, vol. 35, No. 6, pp. 1055-1062; Jun. 2009 (8 pages).

Proano C.E., et al., "Photochemical Keratodesmos for Bonding Corneal Incisions;" Investigative Ophthalmology & Visual Science, vol. 45, No. 7, pp. 2177-2181; Jul. 2004 (5 pages).

Randall, J. et al., "The Measurement and Intrepretation of Brillouin Scattering in the Lens of the Eye," The Royal Society, Abstract only, published 2013 [available online at http://rspb.royalsocietypublishing.org/content/214/11971449.short] (1 page).

Reinstein, D. Z. et al. "Epithelial Thickness Profile as a Method to Evaluate the Effectiveness of Collagen Cross-Linking Treatment After Corneal Ectasis." Journal of Refractive Surgery. vol. 27, No. 5, May 2011 (pp. 356-363). [Abstract only].

Reiss, S. et al., "Non-Invasive, ortsaufgeloeste Bestimmung von Gewebeeigenschaften derAugenlinse, Dichte undProteinkonzentration unter Anwendung der Brillouin-spektroskopie", Klin Monatsbl Augenheilkd, vol. 228, No. 12, pp. 1079-1085, Dec. 13, 2011 (7 pages).

Reiss, S. et al., "Spatially resolved Brillouin Spectroscopy to determine the rheological properties of the eye lens", Biomedical Optics Express, vol. 2, No. 8, p. 2144, Aug. 1, 2011 (1 page).

Examination Report for related European Application No. 19162368.5; action dated Jun. 7, 2022; (5 pages).

Extended European Search Report from European Patent Application No. 24212449.3, dated Jan. 14, 2025. 11 pages.

* cited by examiner

200A

200B

200C

210— Treat corneal tissue with cross-linking agent.

Cross-linking agent —130

215— Apply mask to correspond to the areas outside treatment zone.

Mask with pattern for activating cross-linking agent —1010

220— Initiate cross-linking in corneal tissue by activating cross-linking agent with initiating element.

Initiating element —222

900A

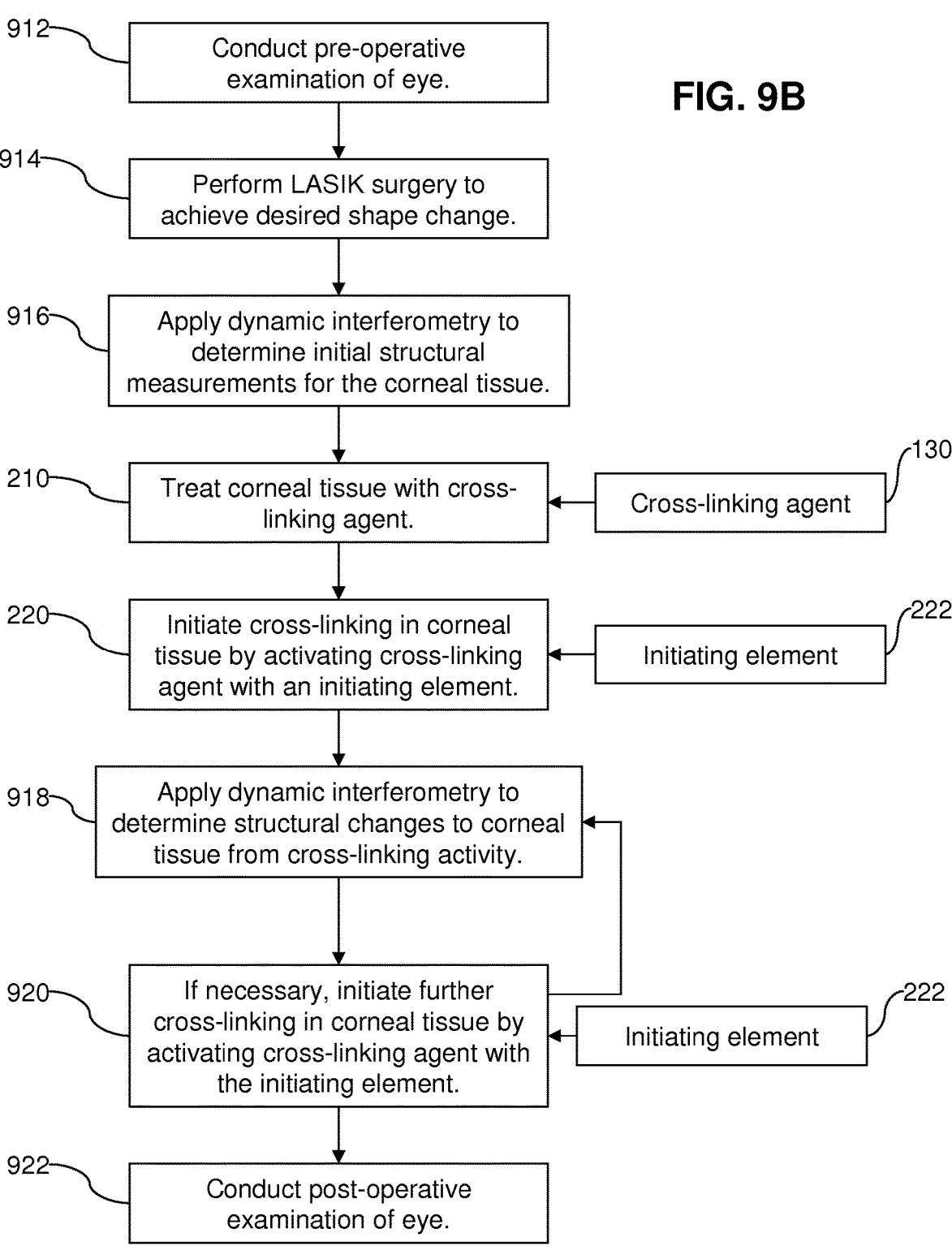

FIG. 9B

912 — Conduct pre-operative examination of eye.

914 — Perform LASIK surgery to achieve desired shape change.

916 — Apply dynamic interferometry to determine initial structural measurements for the corneal tissue.

210 — Treat corneal tissue with cross-linking agent.

130 — Cross-linking agent

220 — Initiate cross-linking in corneal tissue by activating cross-linking agent with an initiating element.

222 — Initiating element

918 — Apply dynamic interferometry to determine structural changes to corneal tissue from cross-linking activity.

920 — If necessary, initiate further cross-linking in corneal tissue by activating cross-linking agent with the initiating element.

222 — Initiating element

922 — Conduct post-operative examination of eye.

924 — Treat corneal tissue with cross-linking agent.

925 — Cross-linking agent with concentration $C_1$

926 — Allow diffusion of cross-linking agent during a period of time $T_1$.

900C

928 — Initiate cross-linking in corneal tissue by activating cross-linking agent with initiating element.

929 — Initiating element, *e.g.*, UV light, with power $P_1$

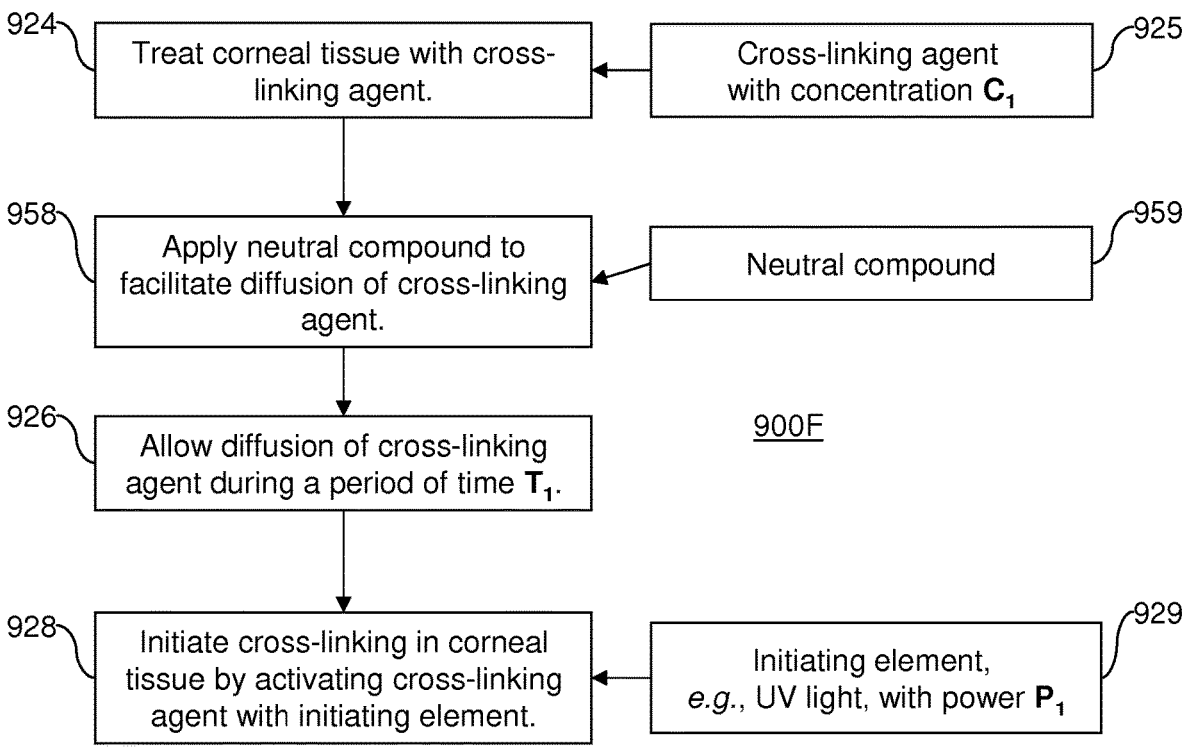

924 — Treat corneal tissue with cross-linking agent.

925 — Cross-linking agent with concentration $C_1$

958 — Apply neutral compound to facilitate diffusion of cross-linking agent.

959 — Neutral compound

926 — Allow diffusion of cross-linking agent during a period of time $T_1$.

900F

928 — Initiate cross-linking in corneal tissue by activating cross-linking agent with initiating element.

929 — Initiating element, e.g., UV light, with power $P_1$

FIG. 9F

SYSTEMS AND METHODS FOR APPLYING AND MONITORING EYE THERAPY

CROSS REFERENCE TO RELATED APPLICATIONS

This application is a continuation of U.S. patent application Ser. No. 13/051,699, filed Mar. 18, 2011, which claims priority to: U.S. Provisional Application No. 61/315,840, filed Mar. 19, 2010; U.S. Provisional Application No. 61/319,111, filed Mar. 30, 2010; U.S. Provisional Application No. 61/326,527, filed Apr. 21, 2010; U.S. Provisional Application No. 61/328,138, filed Apr. 26, 2010; U.S. Provisional Application No. 61/377,024, filed Aug. 25, 2010; U.S. Provisional Application No. 61/388,963, filed Oct. 1, 2010; U.S. Provisional Application No. 61/409,103, filed Nov. 1, 2010; and U.S. Provisional Application No. 61/423,375, filed Dec. 15, 2010, the contents of each of these applications being incorporated entirely herein by reference.

BACKGROUND OF THE INVENTION

Field of the Invention

The invention pertains to systems and methods for stabilizing corneal tissue, and more particularly, systems and methods for applying and activating a cross-linking agent in corneal tissue and monitoring the activation of the cross-linking agent.

Description of Related Art

A variety of eye disorders, such as myopia, keratoconus, and hyperopia, involve abnormal shaping of the cornea. Laser-assisted in-situ keratomileusis (LASIK) is one of a number of corrective procedures that reshape the cornea so that light traveling through the cornea is properly focused onto the retina located in the back of the eye. During LASIK eye surgery, an instrument called a microkeratome is used to cut a thin flap in the cornea. The cornea is then peeled back and the underlying cornea tissue ablated to the desired shape with an excimer laser. After the desired reshaping of the cornea is achieved, the cornea flap is put back in place and the surgery is complete.

In another corrective procedure that reshapes the cornea, thermokeratoplasty provides a noninvasive procedure that applies electrical energy in the microwave or radio frequency (RF) band to the cornea. In particular, the electrical energy raises the corneal temperature until the collagen fibers in the cornea shrink at about 60° C. The onset of shrinkage is rapid, and stresses resulting from this shrinkage reshape the corneal surface. Thus, application of energy according to particular patterns, including, but not limited to, circular or annular patterns, may cause aspects of the cornea to flatten and improve vision in the eye.

The success of procedures, such as LASIK or thermokeratoplasty, in addressing eye disorders, such as myopia, keratoconus, and hyperopia, depends on the stability of the changes in the corneal structure after the procedures have been applied.

BRIEF SUMMARY

Embodiments according to aspects of the present disclosure provide systems and methods for stabilizing corneal tissue and improving its biomechanical strength, particularly after desired structural changes have been achieved in the corneal tissue. For example, the embodiments help to preserve the desired reshaping of the cornea produced by LASIK surgery, thermokeratoplasty, or other similar treatments.

According to aspects of the present disclosure, after a treatment produces a desired change to the shape of a cornea, a cross-linking agent is activated in the treated region of the cornea. The cross-linking agent prevents the corneal fibrils in the treated regions from moving and causing undesired changes to the shape of the cornea. An initiating element may be applied to the treated corneal fibrils to activate the cross-linking agent.

In some embodiments, for example, the cross-linking agent may be Riboflavin and the initiating element may be photoactivating light, such as ultraviolet (UV) light. In these embodiments, the photoactivating light initiates cross-linking activity by irradiating the applied cross-linking agent to release reactive oxygen radicals in the corneal tissue. In particular, the cross-linking agent, e.g., Riboflavin, acts as a sensitizer to convert $O_2$ into singlet oxygen which causes cross-linking within the corneal tissue.

The initiating element may be applied according to a selected pattern to stabilize and strengthen the regions of the cornea where structural changes have been generated by the treatment. Accordingly, aspects of the present disclosure may include a delivery system that accurately and precisely delivers the initiating element to corneal fibrils according to a selected pattern. In embodiments where the initiating element is UV light, the delivery system may deliver the UV light in the form of a laser.

In some embodiments, the UV light may be delivered with laser scanning technologies. Embodiments may also employ aspects of multiphoton excitation microscopy. Advantageously, the use of laser scanning technologies allows cross-linking to be activated more effectively beyond the surface of the cornea, at depths where stronger and more stable corneal structure is desired. In particular, treatment may generate desired changes in corneal structure at the mid-depth region. The application of the initiating element is applied precisely according to a selected three-dimensional pattern and is not limited to a two-dimensional area at the surface of the cornea. In general, embodiments stabilize a three-dimensional structure of corneal tissue through selective application and activation of cross-linking in the corneal tissue.

Aspects of the present disclosure also provide devices, systems, and approaches for monitoring the reshaping and strengthening of the corneal tissue, and for activating the cross-linking in the corneal tissue in an iterative approach. Additionally, some embodiments may employ a feedback system to determine how to iteratively activate the cross-linking agent in the corneal tissue, and how to adjust subsequent activations of the cross-linking agent.

Aspects of the present disclosure provide a system for controlling activation of a cross-linking agent applied to an eye. The system includes a feedback system, a controller, and a cross-linking activation system. The feedback system provides feedback information indicative of a biomechanical strength of corneal tissue of the eye. The controller receives the feedback information and automatically determines an indication of an amount of cross-linking in the corneal tissue based on the received feedback information. The cross-linking activation system initiates cross-linking in the corneal tissue according to one or more control signals generated by the controller. The one or more control signals can be generated according to a function including the determined indication of the amount of cross-linking in the corneal tissue.

In some embodiments, the feedback system is an interferometer adapted to interfere a beam of light reflected from a surface of the eye with a reference beam of light reflected from a reference surface. The interfering beams of light can pass through a polarizing filter and create an intensity pattern detected by a camera associated with the feedback system. The feedback information can be an output from the associated camera. The feedback system can also include a distance measurement system for monitoring a distance between the eye and the interferometer and provide an indication of the monitored distance to the controller. The associated camera can be adapted to detect a plurality of intensity patterns and the controller can be further adapted to: receive the plurality of detected intensity patterns; determine a plurality of surface profiles of the surface of the eye associated with the plurality of detected intensity patterns based on the plurality of detected intensity patterns and based on the monitored distance; and determine an amount of dynamic deformation of the surface of the eye based on the determined plurality of surface profiles.

Aspects of the present disclosure further provide a method for controllably activating a cross-linking agent applied to an eye. The method includes receiving feedback information including electronic signals output from a feedback system adapted to monitor the eye. The feedback information is indicative of a biomechanical strength of corneal tissue of the eye. The method also includes automatically analyzing the feedback information to determine a dosage of light to be applied to the eye. The method also includes activating the cross-linking agent by conveying light to the eye according to the determined dosage. The method may also include receiving targeting information indicative of an alignment of the eye with respect to the conveyed light. The method may also include automatically adjusting the alignment of the eye with respect to the conveyed light according to the received targeting information.

Aspects of the present disclosure further provide a method for activating cross-linking in corneal tissue of an eye. The method includes applying a cross-linking agent having a first concentration to the eye. The method also includes allowing, during a first diffusion time, the cross-linking agent having the first concentration to diffuse within the eye. The method also includes activating the cross-linking agent with a photoactivating light applied according to a first dose, the first dose specified by a first power and a first bandwidth. The method also includes activating the cross-linking agent with the photoactivating light applied according to a second dose, the second dose specified by a second power and a second bandwidth.

Aspects of the present disclosure also provide a system for activating a cross-linking agent applied to a cornea of an eye. The system includes a light source for emitting photoactivating light sufficient for activating cross-linking in the corneal tissue by exciting the cross-linking agent to produce a reactive singlet oxygen from oxygen content in corneal tissue of the eye. The system also includes a mirror array having a plurality of mirrors arranged in rows and columns. The plurality of mirrors are adapted to selectively direct the photoactivating light toward the eye according to a pixelated intensity pattern having pixels corresponding to the plurality of mirrors in the mirror array. The plurality of mirrors are alignable according to one or more control signals. The system also includes a controller for providing the one or more control signals to programmatically align the plurality of mirrors in the array of mirrors such that the pixelated intensity pattern emerges from the mirror array responsive to the photoactivating light scanning across the plurality of mirrors.

Aspects of the present disclosure further include a method of activating a cross-linking agent applied to an eye. The method includes emitting photoactivating light sufficient for activating cross-linking in the corneal tissue by exciting the cross-linking agent to produce a reactive singlet oxygen from oxygen content in corneal tissue of the eye. The method also includes directing the photoactivating light to be scanned across a mirror array having a plurality of mirrors arranged in rows and columns. The plurality of mirrors are adapted to selectively direct the photoactivating light toward the eye according to a pixelated intensity pattern having pixels corresponding to the plurality of mirrors in the mirror array. The plurality of mirrors are alignable according to one or more control signals. The method also includes generating the one or more control signals for programmatically aligning the plurality of mirrors in the mirror array according to the pixelated intensity pattern.

Aspects of the present disclosure also provide a system for activating a cross-linking agent applied to an eye. The system includes a light source for emitting photoactivating light sufficient for activating cross-linking in the corneal tissue by exciting the cross-linking agent to produce a reactive singlet oxygen from oxygen content in corneal tissue of the eye. The system also includes a mask adapted to selectively allow the photoactivating light to be transmitted therethrough. The regions of the mask allowing the photoactivating light to be transmitted define a pattern of activation of the cross-linking agent.

Aspects further provide a method of activating a cross-linking agent applied to an eye. The method includes emitting photoactivating light sufficient for activating cross-linking in the corneal tissue by exciting the cross-linking agent to produce a reactive singlet oxygen from oxygen content in corneal tissue of the eye. The method further includes directing the photoactivating light to pass through a mask adapted to selectively allow the photoactivating light to be transmitted therethrough. The regions of the mask allowing the photoactivating light to be transmitted defining a pattern of activation of the cross-linking agent.

Aspects further provide a system for monitoring an eye. The system includes an interferometer and a controller. The interferometer includes a light source for providing a beam of light having a reference polarization state. The interferometer also includes a corneal imaging lens for directing a beam of light from the light source toward a surface of the eye and collimating light reflected from the surface of the eye. The interferometer also includes a reference surface for providing a reference surface to compare with a surface of the eye. The interferometer also includes one or more beam splitters adapted to split the beam of light and direct a first portion to be reflected from the surface of the eye, and direct a second portion to be reflected from the reference surface; and combine the reflected first portion and the reflected second portion to form a superimposed beam. The interferometer also includes a polarizing filter, and a camera for capturing an intensity pattern of the superimposed beam emerging from the polarizing filter. The controller analyzes the intensity pattern by determining a phase offset, for a plurality of points in the captured intensity pattern, between the reflected first portion and the reflected second portion based on the captured intensity pattern. The controller further analyzes the intensity pattern by determining an optical path length difference between the reflected first portion and the reflected second portion for the plurality of points from the phase offsets determined for the plurality of points. The controller further analyzes the intensity pattern by determining a surface profile of the eye by comparing a profile of the reference surface to the optical path length differences determined for the plurality of points.

Aspects of the present disclosure further provide a method of monitoring an eye. The method includes emitting a beam of light from a light source having a known polarization. The method also includes splitting the beam and directing a first portion to be reflected from a surface of the eye, and directing a second portion to be reflected from a reference surface. The method also includes interfering the first portion of the beam and second portion of the beam to create a superimposed beam. The method also includes directing the superimposed beam through a polarizing filter. The method also includes capturing an intensity pattern of the superimposed beam emerging from the polarizing filter. The method also includes analyzing the captured intensity pattern to determine a surface profile of the surface of the eye.

Aspects of the present disclosure further provide a system for applying a controlled amount of cross-linking in corneal tissue of an eye. The system includes an applicator adapted to apply a cross-linking agent to the eye. The system also includes a light source adapted to emit a photoactivating light. The system also includes a targeting system adapted to create targeting feedback information indicative of a position of a cornea of the eye. The system also includes a mirror array having a plurality of mirrors arranged in rows and columns. The plurality of mirrors are adapted to selectively direct the photoactivating light toward the eye according to a pixelated intensity pattern having pixels corresponding to the plurality of mirrors in the mirror array. The system also includes an interferometer adapted to monitor an amount of cross-linking in the corneal tissue. The interferometer monitors the amount of cross-linking in the corneal tissue by interfering a beam of light reflected from a surface of the eye with a reference beam of light reflected from a reference surface. The interferometer monitors the amount of cross-linking in the corneal tissue by also capturing, via an associated camera, a series of images of interference patterns due to optical interference between the beam of light and the reference beam of light. The series of images are indicative of a plurality of profiles of the surface of the eye. The system also includes a head restraint device for restraining a position of a head associated with the eye. The head restraint device thereby aligns the eye with respect to the interferometer. The system also includes a controller. The controller is adapted to receive the targeting feedback information and receive the generated series of intensity patterns. The controller is also adapted to analyze the generated series of intensity patterns to determine the plurality of profiles of the surface of the eye associated therewith. The controller is also adapted to determine an amount of cross-linking of the corneal tissue based on a dynamic deformation of the surface of the eye. The dynamic deformation of the eye is indicated by the plurality of profiles of the surface of the eye. The controller is also adapted to adjust the pixelated intensity pattern according to data. The data includes at least one of: the targeting feedback information and the determined amount of cross-linking.

These and other aspects of the present disclosure will become more apparent from the following detailed description of embodiments of the present disclosure when viewed in conjunction with the accompanying drawings.

BRIEF DESCRIPTION OF THE DRAWINGS

FIG. 9B provides a flowchart for using an interferometer to conduct pre-operative and post-operative examination of the corneal structure to be treated with LASIK surgery and the cross-linking agent.

FIG. 9F provides an embodiment similar to the embodiment of FIG. 9C, but where the diffusion of the cross-linking agent is assisted by use of a neutral compound after the cross-linking agent has been applied.

DETAILED DESCRIPTION

Figure 1:
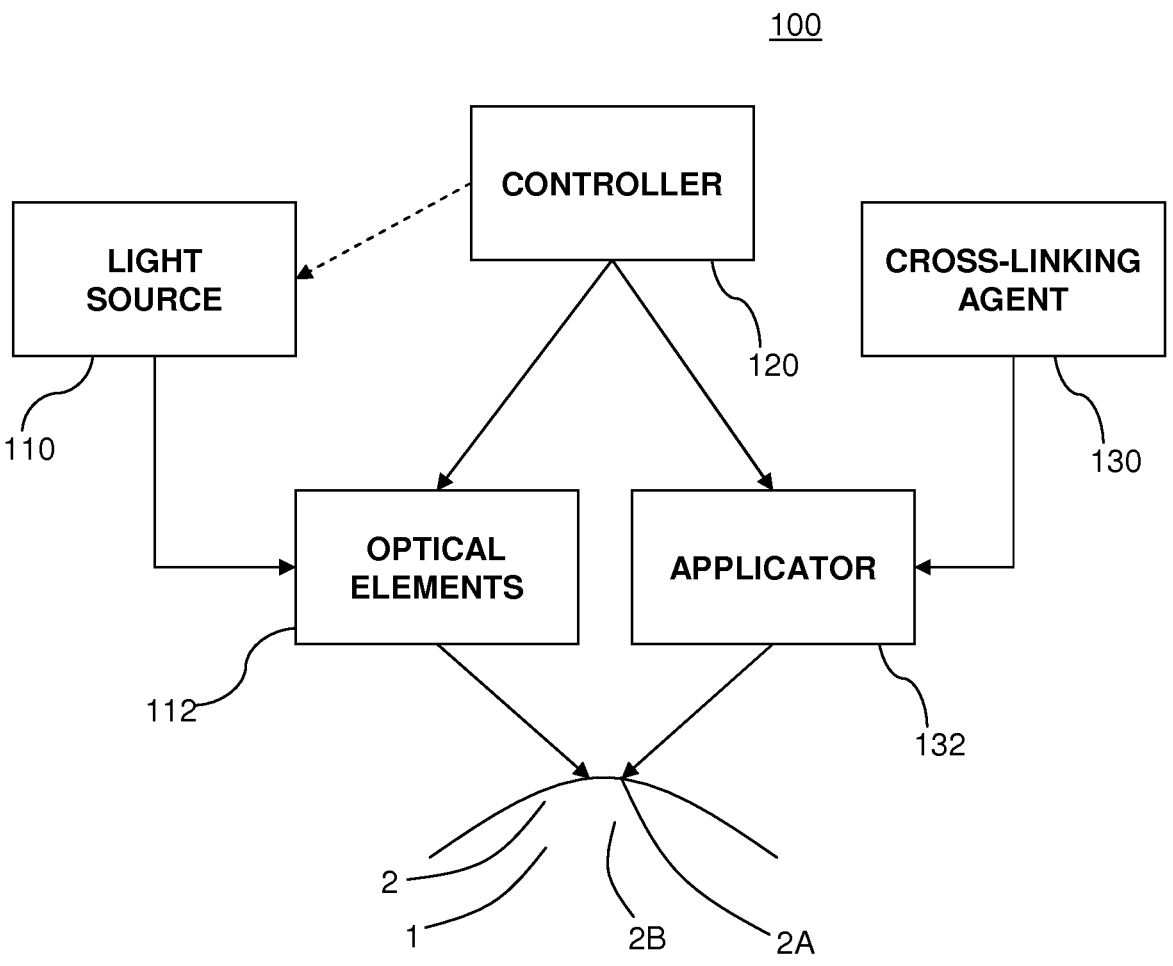
FIG. 1 provides a block diagram of an example delivery system for delivering a cross-linking agent and an activator to a cornea of an eye in order to initiate molecular cross-linking of corneal collagen within the cornea.

FIG. 1 provides a block diagram of an example delivery system 100 for delivering a cross-linking agent 130 and an activator to a cornea 2 of an eye 1 in order to initiate molecular cross-linking of corneal collagen within the cornea 2. Cross-linking can stabilize corneal tissue and improve its biomechanical strength. The delivery system 100 includes an applicator 132 for applying the cross-linking agent 130 to the cornea 2. The delivery system 100 includes a light source 110 and optical elements 112 for directing light to the cornea 2. The delivery system 100 also includes a controller 120 that is coupled to the applicator 132 and the optical elements 112. The applicator 132 may be an apparatus adapted to apply the cross-linking agent 130 according to particular patterns on the cornea 2 advantageous for causing cross-linking to take place within the corneal tissues. The applicator 132 may apply the cross-linking agent 130 to a corneal surface 2A (e.g., an epithelium), or to other locations on the eye 1. Particularly, the applicator 132 may apply the cross-linking agent 130 to an abrasion or cut of the corneal surface 2A to facilitate the transport or penetration of the cross-linking agent through the cornea 2 to a mid-depth region 2B.

As described below in connection with FIGS. 2A-2B, which describe an exemplary operation of the delivery system 100, the cross-linking agent 130 is applied to the cornea 2 using the applicator 132. Once the cross-linking agent 130 has been applied to the cornea 2, the cross-linking agent 130 is initiated by the light source 110 (i.e. the initiating element) to cause cross-linking agent 130 to absorb enough energy to release free oxygen radicals within the cornea 2. Once released, the free oxygen radicals (i.e. singlet oxygen) form covalent bonds between corneal collagen fibrils and thereby cause the corneal collagen fibrils to cross-link and change the structure of the cornea 2. For example, activation of the cross-linking agent 130 with the light source 110 delivered to the cornea 2 through the optical elements 112 may result in cross-linking in the mid-depth region 2B of the cornea 2 and thereby strengthen and stiffen the structure of the cornea 2.

Although eye therapy treatments may initially achieve desired reshaping of the cornea 2, the desired effects of reshaping the cornea 2 may be mitigated or reversed at least partially if the collagen fibrils within the cornea 2 continue to change after the desired reshaping has been achieved. Indeed, complications may result from further changes to the cornea 2 after treatment. For example, a complication known as post-LASIK ectasia may occur due to the permanent thinning and weakening of the cornea 2 caused by LASIK surgery. In post-LASIK ectasia, the cornea 2 experiences progressive steepening (bulging).

Aspects of the present disclosure provide approaches for initiating molecular cross-linking of corneal collagen to stabilize corneal tissue and improve its biomechanical strength. For example, embodiments may provide devices and approaches for preserving the desired corneal structure and shape that result from an eye therapy treatment, such as LASIK surgery or thermokeratoplasty. In addition, aspects of the present disclosure may provide devices and approaches for monitoring the shape, molecular cross-linking, and biomechanical strength of the corneal tissue and providing feedback to a system for providing iterative initiations of cross-linking of the corneal collagen. As described herein, the devices and approaches disclosed herein may be used to preserve desired shape or structural changes following an eye therapy treatment by stabilizing the corneal tissue of the cornea 2. The devices and approaches disclosed herein may also be used to enhance the strength or biomechanical structural integrity of the corneal tissue apart from any eye therapy treatment.

Therefore, aspects of the present disclosure provide devices and approaches for preserving the desired corneal structure and shape that result from an eye treatment, such as LASIK surgery or thermokeratoplasty. In particular, embodiments may provide approaches for initiating molecular cross-linking of the corneal collagen to stabilize the corneal tissue and improve its biomechanical strength and stiffness after the desired shape change has been achieved. In addition, embodiments may provide devices and approaches for monitoring cross-linking in the corneal collagen and the resulting changes in biomechanical strength to provide a feedback to a system for inducing cross-linking in corneal tissue.

Some approaches initiate molecular cross-linking in a treatment zone of the cornea 2 where structural changes have been induced by, for example, LASIK surgery or thermokeratoplasty. However, it has been discovered that initiating cross-linking directly in this treatment zone may result in undesired haze formation. Accordingly, aspects of the present disclosure also provide alternative techniques for initiating cross-linking to minimize haze formation. In particular, the structural changes in the cornea 2 are stabilized by initiating cross-linking in selected areas of corneal collagen outside of the treatment zone. This cross-linking strengthens corneal tissue neighboring the treatment zone to support and stabilize the actual structural changes within the treatment zone.

With reference to FIG. 1, the optical elements 112 may include one or more mirrors or lenses for directing and focusing the light emitted by the light source 110 to a particular pattern on the cornea 2 suitable for activating the cross-linking agent 130. The light source 110 may be an ultraviolet light source, and the light directed to the cornea 2 through the optical elements 112 may be an activator of the cross-linking agent 130. The light source 110 may also alternatively or additionally emit photons with greater or lesser energy levels than ultraviolet light photons. The delivery system 100 also includes a controller 120 for controlling the operation of the optical elements 112 or the applicator 132, or both. By controlling aspects of the operation of the optical elements 112 and the applicator 132, the controller 120 can control the regions of the cornea 2 that receive the cross-linking agent 130 and that are exposed to the light source 110. By controlling the regions of the cornea 2 that receive the cross-linking agent 130 and the light source 110, the controller 120 can control the particular regions of the cornea 2 that are strengthened and stabilized through cross-linking of the corneal collagen fibrils. In an implementation, the cross-linking agent 130 can be applied generally to the eye 1, without regard to a particular region of the cornea 2 requiring strengthening, but the light source 110 can be directed to a particular region of the cornea 2 requiring strengthening, and thereby control the region of the cornea 2 wherein cross-linking is initiated by controlling the regions of the cornea 2 that are exposed to the light source 110.

The optical elements 112 can be used to focus the light emitted by the light source 110 to a particular focal plane within the cornea 2, such as a focal plane that includes the mid-depth region 2B. In addition, according to particular embodiments, the optical elements 112 may include one or more beam splitters for dividing a beam of light emitted by the light source 110, and may include one or more heat sinks for absorbing light emitted by the light source 110. The optical elements 112 may further include filters for partially blocking wavelengths of light emitted by the light source 110 and for advantageously selecting particular wavelengths of light to be directed to the cornea 2 for activating the cross-linking agent 130. The controller 120 can also be adapted to control the light source 110 by, for example, toggling a power switch of the light source 110.

In an implementation, the controller 120 may include hardware and/or software elements, and may be a computer. The controller 120 may include a processor, a memory storage, a microcontroller, digital logic elements, software running on a computer processor, or any combination thereof. In an alternative implementation of the delivery system 100 shown in FIG. 1, the controller 120 may be replaced by two or more separate controllers or processors. For example, one controller may be used to control the operation of the applicator 132, and thereby control the precise rate and location of the application of the cross-linking agent 130 to the cornea 2. Another controller may be used to control the operation of the optical elements 112, and thereby control with precision the delivery of the light source 110 (i.e. the initiating element) to the cornea 2 by controlling any combination of: wavelength, bandwidth, intensity, power, location, depth of penetration, and duration of treatment. In addition, the function of the controller 120 can be partially or wholly replaced by a manual operation. For example, the applicator 132 can be manually operated to deliver the cross-linking agent 130 to the cornea 2 without the assistance of the controller 120. In addition, the controller 120 can operate the applicator 132 and the optical elements 112 according to inputs dynamically supplied by an operator of the delivery system 100 in real time, or can operate according to a pre-programmed sequence or routine.

Figure 2A:
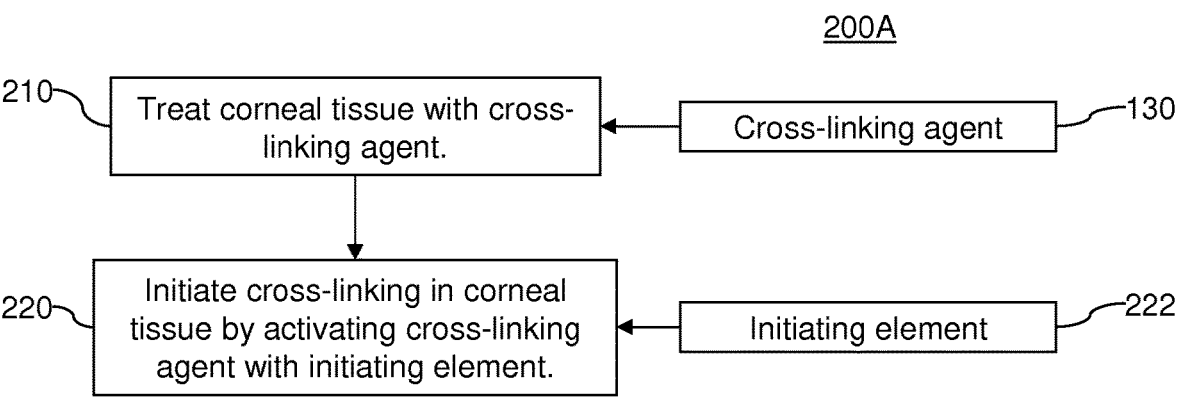
FIG. 2A provides a flowchart showing an example embodiment according to aspects of the present disclosure for activating cross-linking within cornea tissue using a cross-linking agent and an initiating element.

Referring to FIG. 2A, an example embodiment 200A according to aspects of the present disclosure is illustrated. Specifically, in step 210, the corneal tissue is treated with the cross-linking agent 130. Step 210 may occur, for example, after a treatment is applied to generate structural changes in the cornea and produce a desired shape change. Alternatively, step 210 may occur, for example, after it has been determined that the corneal tissue requires stabilization or strengthening. The cross-linking agent 130 is then activated in step 220 with an initiating element 222. In an example configuration, the initiating element 222 may be the light source 110 shown in FIG. 1. Activation of the cross-linking agent 130, for example, may be triggered thermally by the application of microwaves or light.

Figure 2B:
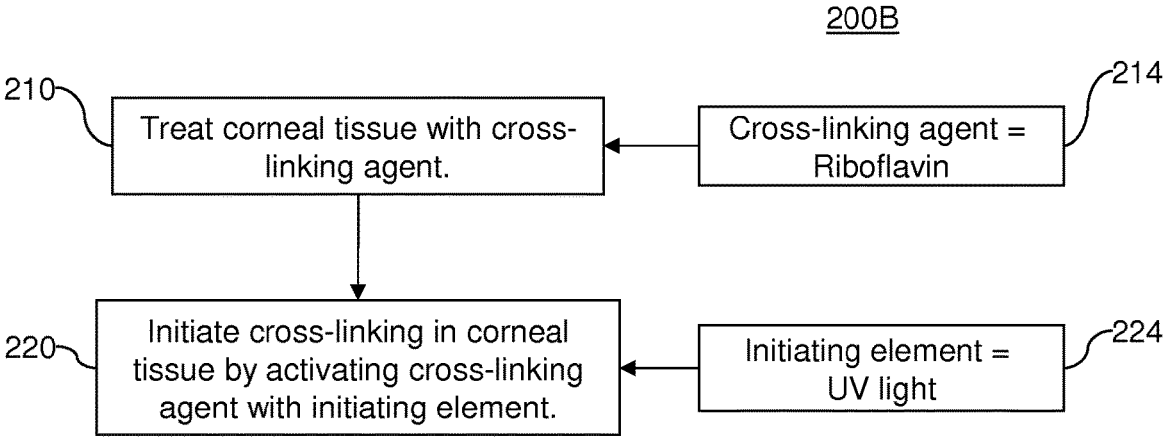
FIG. 2B provides a flowchart similar to FIG. 2A where Riboflavin may be applied topically as the cross-linking agent and UV light may be applied as the initiating element.

As the example embodiment 200B of FIG. 2B shows further, Riboflavin may be applied topically as a cross-linking agent 214 to the corneal tissue in step 210. As also shown in FIG. 2B, ultraviolet (UV) light may be applied as an initiating element 224 in step 220 to initiate cross-linking in the corneal areas treated with Riboflavin. Specifically, the UV light initiates cross-linking activity by causing the applied Riboflavin to release reactive oxygen radicals in the corneal tissue. In particular, the Riboflavin acts as a sensitizer to convert $O_2$ into singlet oxygen which causes cross-linking within the corneal tissue.

According to one approach, the Riboflavin may be applied topically to the corneal surface, and transepithelial delivery allows the Riboflavin to be applied to the corneal stroma. In general, the application of the cross-linking agent sufficiently introduces Riboflavin to mid-depth regions of the corneal tissue where stronger and more stable structure is desired.

Where the initiating element is UV light, the UV light may be generally applied to the corneal surface 2A (e.g. the epithelium) of the cornea 2 to activate cross-linking. However, regions of the cornea 2 requiring stabilization may extend from the corneal surface 2A to a mid-depth region 2B in the corneal stroma 2C. Generally applying UV light to the corneal surface 2A may not allow sufficient penetration of the UV light to activate necessary cross-linking at a mid-depth region of the cornea. Accordingly, embodiments according to aspects of the present disclosure provide a delivery system that accurately and precisely delivers UV light to the mid-depth region 2B where stronger and more stable corneal structure is required. In particular, treatment may generate desired changes in corneal structure at the mid-depth region 2B.

Figure 3:
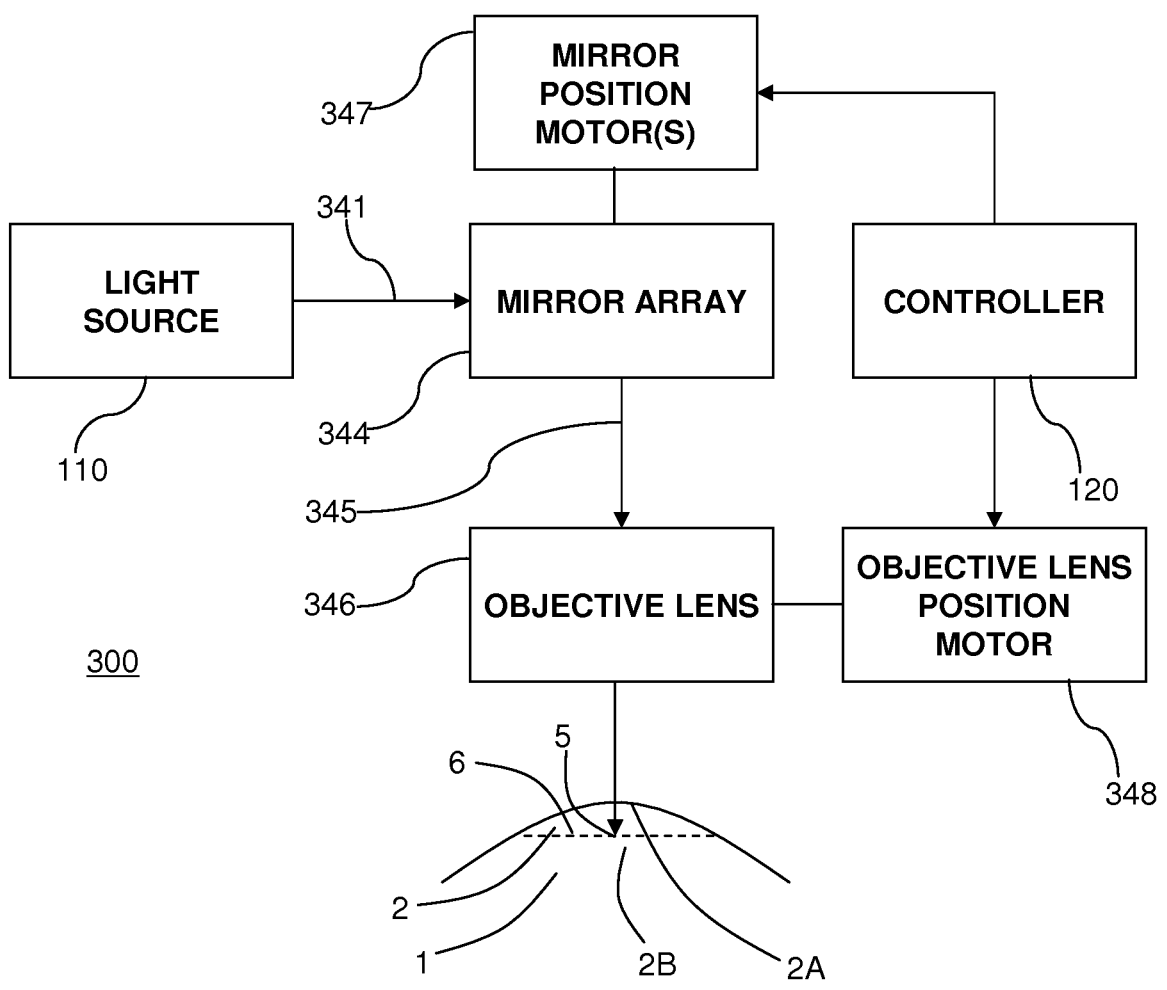
FIG. 3 provides an example delivery system for delivering light to the cornea 2 employing laser scanning technology.

FIG. 3 provides an example delivery system adapted as a laser scanning device 300 for delivering light to the cornea 2 employing laser scanning technology. The laser scanning device 300 has the light source 110 for delivering a laser beam through an objective lens 346 into a small focal volume within the cornea 2. The laser scanning device 300 also includes the controller 120 for controlling the intensity profile of the light delivered to the cornea 2 using a mirror array 344 and for controlling the focal plane of the objective lens 346. The light source 110 can be an ultraviolet (UV)

light source that emits a UV laser. A beam of light 341 is emitted from the light source 110 (e.g., UV laser) and passes to the mirror array 344. Within the mirror array 344, the beam of light 341 from the light source 110 is scanned over multiple mirrors adapted in an array. The beam of light 341 can be scanned over the mirrors in the mirror array 344 using, for example, one or more adjustable mirrors to direct the beam of light 341 to point at each mirror in turn. The beam of light 341 can be scanned over each mirror one at a time. Alternately, the beam of light 341 can be split into one or more additional beams of light using, for example, a beam splitter, and the resultant multiple beams of light can then be simultaneously scanned over multiple mirrors in the mirror array 344.

By rapidly scanning the beam of light 341 over the mirrors in the mirror array 344, the mirror array 344 outputs a light pattern 345, which has a two dimensional intensity pattern. The two dimensional intensity pattern of the light pattern 345 is generated by the mirror array 344 according to, for example, the length of time that the beam of light 341 is scanned over each mirror in the mirror array 344. In particular, the light pattern 345 can be considered a pixilated intensity pattern with each pixel represented by a mirror in the mirror array 344 and the intensity of the light in each pixel of the light pattern 345 proportionate to the length of time the beam of light 341 scans over the mirror in the mirror array 344 corresponding to each pixel. In an implementation where the beam of light 341 scans over each mirror in the mirror array 344 in turn to create the light pattern 345, the light pattern 345 is properly considered a time-averaged light pattern, as the output of the light pattern 345 at any one particular instant in time may constitute light from as few as a single pixel in the pixelated light pattern 345. In an implementation, the laser scanning technology of the delivery system 300 may be similar to the technology utilized by Digital Light Processing™ (DLP®) display technologies.

The mirror array 344 can include an array of small oscillating mirrors, controlled by mirror position motors 347. The mirror position motors 347 can be servo motors for causing the mirrors in the mirror array 344 to rotate so as to alternately reflect the beam of light 341 from the light source 340 toward the cornea 2. The controller 120 can control the light pattern 345 generated in the mirror array 344 using the mirror position motors 347. In addition, the controller 120 can control the depth within the cornea 2 that the light pattern 345 is focused to by controlling the location of the focal depth of the objective lens 346 relative to the corneal surface 2A. The controller can utilize an objective lens position motor 348 to raise and/or lower the objective lens 346 in order to adjust the focal plane 6 of the light pattern 345 emitted from the mirror array 344. By adjusting the focal plane 6 of the light pattern 345 using the objective lens motor 348, and controlling the two-dimensional intensity profile of the light pattern 345 using the mirror position motors 347, the controller 120 is adapted to control the delivery of the light source 110 to the cornea 2 in three dimensions. The three-dimensional pattern is generated by delivering the UV light to selected regions 5 on successive planes (parallel to the focal plane 6), which extend from the corneal surface 2A to the mid-depth region 2B within the corneal stroma. The cross-linking agent 130 introduced into the selected regions 5 is then activated as described above.

By scanning over selected regions 5 of a plane 6 at a particular depth within the cornea 2, the controller 120 can control the activation of the cross-linking agent 130 within the cornea 2 according to a three dimensional profile. In particular, the controller 120 can utilize the laser scanning technology of the laser scanning device 300 to strengthen and stiffen the corneal tissues by activating cross-linking in a three-dimensional pattern within the cornea 2. In an implementation, the objective lens 346 can be replaced by an optical train consisting of mirrors and/or lenses to properly focus the light pattern 345 emitted from the mirror array 344. Additionally, the objective lens motor 348 can be replaced by a motorized device for adjusting the position of the eye 1 relative to the objective lens 346, which can be fixed in space. For example, a chair or lift that makes fine motor step adjustments and adapted to hold a patient during eye treatment can be utilized to adjust the position of the eye 1 relative to the objective lens 346.

Advantageously, the use of laser scanning technologies allows cross-linking to be activated beyond the corneal surface 2A of the cornea 2, at depths where stronger and more stable corneal structure is desired, for example, where structural changes have been generated by an eye therapy treatment. In other words, the application of the initiating element (i.e., the light source 110) is applied precisely according to a selected three-dimensional pattern and is not limited to a two-dimensional area at the corneal surface 2A of the cornea 2.

Although the embodiments described herein may initiate cross-linking in the cornea according to an annular pattern defined, for example, by a thermokeratoplasty applicator, the initiation pattern in other embodiments is not limited to a particular shape. Indeed, energy may be applied to the cornea in non-annular patterns, so cross-linking may be initiated in areas of the cornea that correspond to the resulting non-annular changes in corneal structure. Examples of the non-annular shapes by which energy may be applied to the cornea are described in U.S. patent Ser. No. 12/113,672, filed on May 1, 2008, the contents of which are entirely incorporated herein by reference.

Some embodiments may employ Digital Micromirror Device (DMD) technology to modulate the application of initiating light, e.g., UV light, spatially as well as a temporally. Using DMD technology, a controlled light source projects the initiating light in a precise spatial pattern that is created by microscopically small mirrors laid out in a matrix on a semiconductor chip, known as a (DMD). Each mirror represents one or more pixels in the pattern of projected light. The power and duration at which the light is projected is determined as described elsewhere.

Embodiments may also employ aspects of multiphoton excitation microscopy. In particular, rather than delivering a single photon of a particular wavelength to the cornea 2, the delivery system (e.g., 100 in FIG. 1) delivers multiple photons of longer wavelengths, i.e., lower energy, that combine to initiate the cross-linking. Advantageously, longer wavelengths are scattered within the cornea 2 to a lesser degree than shorter wavelengths, which allows longer wavelengths of light to penetrate the cornea 2 more efficiently than shorter wavelength light. For example, in some embodiments, two photons may be employed, where each photon carries approximately half the energy necessary to excite the molecules in the cross-linking agent 130 that release oxygen radicals. When a cross-linking agent molecule simultaneously absorbs both photons, it absorbs enough energy to release reactive oxygen radicals in the corneal tissue. Embodiments may also utilize lower energy photons such that a cross-linking agent molecule must simultaneously absorb, for example, three, four, or five, photons to release a reactive oxygen radical. The probability of the near-simultaneous absorption of multiple photons is low, so a high flux of excitation photons may be required, and the high flux may be delivered through a femtosecond laser. Because multiple photons are absorbed for activation of the cross-linking agent molecule, the probability for activation increases with intensity. Therefore, more activation occurs where the delivery of light from the light source 110 is tightly focused compared to where it is more diffuse. The light source 110 may deliver a laser beam to the cornea 2. Effectively, activation of the cross-linking agent 330 is restricted to the smaller focal volume where the light source 310 is delivered to the cornea 2 with a high flux. This localization advantageously allows for more precise control over where cross-linking is activated within the cornea 2.

Referring again to FIG. 1, embodiments employing multiphoton excitation microscopy can also optionally employ multiple beams of light simultaneously applied to the cornea 2 by the light source 110. For example, a first and a second beam of light can each be directed from the optical elements 112 to an overlapping region of the cornea 2. The region of intersection of the two beams of light can be a volume in the cornea 2 where cross-linking is desired to occur. Multiple beams of light can be delivered to the cornea 2 using aspects of the optical elements 112 to split a beam of light emitted from the light source 310 and direct the resulting multiple beams of light to an overlapping region of the cornea 2. In addition, embodiments employing multiphoton excitation microscopy can employ multiple light sources, each emitting a beam of light that is directed to the cornea 2, such that the multiple resulting beams of light overlap or intersect in a volume of the cornea 2 where cross-linking is desired to occur. The region of intersection may be, for example, in the mid-depth region 2B of the cornea 2, and may be below the corneal surface 2A. Aspects of the present disclosure employing overlapping beams of light to achieve multiphoton microscopy may provide an additional approach to controlling the activation of the cross-linking agent 130 according to a three-dimensional profile within the cornea 2.

Aspects of the present disclosure, e.g., adjusting the parameters for delivery and activation of the cross-linking agent, can be employed to reduce the amount of time required to achieve the desired cross-linking. In an example implementation, the time can be reduced from minutes to seconds. While some configurations may apply the initiating element (i.e., the light source 110) at a flux dose of 5 J/cm$^2$, aspects of the present disclosure allow larger doses of the initiating element, e.g., multiples of 5 J/cm$^2$, to be applied to reduce the time required to achieve the desired cross-linking. Highly accelerated cross-linking is particularly possible when using laser scanning technologies (such as in the delivery system 300 provided in FIG. 3) in combination with a feedback system 400 as shown in FIG. 4, such as a rapid video eye-tracking system, described below.

To decrease the treatment time, and advantageously generate stronger cross-linking within the cornea 2, the initiating element (e.g., the light source 110 shown in FIG. 1) may be applied with a power between 30 mW and 1 W. The total dose of energy absorbed in the cornea 2 can be described as an effective dose, which is an amount of energy absorbed through a region of the corneal surface 2A. For example the effective dose for a region of the cornea 2 can be, for example, 5 J/cm$^2$, or as high as 20 J/cm$^2$ or 30 J/cm$^2$. The effective dose delivering the energy flux just described can be delivered from a single application of energy, or from repeated applications of energy. In an example implementation where repeated applications of energy are employed to deliver an effective dose to a region of the cornea 2, each subsequent application of energy can be identical, or can be different according to information provided by the feedback system 400.

Treatment of the cornea 2 by activating cross-linking produces structural changes to the corneal stroma. In general, the optomechanical properties of the cornea changes under stress. Such changes include: straightening out the waviness of the collagen fibrils; slippage and rotation of individual lamellae; and breakdown of aggregated molecular superstructures into smaller units. In such cases, the application of the cross-linking agent 130 introduces sufficient amounts of cross-linking agent to mid-depth regions 2B of the corneal tissue where stronger and more stable structure is desired. The cross-linking agent 130 may be applied directly to corneal tissue that have received an eye therapy treatment and/or in areas around the treated tissue.

Figure 4:
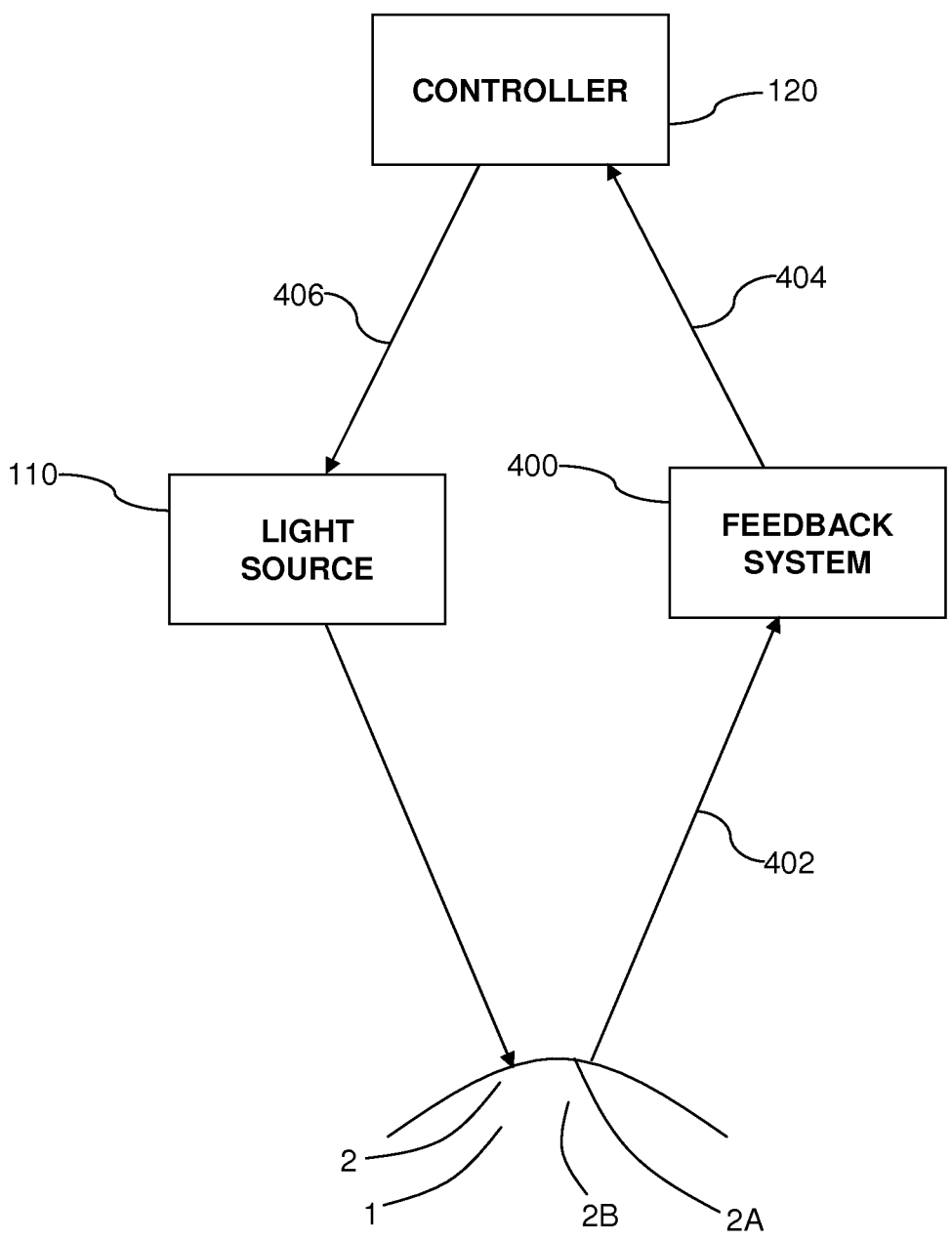
FIG. 4 illustrates a delivery system incorporating a feedback system.

To enhance safety and efficacy of the application and the activation of the cross-linking agent, aspects of the present disclosure provide techniques for real time monitoring of the changes to the collagen fibrils with a feedback system 400 shown in FIG. 4. These techniques may be employed to confirm whether appropriate doses of the cross-linking agent 130 have been applied during treatment and/or to determine whether the cross-linking agent 130 has been sufficiently activated by the initiating element (e.g., the light source 110). General studies relating to dosage may also apply these monitoring techniques.

Moreover, real time monitoring with the feedback system 400 may be employed to identify when further application of the initiating element (e.g., the light source 110) yields no additional cross-linking. Where the initiating element is UV light, determining an end point for the application of the initiating element protects the corneal tissue from unnecessary exposure to UV light. Accordingly, the safety of the cross-linking treatment is enhanced. The controller 120 for the cross-linking delivery system can automatically cease further application of UV light when the real time monitoring from the feedback system 400 determines that no additional cross-linking is occurring.

FIG. 4 illustrates a delivery system incorporating the feedback system 400. The feedback system 400 is adapted to gather measurements 402 from the eye 1, and pass feedback information 404 to the controller 120. The measurements 402 can be indicative of the progress of strengthening and stabilizing the corneal tissue. The measurements 402 can also provide position information regarding the location of the eye and can detect movement of the cornea 2, and particularly the regions of the corneal tissue requiring stabilization. The feedback information 404 is based on the measurements 402 and provides input to the controller 120. The controller 120 then analyzes the feedback information 404 to determine how to adjust the application of the initiating element, e.g., the light source 110, and sends command signals 406 to the light source 110 accordingly. Furthermore, the delivery system 100 shown in FIG. 1 can be adapted to incorporate the feedback system 100 and can adjust any combination of the optical elements 112, the applicator 132, or the light source 110 in order to control the activation of the cross-linking agent 130 within the cornea 2 based on the feedback information 404 received from the feedback system 400.

Figures 5A, 5B:
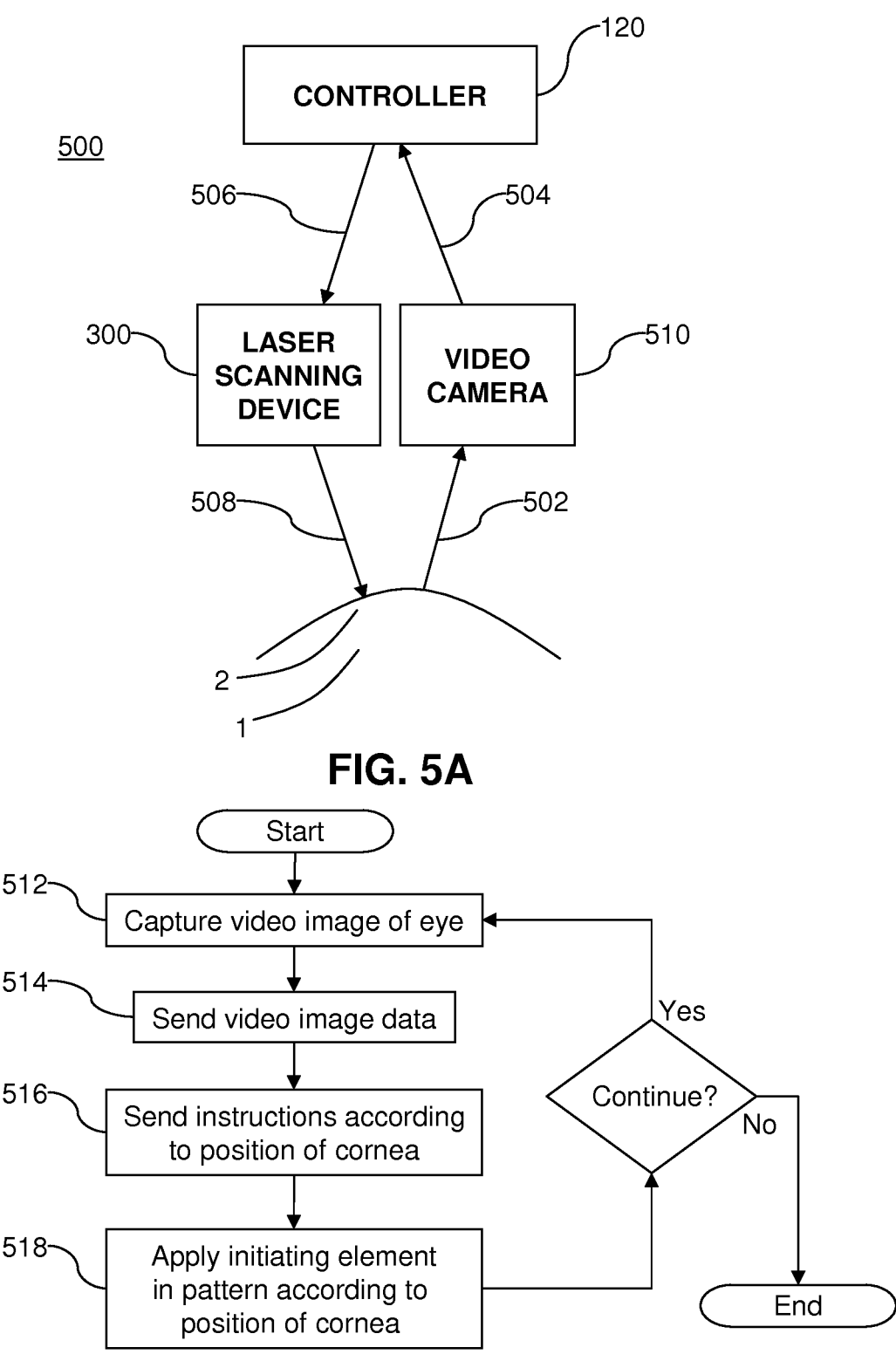
FIG. 5A illustrates a delivery system for activating cross-linking in the cornea with the laser scanning device and having a video camera feedback system.
FIG. 5B illustrates an exemplary operation of the delivery system shown in FIG. 5A.

The feedback system 400 can be a video eye-tracking system as shown in FIG. 5A, which illustrates a delivery system 500 for activating cross-linking in the cornea 2 with the laser scanning device 300. The delivery system 500 of FIG. 5A includes a video camera 510 for capturing digital video image data 504 of the eye 1. The video camera 510 generates the video image data 504 of the eye 1 in real time and tracks any movement of the eye 1. The video image data 504 generated by the video camera 510 is indicative of photons 502 reflected from the eye 1. The photons 502 can be reflected from the eye 1 from an ambient light source, or can be reflected from the eye 1 by a light source that is incorporated into the delivery system 500 adapted to direct light to the eye 1 for reflecting back to the video camera 510. Delivery systems including the light source can optionally be adapted with the light source controlled by the controller 120. The delivery system 500 may minimize movement of the eye 1 by minimizing movement of the head, such as, for example, by use of a bite plate described below. However, the eye 1 can still move in the socket, relative to the head.

The real time video image data 504 (e.g., the series of images captured by the video camera 510) are sent to the controller 120, which may include processing hardware, such as a conventional personal computer or the like. The controller 120 analyzes the data from the video camera 10, for example, according to programmed instructions on computer-readable storage media, e.g., data storage hardware. In particular, the controller 120 identifies the image of the cornea 2 in the video image data 504 and determines the position of the cornea 2 relative to the delivery system 500, and particularly relative to the laser scanning device 300. The controller 120 sends instructions 506 to the laser scanning device 300 to direct a pattern of UV light 508 to the position of the cornea 2. For example, the instructions 506 can adjust optical aspects of the laser scanning device 300 to center the pattern of UV light 508 output from the laser scanning device 300 on the cornea 2. The pattern of UV light 508 activates the cross-linking agent 130 in desired areas and depths of corneal tissue according to aspects of the present disclosure described herein.

In addition, the video image data 504 can optionally include distance information and the controller 130 can be adapted to further analyze the video image data 504 to determine the distance to the cornea 2 from the laser scanning device 508 and can adjust the focal plane of the pattern of UV light 508 directed to the cornea 2. For example, the distance to the cornea 2 may be detected according to an auto-focus scheme that automatically determines the focal plane of the cornea 2, or may be determined according to an active ranging scheme, such as a laser ranging or radar scheme. In an implementation, the video image data 504 can be a series of images, and the controller 120 can be adapted to analyze the images in the series of images individually or in combination to detect, for example, trends in the movement of the cornea 2 in order to predict the location of the cornea 2 at a future time.

FIG. 5B illustrates an exemplary operation of the delivery system 500 shown in FIG. 5A. In step 512, the video camera 510 captures the video image data 504 of the eye 1 based on the photons 502 reflected from the eye 1. In step 514, the video image data 504 is sent to the controller 120. In step 516, the controller 120 sends the instructions 506 to the laser scanning device 300 according to the detected position of the cornea 2. In step 518, the initiating element (e.g., UV light) is applied to the cornea 2 according to the detected position of the cornea 2. Following step 518, a decision is made whether to continue to gather feedback data using the video monitoring system. If feedback data continues to be desired, the exemplary operation returns to step 512 and repeats until it is determined that feedback information is no longer required, at which point the exemplary operation ceases. In an implementation, the delivery system 500 can be adapted to operate according to the steps illustrated in FIG. 5B in real time, and can provide position data about the location of the cornea 2 continuously, or in response to queries from, for example, the controller 120.

In general, the system 500 shown in FIG. 5A can correlate pixels of the video camera 510 with the pixels of the laser scanning device 300, so the real time video image date 504 from the video camera 120 can be employed to direct the pattern of UV light 508 from the laser scanning device 300 accurately to the desired corneal tissue even if there is some movement by the eye 1. The system 500 can be employed to map, associate, and/or correlate pixels in the video camera 510 with pixels in the laser scanning device 300. Advantageously, the system 500 does not require mechanical tracking of the eye 1 and mechanical adjustment (of the laser scanning device 300) to apply the pattern of UV light 508 accurately to the cornea 2.

In sum, implementations of aspects of the present disclosure stabilize a three-dimensional structure of corneal tissue through controlled application and activation of cross-linking in the corneal tissue. For example, the cross-linking agent 130 and/or the initiating element (e.g., the pattern of UV light 508) are applied in a series of timed and controlled steps to activate cross-linking incrementally. Moreover, the delivery and activation of the cross-linking agent 130 at depths in the cornea 2 depend on the concentration(s) and diffusion times of the cross-linking agent 130 as well as the power(s) and bandwidths of the initiating element. Furthermore, systems may employ laser scanning technologies in combination with a video eye-tracking system to achieve accurate application of the initiating element 222 to the cornea 2.

Another technique for real time monitoring of the cornea 2 during cross-linking treatment employs interferometry with a specialized phasecam interferometer (e.g., manufactured by 4dTechnology, Tucson, AZ). The interferometer takes up to 25 frames per second with a very short exposure so as to substantially minimize motion during an exposure duration. In an example, the exposure time can be less than one millisecond. As the heart beats, the intraocular pressure (IOP) in the eye 1 increases and causes the corneal surface to extend outwardly by a slight amount. The deflection of the cornea 2 is determined by developing a difference map between the peaks and valleys of the cardiac pulsate flow cycles. The deflection of the cornea provides an indicator for the strength of the corneal tissue. The deflection of the cornea 2 may be used to measure changes in the biomechanical strength, rigidity, and/or stiffness during cross-linking treatment. Additionally, comparisons of an amount of deflection observed before and after cross-linking treatment is applied to a cornea 2 may be used to determine a change in biomechanical strength, rigidity, and/or stiffness of the corneal tissue. In general, however, interferometry may be employed to measure corneal strength before and after an eye surgery, before and after any eye treatment, or to monitor disease states. Thus, aspects of the present disclosure employ interferometry as a non-contact technique to determine the surface shape of the cornea 2 and develop a difference map to measure the deflection from IOP. The deflection of the cornea can then be used to determine changes in corneal strength during cross-linking treatment.

To provide control over cross-linking activity, aspects of the present disclosure provide techniques for real time monitoring of the changes in the strength of the corneal tissue. These techniques may be employed to confirm whether appropriate doses of the cross-linking agent have been applied during treatment. Moreover, real time monitoring may be employed to identify when further application of the initiating element yields no additional cross-linking. Where the initiating element is UV light, determining an end point for the application of the initiating element protects the corneal tissue from unnecessary exposure to UV light. Accordingly, the safety of the cross-linking treatment is enhanced. The controller 120 for the cross-linking delivery system (e.g., the delivery system 100 in FIG. 1) can automatically cease further application of UV light when the real time monitoring determines that no additional cross-linking is occurring.

Figures 6A, 6B, 6C:
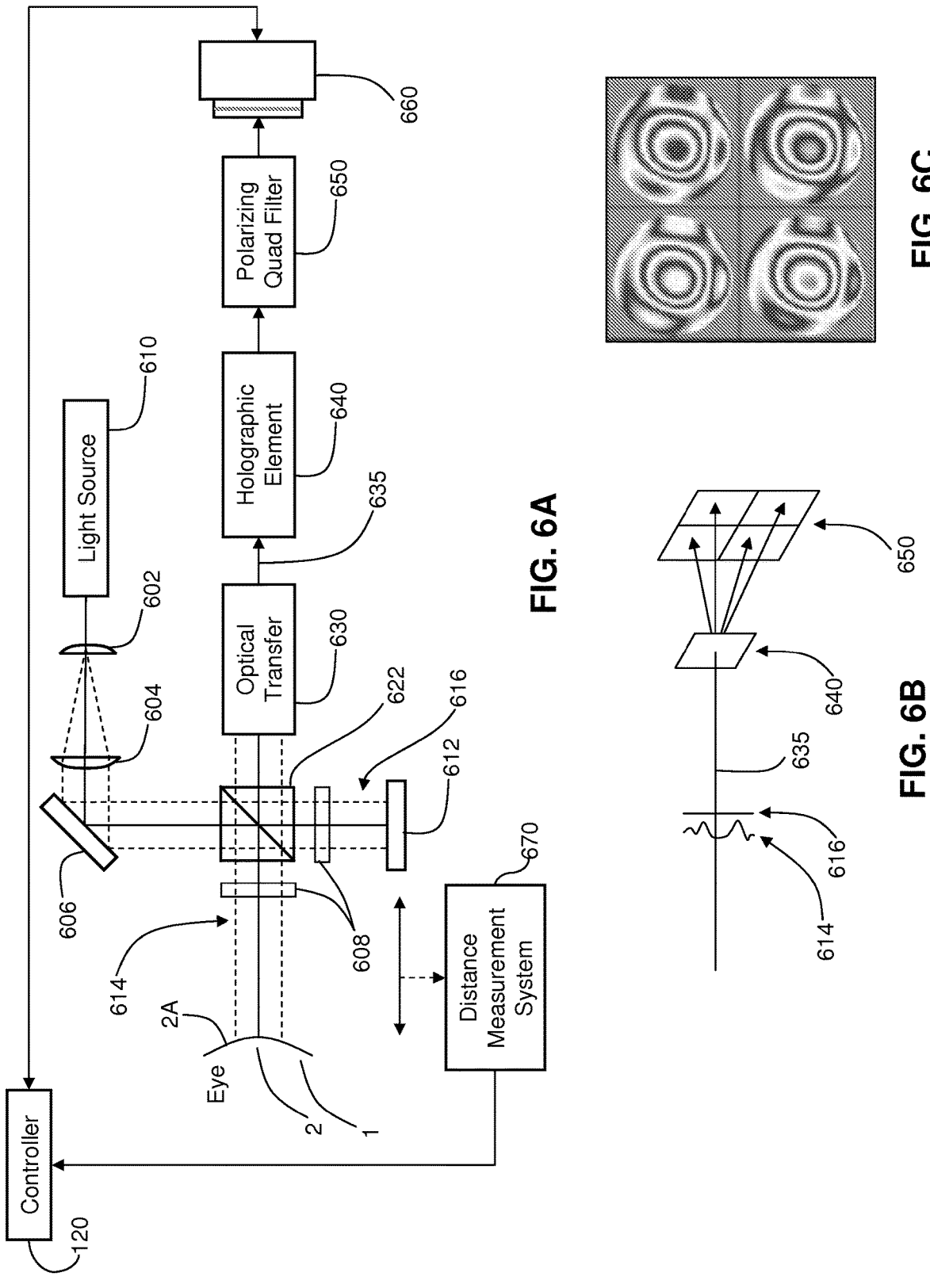
FIG. 6A illustrates a phase-shifting interferometer feedback system adapted to measures the surface shape of the cornea by comparing a reference beam reflected from a reference mirror and a signal beam reflected from the corneal surface.
FIG. 6B symbolically illustrates the operation of the holographic element and the polarizing mask included in the interferometer configuration shown in FIG. 6A.
FIG. 6C provides an exemplary interference pattern (i.e., interferogram), which is the intensity pattern detected by the CCD detector.

FIG. 6A illustrates a phase-shifting interferometer adapted to measure the surface shape of the cornea 2 by comparing a reference beam 616 (i.e., reference wavefront) reflected from a reference mirror 612 and a signal beam 614 (i.e., signal wavefront) reflected from the corneal surface 2A. Interferometry involves the analysis of an interference pattern created by the superposition of two or more waves. The interferometer illustrated in FIG. 6A is adapted as a Twyman-Green interferometer and is adapted to record the interference pattern, i.e., interferogram, of the superposition of the reference beam 616 and the signal beam 614 using a CCD detector 660 such as a camera. Although, the CCD detector 660 may be replaced by any photosensitive sensor suitable for converting an optical intensity sensed at an array of pixel locations to an electrical charge or current. The interferometer shown in FIG. 6A includes a light source 610, a spreading lens 602, a converging lens 604, an angled mirror 606, a polarizing beam splitter (PBS) 622, and a reference mirror 612. The interferometer also includes two quarter wave plates 608. The quarter-wave plates 608 can be created, at least in part, from a birefringent material that causes beams of light passing through the quarter-wave plates 608 to rotate the polarization of light of the beam of light. In particular, the quarter wave plate 608 can cause an incoming beam of light having a polarization that is a combination of two orthogonal components, to result in an outgoing beam of light where one of the two orthogonal polarization components is phase-delayed relative to the other by one-quarter wavelength. In a configuration, the quarter-wave plates 608 can convert linearly polarized light to circularly polarized light. The interferometer also has an optical transfer 630, which can include a combination of lenses, filters, and mirrors to focus, align, and direct a superimposed beam 635 to a holographic element 640. The superimposed beam 635 is a superposition of the signal beam 614 and the reference beam 616. The holographic element 640 can split the superimposed beam 635 into four copies for being applied to a polarizing quad filter 650. The output of the polarizing quad filter 650 is then recorded by the CCD detector 660. The resulting image or intensity pattern captured by the CCD detector 660 is then sent to the controller 120 for analysis. The controller 120 can also receive an input from a distance measurement system 670 adapted to monitor a distance between the eye 1 and aspects of the interferometer. Additional optical elements may be included at various locations within the optical path of the interferometer to spread and/or focus the beams of light.

In an exemplary operation of the interferometer illustrated in FIG. 6A, a beam of light is emitted from the light source 610. The beam of light is then spread and collimated with the lenses 602, 604 such as is appropriate for directing the beam toward the polarizing beam splitter 622. The spread beam is then reflected on the mirror 606 and directed toward the polarizing beam splitter 622. A half-wave plate or other suitable birefringent material or polarizing filter may be inserted in the optical path between the light source 610 and the polarizing beam splitter (PBS) 622 to cause the beam of light directed to the PBS 622 to have an appropriate polarization angle relative to the PBS to allow a desired amount of light having orthogonal polarizations to be transmitted and reflected by the PBS 622. For example, the polarization of the incoming beam of light can be selected such that the PBS 622 allows roughly equal amounts of light to be reflected and transmitted, with each having orthogonal linear polarization.

Upon reaching the PBS 622, the beam of light is divided according to the polarization of the incoming beam of light, with roughly half directed toward the eye 1 to be reflected by the corneal surface 2A of the cornea 2. The other half, which may be orthogonally polarized relative to the beam directed toward the eye 1, is directed toward the reference mirror 612. The light reflected from the corneal surface 2A is the signal beam 614. The light reflected from the reference mirror 612 is the reference beam 616. Each of the beams emitted from the PBS 622 is passed through one of the quarter wave plates 608, which rotates the signal beam 614 and the reference beam 616 after reflection while retaining their mutual orthogonal linear polarization states. The configuration of the PBS 622 along with the quarter wave plates 608 allows the reference beam 616 and the signal beam 614 to be transmitted through and reflected from the PBS 622 toward the optical transfer 630 along a common optical path. Additional lenses may be used between the PBS 622 and the eye 1 or between the PBS 622 and the test mirror 612 in order to appropriately spread or narrow the beam of light to simultaneously illuminate the entire area of the eye 1 (or the reference mirror 612) to be measured, and to return substantially collimated beams (e.g., the reference beam 616 and the signal beam 614) back to the PBS 622.

The light source 610 may emit a linearly polarized beam of light, or may emit a beam of light which is then filtered to pass a linearly polarized beam of light. The wavelength of the light emitted from the light source 610 may be chosen to be suitable for the various optical components in the interferometer and for the CCD detector 660. In addition, the wavelength of the light source 610 may be chosen to be a wavelength of light that is safe for being reflected from the corneal surface 2A of the eye 1. Generally, the reference mirror 616 can be any reference surface suitable for reflecting light, and can optionally have a flat configuration or can have a curved configuration. In particular, the reference mirror 616 may be shaped according to a desired shape of the corneal surface 2A of the cornea 2, or may be shaped according to a typical shape of a corneal surface, and may be an aspheric surface. In an example where the reference mirror 616 is shaped as an ideal or typical corneal surface, the interference pattern displayed on the interferogram reveals the differences between the signal beam 614 (i.e., signal wavefront) reflected from the corneal surface 2A of the eye 1 and the reference beam 616 (i.e., reference wavefront) reflected from the ideal or typical or corneal surface. Implementations utilizing a curved surface as the reference surface can incorporate a converging lens to direct the beam to the reference surface. In an implementation where the reference surface is a convex surface, the converging lens is positioned such that the reference surface is closer to the converging lens than the focus of the converging lens; however, where the reference surface is a concave surface, the converging lens is positioned such that the reference surface is further from the converging lens than the focus of the converging lens.

The light directed toward the optical transfer 630 is a superposition of the reference beam 616 and the signal beam 614, which may be orthogonally polarized relative to one another. In particular, the reference beam 616 and the signal beam 614 can be orthogonally circularly polarized relative to one another. The optical transfer 630 may include a combination of lenses, mirrors, and apertures to relay the superimposed beam 635 onto the holographic element 640. The aperture (not separately shown), which can be incorporated in the optical transfer 630, can be chosen such that the diffraction-limited spot size at the CCD detector 660 is approximately 2 effective pixels in diameter in order to avoid aliasing of the interference pattern spatial frequency. An appropriate selection of the aperture ensures that spatial frequencies higher than the pixel spacing of the CCD detector 660 are not present in the resulting interferograms measured by the CCD detector 660.

FIG. 6B symbolically illustrates the operation of the holographic element 640 and the polarizing quad filter 650 included in the interferometer configuration shown in FIG. 6A. With reference to FIGS. 6A and 6B, the superimposed beam 635, which is a superposition of the reference beam 616 and the signal beam 614 is directed toward the holographic element 640. The signal beam 614 is represented symbolically as having a wavefront delayed from the wavefront of the reference beam 616 by varying amounts. The signal beam 614 is shown with a curved line indicating exemplary amounts of delay relative to the reference beam 616 across a profile of the signal beam 614. The amount of delay between the signal beam 614 and the reference beam 616 corresponds to the difference in optical path length between the path taken by the reference beam 616 and the signal beam 614, and therefore corresponds to differences between the corneal surface 2A and the reference mirror 612.

FIG. 6C provides an exemplary interference pattern (i.e., interferogram), which is the intensity pattern (i.e., image) detected by the CCD detector 660 and output from the polarizing quad filter 650. In a configuration, the difference in optical path length between the signal beam 614 and the reference beam 616 may be revealed by the interference pattern (i.e., interferogram) recorded by the CCD detector, and allows for performing profilometry (i.e., measuring the absolute three-dimensional profile of a solid object) of the corneal surface 2A of the eye 1. The holographic element 640 splits the superposition beam 635 into four substantially identical copies and projects the four copies onto the polarizing quad filter 650. Additional optical elements may be employed to provide a collimated beam to the polarizing quad filter 650. The polarizing quad filter 650 is divided into four quadrants, with each quadrant introducing a different effective phase-delay between the reference and test wavefronts at each pixel. The phase mask may be constructed from a birefringent plate, or from four separate birefringent plates. Alternatively, the polarizing mask 640 may be constructed from an array of four polarizers, with each having a different polarizing angle.

The intensity of two beams having orthogonal circular polarization (e.g., the reference beam 616 and the signal beam 614) interfered by a polarizer with angle α is given by Eq. 1.

$$I(x, y) = \frac{1}{2}\left(Ir + Is + 2\sqrt{Ir \cdot Is}\cos(\Delta\theta(x, y) + 2\alpha)\right) \quad \text{(Eq. 1)}$$

In Eq. 1, Ir and Is are the intensities of the reference beam 616 and the signal beam 614, respectively and Δθ(x,y) is the phase shift between the reference beam 616 and the signal beam 614 due to the optical path difference for each pixel array coordinate. In an implementation, both Ir and Is can vary with x and y. So, by constructing the polarizing quad filter 650 with polarizers in each quadrant having angles of 0 degrees, 45 degrees, 90 degrees, and 135 degrees, the following transfer functions provide the intensity of light transmitted through each quadrant of the polarizing quad filter 650.

$$A(x, y) = \frac{1}{2}\left(Ir + Is + 2\sqrt{Ir \cdot Is}\cos(\Delta\theta(x, y))\right) \quad \text{(Eq. 2a)}$$

$$B(x, y) = \frac{1}{2}\left(Ir + Is + 2\sqrt{Ir \cdot Is}\cos\left(\Delta\theta(x, y) + \frac{\pi}{2}\right)\right) \quad \text{(Eq. 2b)}$$

$$C(x, y) = \frac{1}{2}\left(Ir + Is + 2\sqrt{Ir \cdot Is}\cos(\Delta\theta(x, y) + \pi)\right) \quad \text{(Eq. 2c)}$$

$$D(x, y) = \frac{1}{2}\left(Ir + Is + 2\sqrt{Ir \cdot Is}\cos\left(\Delta\theta(x, y) + \frac{3\pi}{2}\right)\right) \quad \text{(Eq. 2d)}$$

The transfer functions provided in Eqs. 2a through 2d provide the intensities measured at each pixel coordinate for the light transmitted through the polarizing quad filter 650. Eq. 2a may provide the intensity of light passing through the first quadrant of the polarizing quad filter 650, which has a polarizing angle of 0 degrees relative to the x, y orientation of the pixel array. The first quadrant of the polarizing quad filter 650 therefore interferes in-phase components of the signal beam 614 and the reference beam 616 present in the superimposed beam 635. Eq. 2b may provide the intensity of light passing through the second quadrant of the polarizing quad filter 650, which has a polarizing angle of 45 degrees relative to the x, y orientation of the pixel array. The second quadrant of the polarizing quad filter 650 therefore interferes in-phase quadrature components of the signal beam 614 and the reference beam 616. Eq. 2c may provide the intensity of light passing through the third quadrature of the polarizing quad filter 650, which has a polarizing angle of 90 degrees relative to the x, y orientation of the pixel array. The third quadrant of the polarizing quad filter 650 therefore interferes out-of-phase components of the signal beam 614 and the reference beam 616. Eq. 2d may provide the intensity of light passing through the fourth quadrature of the polarizing quad filter 650, which has a polarizing angle of 135 degrees relative to the x, y orientation of the pixel array. The fourth quadrant of the polarizing quad filter 650 therefore interferes out-of-phase quadrature components of the signal beam 614 and the reference beam 616.

Using the interference pattern detected by the CCD detector 660, methods can be employed to calculate the phase difference and modulation index to reveal the optical path difference between the reference beam 616 and the signal beam 614, and thereby perform profilometry of the corneal surface 2A of the eye 1. The transfer functions of Eqs 2a through 2d may be used to compute the phase difference between the signal beam 614 and the reference beam 616 at each x, y location according to a four-bucket algorithm, e.g.:

$$\Delta\theta(x, y) = \arctan\left(\frac{C(x, y) - A(x, y)}{D(x, y) - B(x, y)}\right) \quad \text{(Eq. 3)}$$

Eqs. 2 and 3 provide an example algorithm for computing a phase difference map for a single exposure of the CCD detector 660. Alternatively, the phase difference at each spatial coordinate can be computed according to a windowed convolution algorithm. A windowed convolution algorithm may provide less phase-dependent error, although the spatial frequency is at least partially filtered by the convolution process and may therefore have reduced spatial frequency. In addition, implementations utilizing a convolution algorithm to provide real time phase difference maps may require additional computational resources.

Alternatively, an interferometer may be employed with implementations of the present disclosure to perform profilometry of the eye 1 by gathering the four interference patterns without the holographic element and without simultaneously capturing the four interferograms with a single exposure. Such an interferometer may utilize a configuration which changes the polarizing mask following each exposure of the CCD detector 660 such that four subsequent exposures provide interference patterns for each polarizing angle and allow for computing the phase difference map according to Eqs. 2 and 3.

Systems implementing algorithms for computing a profile of the corneal surface 2A of the eye 1 from the phase difference map may also take as an input a distance between the corneal surface 2A and the interferometer (which can be provided, for example, by the distance measurement system 670). The distance monitored by the distance measurement system 670 can be used to determine a scaling of the intensity patterns captured by the CCD detector 660 and to determine a radius of curvature of the cornea 2, and thus the optical power of the eye 1. The distance measurement system 670 may be implemented by two cameras focusing on the cornea 2, but oriented at an angle relative to one another, and separated by a known distance, such that the angle between the orientations of the two cameras when both are focused on the cornea 2 provides an estimation of the distance according to standard trigonometric analysis. The distance measurement system 670 may be implemented as a high resolution camera capturing images from a known position. The high resolution camera may be oriented at approximately 90° to the optical axis of the eye 1, such that the edge of the eye 1 can be mapped to a pixel location of the high resolution camera, which corresponds to a distance from the interferometer. The distance measurement system 670 may be implemented as a separate interferometer, such as a Michelson interferometer. In addition, the distance measurement system 670 may be adapted as an active ranging technique which uses reflected signals correlated with reference signals to measure time delays, such as a doppler, ultrasound, or optical ranging system. Additionally, the distance measurement system 670 may be implemented by a configuration having multiple slit lamps, such as the configuration illustrated by FIG. 8A, which is described below in further detail. As shown in FIG. 6A, the distance measurement system 670 is adapted to provide an output indicative of the monitored distance to the controller 120. The distance measurement system 670 can be a system integrated with the interferometer or can be implemented as a separate from the interferometer and is adapted to provide an input to the algorithms for performing corneal topography. In some aspects, the output of the distance measurement system 670 may be considered a monitored distance, an estimated distance, or a measured distance, and may be used interchangeably.

The above-described algorithms can be performed automatically by the controller 120 or by one or more separate computers adapted to receive the intensity patterns captured by the CCD detector 660 and the monitored distance from the distance measurement system 670.

To be useful for performing profilometry of the cornea surface 2A, the fringes in the interference pattern (i.e., the interferograms) produced by the phase-shifting interferometer must be sufficiently stable in the image plane to measure the surface shape of the cornea 2. Due to changes, for example, in saccadic eye movement and eye fixation, the corneal surface 2A changes periodically and may not remain sufficiently stable for conventional phase-shifting interferometers. As such, the phase-shifting interferometer in the present embodiments shortens the data acquisition time to reduce the amount of relative motion and effectively freeze the fringe image (i.e., the interferograms) during measurement.

In particular, rapid data acquisition can be achieved by dynamic interferometry. Dynamic interferometry in the present implementations uses polarization to generate the required phase shift and captures multiple fringe images on a single camera to acquire the data. Dynamic interferometers can make single-frame phase measurements with short exposures while capturing the phase changes. Moreover, signal averaging can be advantageously employed with dynamic interferometry, e.g., to reduce systematic errors.

Advantageously, using the holographic element 640 allows for the interference patterns corresponding to each of the four polarizing angles to be detected simultaneously with a single exposure of the CCD detector 660. Simultaneous detection of the interferograms with a single exposure of the CCD detector 660 offers significant immunity to vibration, which may occur between separate exposures. Simultaneous detection also allows for capturing the profile of the corneal surface 2A during an duration of time that does not exceed the duration of the exposure of the CCD detector 660. In an example, the duration of the exposure of the CCD detector 660 can be less than one millisecond and can be as low as thirty microseconds.

Figures 6D, 6E:
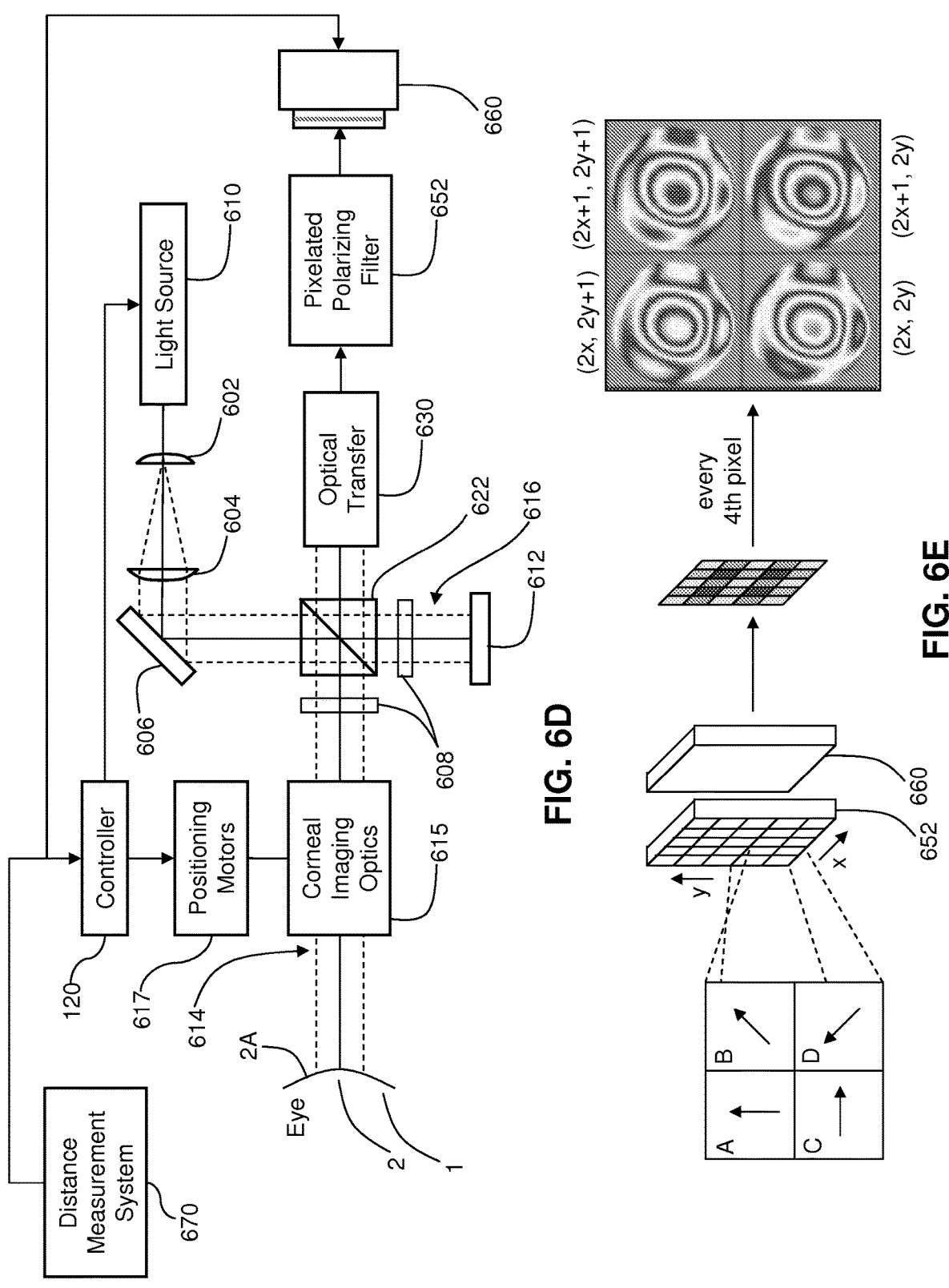
FIG. 6D provides an alternative configuration of an interferometer for performing profilometry of the corneal surface and providing feedback.
FIG. 6E provides a symbolic representation of aspects of the pixelated polarizing mask in the interferometer shown in FIG. 6D.

FIG. 6D provides an alternative configuration of an interferometer for performing profilometry of the corneal surface 2A. The interferometer in FIG. 6D is similar in some respects to the interferometer shown in FIG. 6A, with the principal difference that the holographic element 640 and polarizing quad filter 650 as shown in FIG. 6B are replaced with a pixelated polarizing filter 652. The interferometer shown in FIG. 6D also includes cornea imaging optics 615 between the PBS 622 and the eye 1 for spreading, diffusing, focusing, and/or collimating the light directed to and reflected from the eye 1. In particular, the cornea imaging optics 615 can include a lens or combination of lenses for causing the beam from the PBS 622 to converges to meet the radius of curvature of the cornea 2, and then collimate the signal beam 614 after it is reflected from the corneal surface 2A. The cornea imaging optics 615 can also be employed in connection with the interferometer configuration illustrated in FIG. 6A.

Further illustrated in FIG. 6D are positioning motors 617 for adjusting the corneal imaging optics 615. The positioning motors 617 may include a single motor or multiple motors for manipulating a position of one or more aspects of the corneal imaging optics 615 according to input signals from the controller 120. For example, the positioning motors 617 may include a first and second motor for manipulating the position of a convergent lens most proximate the cornea 2 according to input signals from the controller 120. The positioning motors may be adapted to adjust the position of the convergent lens in directions wholly or partially perpendicular to the orientation of the signal beam 614, or in a direction parallel to the orientation of the signal beam 614. The positioning motors may incorporate piezo electric crystals for making fine adjustments. The controller 120 may be further adapted to adjust the position of the corneal imaging optics 615 according to information received by the camera 660.

For example, the controller 120 may be adapted to determine a centroid position of the specular reflection of light emerging from the cornea 2. The centroid position may be determined by combining intensity information detected at adjacent pixels of the camera 660 in order to achieve an estimate of a centroid position with a greater precision than an estimate of an individual pixel. In an implementation, the centroid position may be determined at a rate of, for example 200 Hz, and the input signals may be sent to the positioning motors 617 at the same rate (i.e., 200 Hz). Alternatively, the controller 120 may incorporate a separate camera different from the camera 660 for measuring the centroid position of the specular reflection. To provide the positioning function, the camera 660 (or the separate camera) need only have a resolution of, for example, 16 pixels by 16 pixels. A relatively low resolution allows for processing of the image to determine the centroid position to occur more rapidly. Once an energy distribution of received intensities is detected by the camera 660, the controller may be adapted to operate the positioning motors 617 so as to maintain the initially observed energy distribution. Maintenance of the energy distribution may be achieved by manipulating the corneal imaging optics 615 in three dimensions.

Implementations tracking the position of the eye, and adjusting optical elements according to a monitored (or tracked) position may be further adapted to distinguish a rotational movement of the eye 1 from a translational displacement of the eye. A rotational movement of the eye 1 may be determined by monitoring a fourth Pukinje image (Pukinje IV) of the eye with respect to an aspect of the eye which changes with rotation of the eye, such as, for example, the outer ring of the pupil of the eye 1. The Pukinje IV image results from the specular reflection from the back surface of the lens of the eye 1. Monitoring the Pukinje IV image allows for separately monitoring the rotational and translational aspects of movements of the eye 1, because the Pukinje IV image does not change much during a rotational movement of the eye. Separating the rotational and translational movements of the eye can allow for adjusting optical aspects of the feedback system (or the application system) based on monitored translational movements, but not based on monitored rotational movements.

Additionally, or alternatively, the tracked position of the eye can be used to adjust a position of the eye 1. Similar to the description provided in connection with FIGS. 7B and 7C, a bite plate (and/or another head restraint device) may be provided that is coupled to positioning motors. Adjusting the positioning motors can move the position of the patient's head, and thus the position of the patient's eye. Tracking the position of the eye 1 allows for aligning the monitoring system and/or the treatment system by moving the eye 1 (e.g., via the bite plate 770 connected to positioning motors 772), by moving the monitoring and/or treatment system (e.g., by adjusting a position of an objective optical element), or any combination thereof.

FIG. 6E provides a symbolic representation of aspects of the pixelated polarizing filter 652 in the interferometer shown in FIG. 6D. The pixelated polarizing filter 652 is in some respects similar to the polarizing quad filter 650, but in miniature and repeated in an array. In principle, the pixelated polarizing filter 652 could be constructed from an etched birefringent plate, but such a device is difficult to manufacture accurately. The pixelated polarizing filter 652 can be constructed from an array of micropolarizers such that the number of entries in the array of micropolarizers is similar to, or even identical to, the number of pixels in the CCD detector 660. FIG. 6E symbolically represents a portion of the pixelated polarizing filter 652, which is shown as an array, with each set of four pixels forming a group of linear micropolarizers. In an implementation, the pixelated polarizing filter 652 may be referred to as a pixelated polarizing plate.

Generally, information for conducting profilometry of the eye 1 can be extracted from a configuration where the effective polarization of the pixelated polarizing plate 652 is spatially distributed. The effective polarization of the pixelated polarizing filter 652 can have a regular repeating pattern, with out of phase polarizers alternating along the columns. For example, pixelated polarizers for interfering at 0 degrees (corresponding to the transfer function for A(x,y)) and 180 degrees (C.) can be arranged in an alternating pattern in one column, and pixelated polarizers for interfering at 90 degrees (B) and 270 degrees (D) can be arranged in an alternating pattern in adjacent columns. Alternating the out-of-phase signals advantageously minimizes the amount of phase-dependent error due to smearing of the sensing array in the CCD detector 660, which can be particularly prone to smearing effects for short exposure times. The four interferograms can then be analyzed to compute phase difference map(s) associated with the surface(s) being monitored and determine surface profile(s) for the surface(s). The four interferograms can be intensity patterns captured by the CCD detector 660, each associated with a polarization state (e.g., 0°, 90°, 180°, 270°).

The pixelated polarizing filter 652 is illustrated as being positioned adjacent to the CCD detector 660, however the pixelated polarizing filter 652 can alternatively be positioned at the focal plane of the optical transfer 630 and additional relay optics can be used to convey the light transmitted through the pixelated polarizing filter 652 to the CCD detector 660. In particular, in an implementation where the size of the pixels in the pixelated polarizing filter 652 are larger than the pixels of the CCD detector 660, optical elements may be employed to scale the effective pixel size of the CCD detector 660 as desired relative to the pixelated polarizing filter 652 by introducing magnifying optical elements. Thus, the physical spacing of the pixelated polarizing filter 652 and the sensor array of the CCD detector 660 do not need to be equal.

The interferograms pictured in FIG. 6E can be created from the output of the pixelated polarizing filter 652 by combining every fourth pixel in the CCD detector 660 to create the four interferogram patterns. Similar to the configuration of the interferometer shown in FIG. 6A, the pixelated polarizing filter 652 allows for the four interferograms to be captured simultaneously with a single exposure of the CCD detector 660. In an example, the duration of the exposure of the CCD detector 660 can be less than one millisecond and can be as low as thirty microseconds.

While phase-shifting interferometers have been shown employing polarizing beam splitters and polarizing masks to compare the phase differences between the reference beam 616 and the signal beam 614 in FIGS. 6A through 6E, generally any interferometer for comparing the phase shift between a reference beam reflected from a known reference surface and a signal beam reflected from a surface of the eye 1 can be employed to perform profilometry of the eye 1.

One technique for determining the three-dimensional surface shape of the eye 1, and particularly the cornea 2, employs an analysis of the phase difference map. The phase difference map can be created, for example, using the interferograms and Eqs. 2 and 3. The surface shape of the eye 1 relative to the reference mirror 612 can be extracted from the phase difference map. The phase difference map may be a table which provides the phase difference between the reference beam 616 and the signal beam 614 for each effective pixel position of the four interferograms. As will be appreciated, the phase difference map includes ambiguities according to the modulo $2\pi$ behavior of the arctangent function in Eq. 3. This ambiguity can be resolved by the process of spatial phase unwrapping. For example, the difference in the optical path length of the reference beam 616 and the signal beam 614 between two pixels in the phase difference map that both have the same phase, can be a distance equal to an integer number of wavelengths of the light emitted by the light source 610. Analyzing the phase difference map in the context of surrounding entries allows for "unwrapping" the phase ambiguity. Generally such analysis can be performed by a computer or data analysis system adapted to automatically analyze the measurements from the CCD detector 660 according to a pre-programmed routine. Similar to the description provided above in connection with FIG. 6A, the profile of the corneal surface 2A may be estimated based on the phase difference map and an estimated distance from the corneal surface 2A to the interferometer, which may be supplied by the distance measurement system 670. The analysis of the measurements to estimate the profile of the corneal surface 2A may be performed by the controller 120.

Once the surface shape of the eye 1 has been measured during a first exposure, subsequent surface shapes of the eye 1 measured during subsequent exposures can be compared with the first measured surface shape in order to determine changes in the surface shape (e.g., a dynamic deformation of the corneal surface), and thereby determine the biomechanical corneal strength or stiffness. Generally, such an analysis can be performed for a data array of 1 million pixels at a rate of several frames per second using a 2 GHz Pentium computer. In an example, an estimation of dynamic deformation of the corneal surface is estimated based on a series of subsequently captured surface profiles. Generally, however, where the corneal surface 2A is experiencing an approximately periodic perturbation (such as perturbations due to changes in IOP, which are rhythmically associated with a subject's heartbeat), an estimation of dynamic deformation is advantageously based on samples from the full phase-space of the perturbation. Systems may incorporate synchronizing devices to associate corneal surface profile measurements with an indication of a phase of the subject's heartbeat. The phase of the subject's heartbeat may be indicated by a separate cardiac measurement device, or may be extracted from the series of measurements by a signal processing technique adapted to effectively wrap or fold measurements on top of one another according to their associated phase and then optimizing the associated phases to minimize noise in the phase space modulation. Systems relying on perturbations other than IOP (or in addition to IOP) may similarly incorporate sensors to synchronize corneal surface profile estimations with an associated phase of the source of the perturbation.

After initial alignment, camera recording may be automatically initiated by monitoring the blink response of the patient. Furthermore, the embodiments can be adapted to monitor the blink response of the eye 1 and to report characteristics of the blink response, such as the blink rate, the blink duration, and characteristics of tear film build-up and break-up associated with the blink response. In addition, embodiments may be adapted to report average, minimum, maximum, and median blink rates and blink durations over a period of time.

Aspects may further provide for estimating tear film volume based on a difference between measured profiles of the corneal surface 2A. In an example, the tear film volume estimation can be based on a difference between subsequently measured profiles off the corneal surface.

In general, embodiments according to the present disclosure may provide integrated systems that evaluate additional characteristics of the eye 1 in addition to using an interferometer to measure the corneal surface 2A and strength of the corneal tissue. Embodiments may provide analyses of any combination of topography, wavefront, autorefraction, keratometry, pupillometry, tear film measurement, etc. Indeed, as explained with reference to FIG. 9B, the pre-operative and post-operative examinations in steps 916 and 918, respectively, may include determining visual acuity, refractive error, pupil size, intraocular pressure (IOP), corneal thickness, corneal topography, wavefront analysis, presence of dry eye-related disorders, etc. Aspects of the examination may be conducted at least in part with configurations of the present disclosure.

For example, the interferometry techniques described above in connection with FIGS. 6A through 6E may be employed to measure tear film thickness and evaluate tear film stability. Problems relating to tear film break-up and dry eye can be diagnosed. Indeed, such evaluation enables a practitioner to determine during a pre-operative examination whether a patient is a candidate for refractive surgery, such as LASIK (see step 912 of FIG. 9B). Tear film measurement can be enhanced with artificial tears containing microbeads of specific sizes and concentrations. The artificial tears can optionally have fluorescent markers to assist in measuring tear fluid dynamics by a measurement apparatus sensitive to fluorescence.

As described previously, an interferometer can provide data on the strength of the cornea 2 by measuring deflections of the corneal surface caused cardiac pulsate flow cycles. In general, changes in diastolic and systolic pressure magnitudes and differences may be analyzed with data from the interferometer to determine IOP and other biomechanical characteristics of the cornea 2.

Rather than relying on cardiac activity, however, the interferometer in other implementations can provide data on the corneal structure by measuring the response of the cornea 2 to a deformation that is applied from a controlled external source. For example, an ultrasonic pulse may be applied to the eye 1. Alternatively or additionally, pulses sweeping through a range of frequencies may be applied to the eye 1 and the interferometer can look for resonances that indicate the structural properties of the cornea tissue. In other examples, the external source is positioned so that it is not in direct contact with the eye, and a puff of air or the like may be delivered to cause deformation of the cornea 2 in a controlled manner.

In another embodiment of the light source 610 in the interferometry system may be a multispectral light source. In an implementation, moving a reference arm of the interferometer, which can adjust a position of the reference surface 612, allows for probing the different surfaces within the eye. For example, the different surfaces within the eye can be probed by looking at the different spectral oscillations off of each refractive surface interface (e.g., the interfaces between the layers associated with the eye 1). The spectral oscillations can be the constructive and deconstructive interference between the layers at different wavelengths. In this manner, the surface layer shape as well as layer thickness can be measured. The surfaces and layers that can be measured include, without limitation: the tear film layers, the endothelium, Bowman's membrane, stroma, Descemet's membrane, and the endothelium. The surfaces that can be measured include the surfaces defined by the interfaces between each of the refractive layers (e.g., the tear film layers, the endothelium, Bowman's membrane, stroma, Descemet's membrane, and the endothelium). In addition, layers (and associated surfaces defined by interfaces between the layers) may include, for example, a contact lens and its tear film above and between the contact lens and the epithelium. Implementations may also measure posterior and anterior surfaces of the lens of the eye.

Further embodiments of the present disclosure may employ a Shack-Hartmann wavefront sensor, or may employ a Shack-Hartmann sensor in combination with an interferometer to conduct profilometry of the cornea 2. The Shack-Hartmann wavefront sensor provides information for the treatment of the cornea 2 by analyzing light emerging from the optical system of the eye 1 and detecting aberrations of the cornea 2. A Shack-Hartmann wavefront sensor employs an array of microlenses of the same focal length. A light source is directed to create a virtual light source near the rear of the eye 1 to provide light for emerging from the eye 1. Each microlens creates a beam focused onto a spot on a focal plane where a photon sensor, e.g., a CCD camera, is placed. The displacement of the spot with respect to a precalibrated position (corresponding to an undisturbed wavefront) is proportional to the local slope of the wavefront emerging from the eye 1. Detecting the spots and integrating their displacements across the focal plan provides an estimate of the wavefront shape, which is itself an estimate of the shape of the corneal surface 2A of the eye 1.

Other embodiments according to the present disclosure may combine the use of an interferometer (and a wavefront sensor) with a Scheimpflug camera, which determines the thickness of the cornea 2, i.e., corneal pachymetry, as well as the thickness of the intraocular lens. Such embodiments provide data on the anterior as well as posterior segments of the eye, enabling a full biomechanical analysis of the eye particularly after a treatment such as thermokeratoplasty has been applied. Some embodiments may employ a rotating Scheimpflug camera to capture, for example, 25 or 50 images, to collect data on the anterior segment. Alternatively, other embodiments may scan along one plane and then rotate 90 degrees to scan across another plane to define a grid according to which the anterior segment may be analyzed.

Still further embodiments may provide information on the surface of the eye 1 using an interferometer arranged such that the reference beam 614 is reflected from the eye 1 at some incident angle, which allows the interferometer to be sensitive to motion along the bisector of the incident angle. The motion may be due to, for example, dynamic deformation of the corneal surface 2A of the eye 1. Comparisons between multiple measurements with such an angled interferometer configuration can also provide information on the surface strain of the eye 1.

The interferometry techniques described above may be employed for real-time monitoring of cross-linking and may be used with thermokeratoplasty or LASIK surgery. However, these techniques are not limited to such applications. For example, aspects of the present disclosure may be employed to treat keratoconus. In particular, data from the interferometer provides a pattern of the keratoconus that can be used to guide the application of an initiating element, e.g., via laser scanning and eye tracking technologies, and increase the amount of cross-linking in desired areas. In general, data from the interferometer can be used by a controller to guide the hardware that generates cross-linking activity. With reference to FIG. 4, in an implementation the feedback system 400 may comprise an interferometer similar to the interferometers provided in FIGS. 6A and 6D. In such a configuration, the signal beam 614 can be considered the measurements 402, and the data from the interferometer (i.e., the interferograms) can be considered the feedback information 404.

The interferometry techniques above may also be employed to monitor other procedures that surgically or mechanically modify aspects of the eye 1. For example, when penetrating keratoplasty is used to treat the cornea 2, the biomechanics of the corneal graft can be monitored and the tensioning of the sutures can be monitored in real-time.

Another technique for real time monitoring employs polarimetry to measure corneal birefringence and to determine the structure of the corneal tissue. In particular, the technique measures the structure of the corneal tissue by applying polarized light to the corneal tissue. Birefringence describes the effect of some materials to retard transmitted light polarized along an axis of birefringence of the material relative to transmitted light polarized orthogonal to the axis of birefringence. For example, a birefringent material may receive a light signal having components polarized both parallel and perpendicular to the axis of birefringence, and the transmitted light can emerge with one of the components phase delayed relative to the other. In some implementations, the effect of transmitting linearly polarized light through a birefringent material is to rotate the polarization of the transmitted light relative to the incoming light, and the amount of rotation of the polarization can be adjusted by modifying the orientation of the birefringent material. For example, the effect of some materials to effectively decompose a light beam into two beams when it passes through the material that have anisotropic (directionally dependent) structure, can describe the effect of a birefringent material. If the material has a single axis of birefringence, two refractive indices can be respectively assigned for polarizations parallel and perpendicular to the axis of birefringence for an arbitrary incoming light signal. The light of one polarization propagates more slowly through the birefringent structure than light of the other polarization and becomes retarded in phase. Thus, parameters characterizing birefringence are the axis of birefringence and the magnitude of retardation.

The corneal stroma is anisotropic and its index of refraction depends on direction. The cornea behaves like a curved biaxial crystal with the fast axis orthogonal to the corneal surface and the slow axis (or corneal polarization axis) tangential to the corneal surface. Accordingly, a light beam emerging from the living eye after a double pass through the ocular optics contains information on the polarization properties of all ocular structures (except optically inactive humours). In particular, a portion of a light beam which enters the eye and passes through the cornea may be reflected at the iris and then pass back through the cornea to exit the eye. The light emerging from the eye has thus completed a double pass of the cornea. Analysis of the portion of the light beam reflected from the iris and emerging from the eye can reveal structural information about the cornea 2.

Figure 7A:
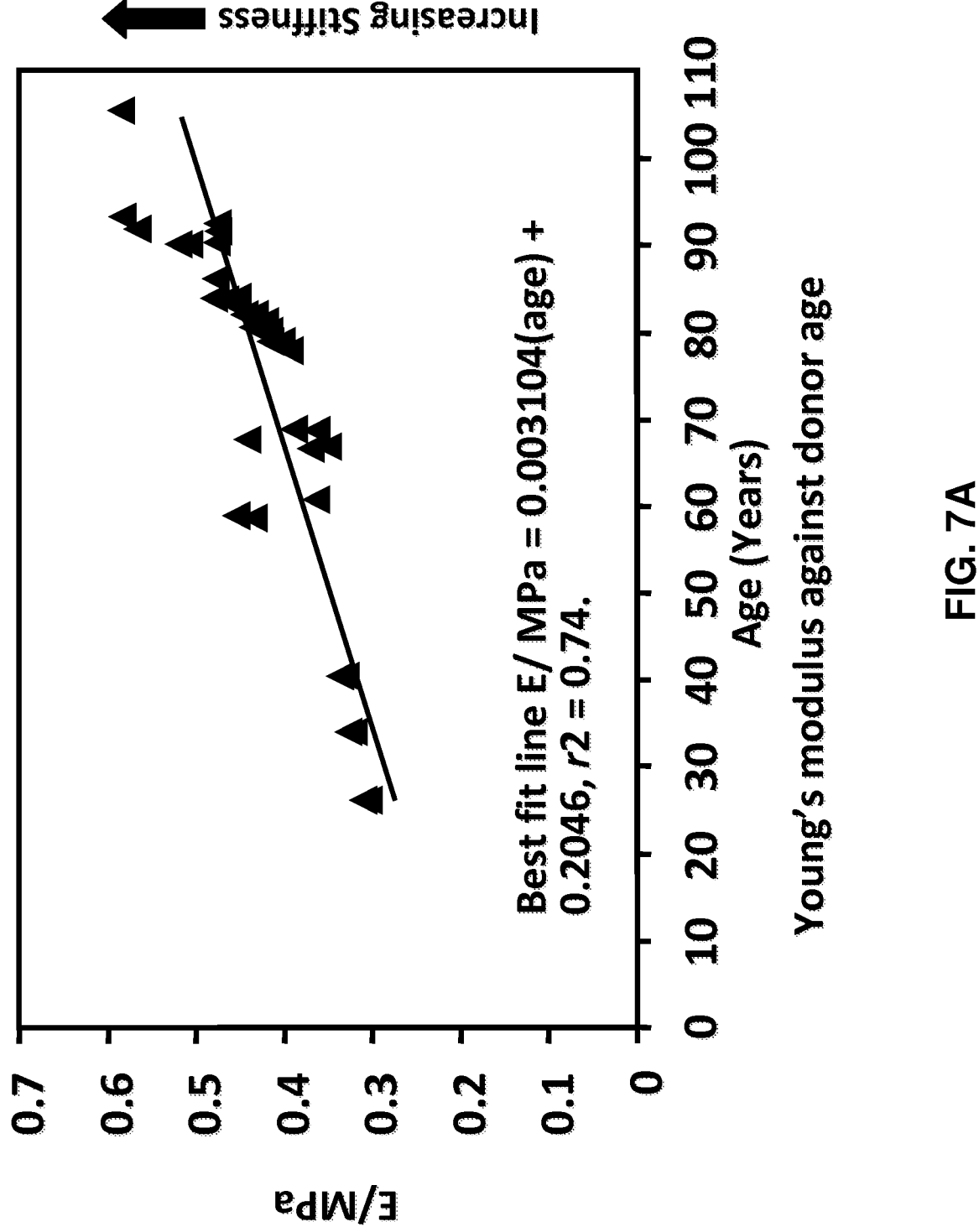
FIG. 7A illustrates the increase in Young's modulus with age and is associated with cross-linking.

FIG. 7A illustrates the increase in Young's modulus with age and is associated with cross-linking as demonstrated in: Nathaniel E. Knox Cartwright, John R Tyrer, and John Marshall, Age-Related Differences in the Elasticity of the Human Cornea. *Invest. Ophthalmol. Vis. Sci.* Sep. 16, 2010; doi:10.1167/iovs.09-4798, the contents of which is herein incorporated by reference in its entirety. Young's modulus provides a measure of the elasticity or stiffness of a material. Generally, a higher value of Young's modulus indicates a greater resistance to deformation under a particular stress load. Young's modulus can be computed as a ratio of applied stress (i.e., tensile or compressive pressure) to measured strain (i.e., dimensionless measure of deformation) of a material, and can be measured experimentally by taking a slope of a graph of stress versus strain for a particular material. Referring to TABLE 1, it has been shown that the stiffening effects of applying Riboflavin and UV light to initiate cross-linking appears to be equivalent to the effect of aging to the cornea by more than 500 years.

TABLE 1

| Condition | Young's Modulus | Age (Years) |
|---|---|---|
| Normal | 0.49 | 80 |
| UV Riboflavin | 2.25 | 600 |
| Glutaraldehyde | 3.76 | 1000 |

Due to the birefringent nature of the anistropic corneal collagen structures, light emerging from the eye after a double pass through the corneal tissues may be less polarized than the incoming light. That is, in a system measuring the polarization properties of light emerging from the eye following a double pass through the corneal tissues, the emerging light may include a larger fraction of depolarized light than the incoming light. Referring to TABLE 2, a study has shown that the amount of depolarized light emerging from the eye following a double pass of the corneal tissue generally correlates with the age of the subjects in the study. See Bueno, J. M. *J. Op. A: Pure Appl. Opt.* 6 (2004), S91-S99, the contents of which is herein incorporated by reference in its entirety. Thus, the degree of polarization may provide a measure of corneal stiffness, and thus a measure of cross-linking activity. In particular, a lesser degree of polarization (or equivalently, an increased amount of depolarized light) may be indicative of an increased amount of corneal stiffness, and thus be indicative of an increased amount of cross-linking activity.

TABLE 2

| Subject | Age | Degree of Polarization |
|---|---|---|
| 1 | 24 | 0.92 |
| 2 | 27 | 0.76 |
| 3 | 30 | 0.80 |
| 4 | 32 | 0.77 |
| 5 | 41 | 0.74 |
| 6 | 67 | 0.61 |
| 7 | 70 | 0.67 |

While the tables illustrate relationships between degree of polarization and corneal stiffness and age, the information gained from the degree of polarization may be used in an implementation apart from a particular subject's age. For example, a degree of polarization of light emerging after a double pass through the corneal tissues of a patient's eye can provide information indicative of a baseline amount of corneal stiffness before commencing an eye therapy treatment. The progress of an eye therapy treatment can then be checked at intervals by measuring subsequent degrees of polarization, and, if desired, variable parameters for controlling the application of the eye therapy treatment can be adjusted according to the corneal stiffness indicated by the subsequent measurements of degree of polarization.

FIGS. 7B through 7E provide laboratory set-ups that may be employed to measure corneal birefringence and polarization properties of light emerging after a double pass through the corneal tissues. Any of the set-ups and systems provided in FIGS. 7B through 7E may be coupled to an analysis system adapted to analyze obtained information indicative of the polarization properties of the cornea 2. The analysis of the information may be carried out by, for example, solving for a Mueller matrix describing the optical effect of the corneal tissue on the light reflecting from the iris 5. Collectively, the measurement and analysis systems for measuring the corneal birefringence of the corneal tissues may be referred to as a corneal polarimetry system. With additional reference to FIG. 4, the feedback system 400 may comprise a corneal polarimetry system. Information indicative of the polarization properties of the cornea 2 obtained by any of the systems illustrated in FIGS. 7B through 7E may provide the measurements 402. In particular, the intensity of light (e.g., the intensity detected by the CCD camera 760 in FIGS. 7B through 7E) after completing a double pass through the cornea 2 may comprise the measurements 402. The degree of polarization computed by the analysis system of the corneal polarimetry system may comprise the feedback information 404, which is then passed to the controller 120. The controller 120 may be adapted to analyze the feedback information 404 and provide the command signals 406 to the light source 110. As previously discussed, the controller 120 may be further adapted to provide the command signals 406 to additional components to control the amount and degree of cross-linking activity being initiated in the cornea 2.

Once the information indicative of the polarization of the cornea 2 has been gathered by one of the measurement systems illustrated in FIGS. 7B through 7E, the birefringence can be calculated. For example, with reference to FIG. 7B, the three images of the pupil's plane recorded according to the three independent polarization states of the analyzer can be used to provide independent variables to solve the Mueller-Stokes matrix with retardation $\Delta$ and azimuth $\alpha$ (fast axis).

Figure 7B:
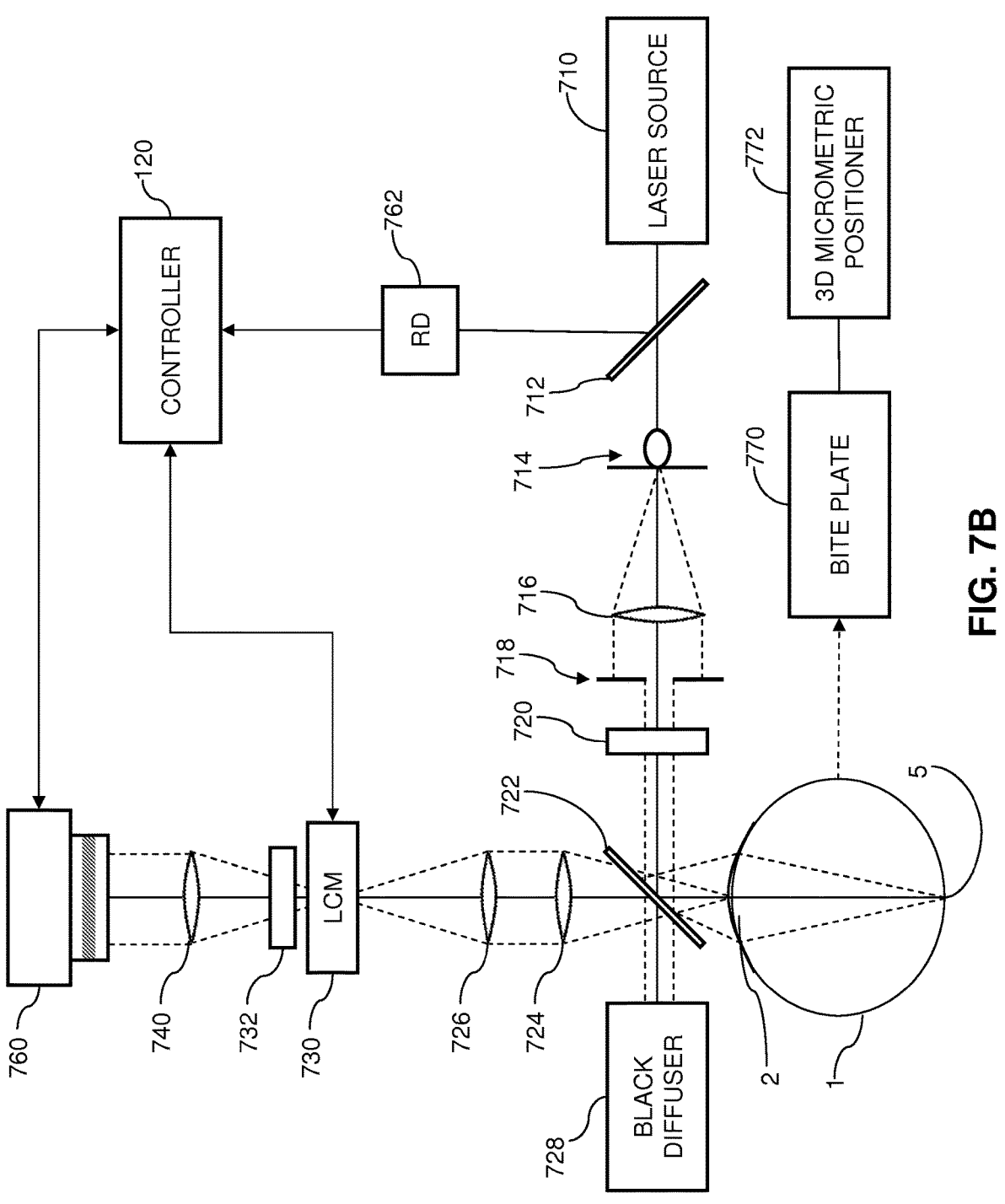
FIG. 7B provides an approach for calculating birefringence using a corneal polarimetry system.

Referring to FIG. 7B, an approach for calculating birefringence using a corneal polarimetry system is shown. See Bueno J. M., et al. *Applied Optics* (2002), v.41, 116-124, the contents of which are incorporated entirely herein by reference. The corneal polarimetry system shown in FIG. 7B includes a laser source 710, which can be a 633 nm He—Ne laser. The laser source 710 illuminates the eye 1, and light reflected form the iris 5 after a double pass through the corneal tissue is passed through a liquid-crystal modulator ("LCM") 730. The LCM 730 may be an LCM provided by Meadowlark Optics, such as the HEX69. After passing through the LCM 730, the light is focused by an objective lens 740 onto an imaging plane of a camera 760. The camera 760 may include a CCD detector. The controller 120 may send and receive signals to both the camera 760 and the LCM 730 and may be adapted to analyze the intensity information provided by the camera 760 in combination with different polarization settings of the LCM 730 to determine the birefringence of the cornea 2. In addition, the controller 120 may receive signals from a reference detector ("RD") 762 to account for brightness fluctuations in the laser source 710.

The polarimetry system of FIG. 7B further includes a beam splitter 712 for splitting the output of the laser source 710 toward the RD 762, with the rest continuing on toward the spatial filter 714. The spatial filter 714 is provided to filter and expand the output of the laser source 710, and may include a microscope objective and a pinhole. The filtered and expanded light is then directed toward a first lens 716 to collimate the beam. The beam then passes through an aperture 718, which controls the size of the beam. The aperture 718 may have a diameter of 12 mm. The output of the aperture 718 is then passed through a linear polarizer 720, which is oriented with its transmission axis of polarization at a 45° to a horizontal orientation. The beam is then split again by a second beam splitter 722, which reflects the beam toward the eye 1. Some of the light then completes a double pass of the cornea 2, with reflection at the iris 5. The reflected light then emerges back through the cornea 2, and half passes through the second beam splitter 722 to be directed toward the camera 760. A black diffuser 728 is also provided to reduce undesirable reflection and scattering from the portions of the beam that are directed to the black diffuser 728 by the second beam splitter 722. Lenses 724, 726 conjugate the pupil plane of the eye 1 with the LCM 730, which may be, for example, 15 mm in diameter. A second linear polarizer 732 is placed behind the LCM 730, and is oriented parallel to the linear polarizer 720. The combination of the LCM 730 and the second linear polarizer 732 act as a polarization state analyzer ("PSA"). The objective lens 740 then focuses the beam on an imaging plane of the camera 760.

The LCM 730 may be oriented with a fast axis in a vertical orientation. When driven with appropriate voltages by the controller 120, which can be defined, for example, during a calibration of the system shown in FIG. 7B, the LCM 730 may produce three completely independent polarization states. A series of three images may then be obtained, with each image indicative of the intensity of light detected by the camera 760 in one of the three different polarization states. Each pixel of the images corresponds to an area of the pupil plane. The intensities detected by the camera 760 of the different polarization states provide information for solving the Mueller matrix of a birefringent sample with retardation $\Delta$ and fast axis orientation $\alpha$ according to the Mueller-Stokes formalism, the details of which are provided elsewhere. See, e.g., Bueno J. M., et al. *Applied Optics* (2002), v.41, 116-124.

The position of the eye 1 may be stabilized by a bite plate 770 mounted on a three axis micrometric positioner 772. When a subject/patient bites down on the bite plate 770, the position of the subject's head is stabilized. Moving the bite plate 770 using the micrometric positioner 772 controls the position of the subject's eye 1.

In a system where the corneal polarimetry system provided in FIG. 7B is integrated into the feedback system 400, the controller 120 may be the same controller as that shown in FIG. 4. In such a configuration, the controller 120 may be adapted to analyze the birefringence information extracted by the corneal polarimetry system and map the birefringence of the cornea 2 to an equivalent amount of cross-linking. The mapping may be performed according to birefringence information obtained in a preliminary (i.e., pre-treatment) examination of a subject. The mapping may be calibrated according to additional measures of corneal stiffness of the subject. Additionally or alternatively, the mapping may be informed according to average amounts of corneal birefringence observed in subjects with similar characteristics and profiles to the particular subject being monitored by the corneal polarimetry system. In an alternative embodiment, the controller 120 may be replaced by a separate controller different from the controller utilized to control the cross-linking activity. The separate controller may be adapted to automatically send and receive information to and from the controller 120, or may be adapted as a completely separate system that provides the birefringence information to be evaluated by a user, or by a physician.

Figure 7C:
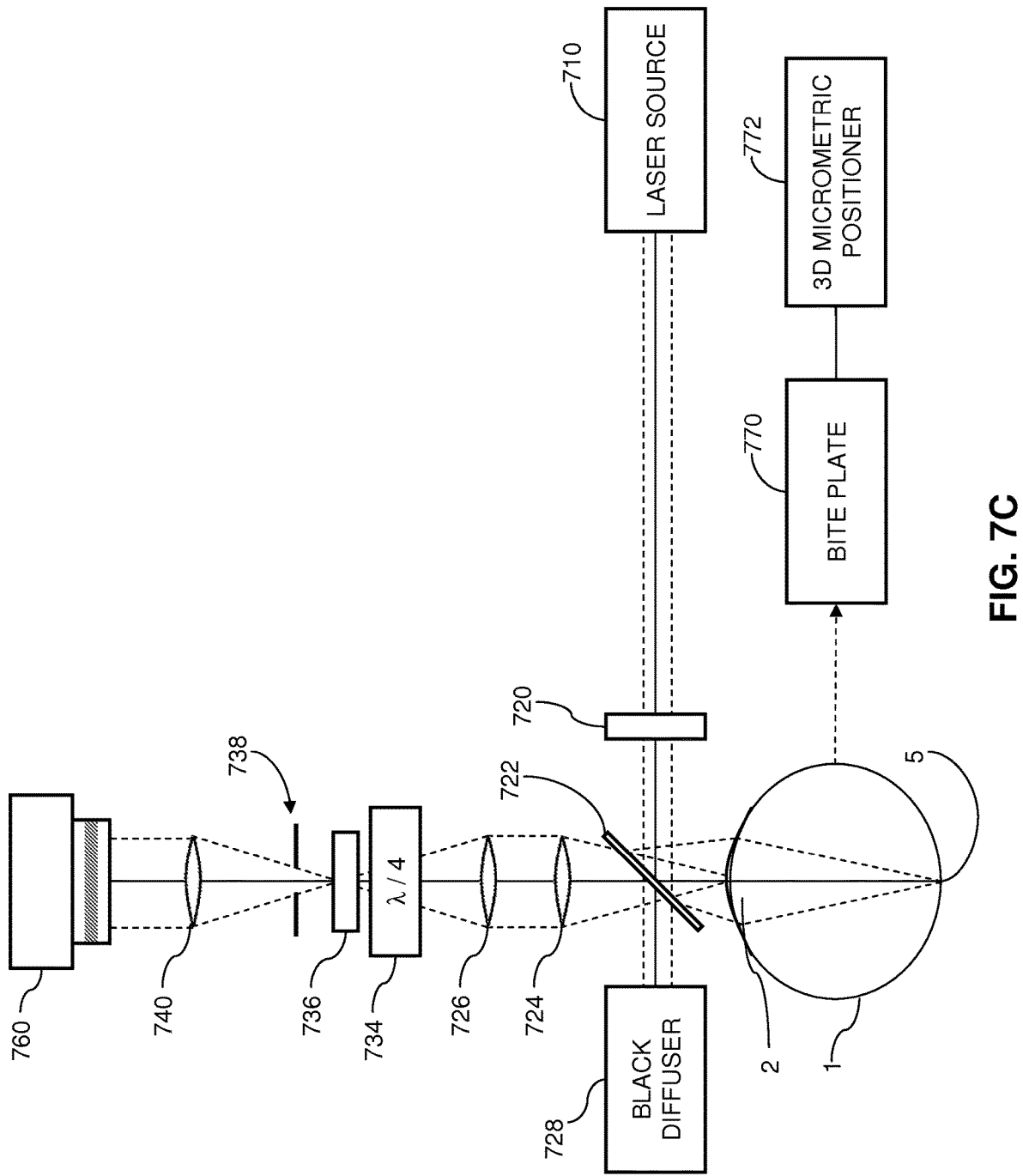
FIG. 7C provides an alternative configuration of a corneal polarimetry system useful for detecting information indicative of the corneal birefringence.
Figure 7D:
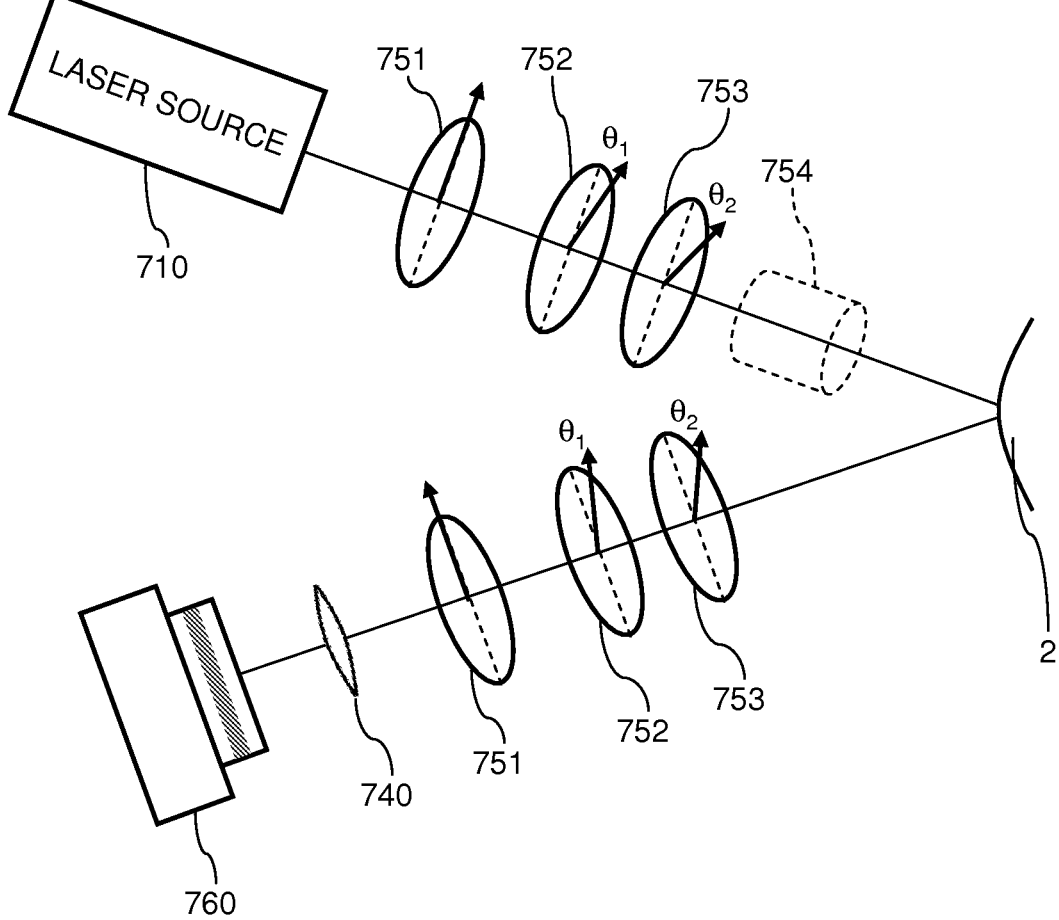
FIG. 7D provides another alternative configuration of a corneal polarimetry system useful for detecting information indicative of the corneal birefringence.
Figure 7E:
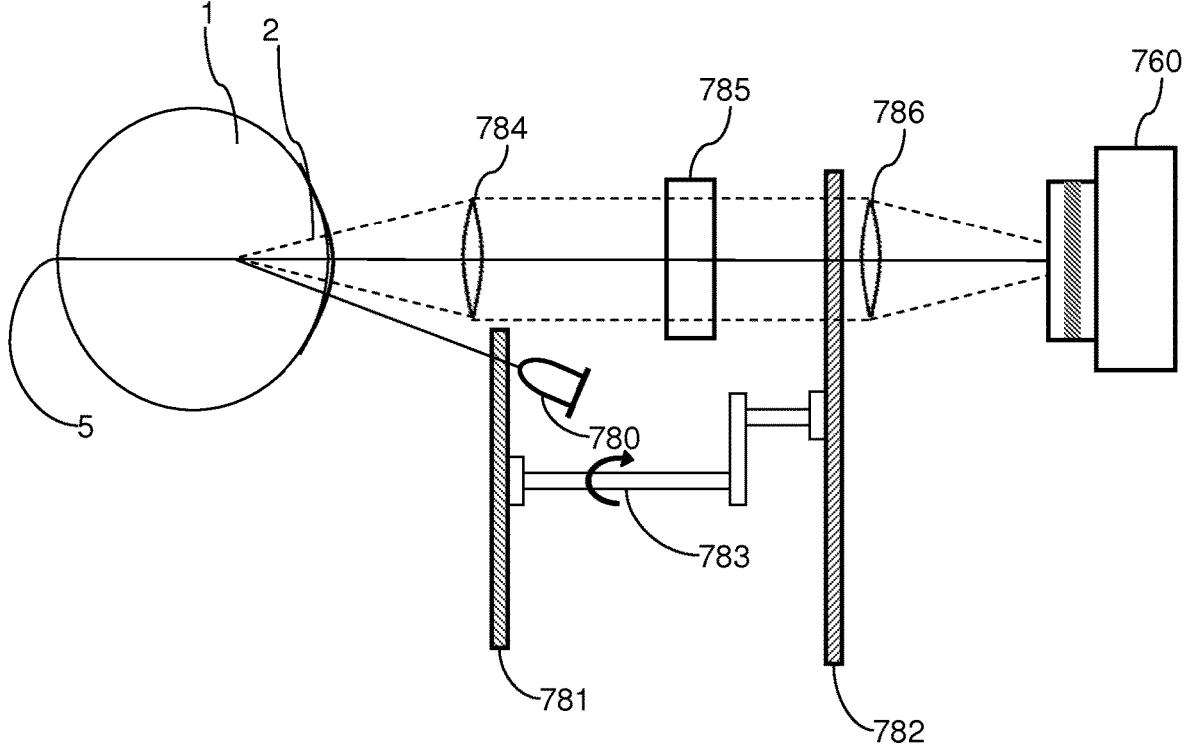
FIG. 7E schematically illustrates yet another configuration of a corneal polarimetry system useful in extracting birefringence information of the corneal tissue.

As previously discussed, FIGS. 7C, 7D, and 7E provide alternative configurations of corneal polarimetry systems useful for detecting information indicative of the corneal birefringence. Details of the configurations in FIGS. 7C through 7E may be found in Bueno, J. M. *J. Op. A: Pure Appl. Opt.* 6 (2004), S91-S99; Richert M., et al. *EPJ Web of Conferences* 5 (2010), 1-5; Knighton R. W and Huang, X. R. *Invest. Opt. Vis. Sci.* 43 (2002), 82-86, respectively, the contents of which are incorporated entirely herein by reference.

With reference to FIG. 7C, the laser source 710 may be a collimated infrared laser beam with 780 nm wavelength and 1.5 mm in diameter. The linear polarizer 720 may be oriented to vertically polarize the light from the laser source 710. The polarized light is then directed by the second beam splitter 722 to complete a double pass of the corneal tissues and collimated by the lenses 724, 726. The lenses 724, 726 may be achromatic doublets. The beam is then passed through an analyzer unit, which includes a rotatory retarder 734 and a vertical polarizer 736. An aperture 738 limits the size of the beam to 5 mm, and the objective 740 focuses the beam on the imaging plane of the camera 760. Rotating the rotatory retarder 734 provides different polarization states of the analyzer unit. To extract the birefringence information of the cornea 2, the analyzer unit may be adapted in four independent polarization states and images may be recorded with the camera 760 in each orientation. The images thus obtained can then be analyzed to extract the birefringence information. For example, the four independent polarization states may correspond to orientations of the rotatory retarder 734 with the fast axis at −45°, 0°, 30°, and 60°.

Either of the corneal polarimetry systems provided in FIG. 7B or 7C may optionally further include a video camera to control the correct positioning of the subject's eye 1 by use of the micrometric positioner 772. The additional video camera can be adapted to be connected to a controller (such as the controller 120) which automatically detects the location of the eye 1 and corrects the position of the eye 1 by adjusting the micrometric positioner 772, which moves the subject's head through the bite plate 770. Alternatively, the video camera can be adapted to display the video feed of the eye 1 on a display and an operator can use a manual method of manipulating the micrometric positioner 772 according to the displayed video of the eye 1. For example, the video feed of the eye 1 may be superimposed on a target or annulus, and an operator may adjust the micrometric positioner 772 with a joystick to maintain the eye 1 in a desirable location relative to the video feed.

Alternatively or additionally, the corneal polarimetry system can be mounted on a motorized system and can be adapted to move automatically instead of, or in addition to, the micrometric positioner 772 moving the eye 1.

FIG. 7D schematically illustrates a further configuration of a corneal polarimetry system arranged in a backscattering configuration. The corneal polarimetry system of FIG. 7D includes the laser source 710, which may be a Nd—Yag doubled continuous laser from Spectra Physics that operates at 532 nm. A linear polarizer 751 vertically polarizes the light from the laser source 710. The linearly polarized light is then passed through two nematic liquid crystals 752, 753 oriented with their fast axis indicated by the arrows in FIG. 7D having angles $\theta_1$ and $\theta_2$ with the orientation of the linear polarizer 751, respectively. The linear polarizer 751 and the two nematic liquid crystals 752, 753 may be considered a polarization state generator. The two nematic liquid crystals 752, 753 act as adjustable retardance elements. The beam may then optionally be passed through a spatial filter 754. The beam then completes a double pass the corneal tissue of the eye 1, and is reflected toward a polarization state analyzer. The polarization state analyzer includes the same components as the polarization state generator, but the beam passes through in reverse order. The beam is then focused by the objective lens 740 to an imaging plane of the camera 760. The values of the orientation and retardance of each of the retardance elements 752, 753 are chosen in order to minimize the propagation of errors from intensities to the calculus of Mueller matrices. Similar to the analysis of the corneal polarimetry systems already discussed, the Mueller matrix of the corneal tissue is obtained by successively generating four linearly independent states of polarization and by analyzing the backscattering field projected along the four linearly independent states.

The corneal polarimetry system having a backscattering configuration of FIG. 7D may be adapted with an angle of approximately 10° between the input beam and the output beam, and the laser source 710 may be, for example, approximately 1.5 m from the cornea 2.

FIG. 7E schematically illustrates yet another configuration of a corneal polarimetry system useful in extracting birefringence information of the corneal tissue. The corneal polarimetry system of FIG. 7E includes light-emitting diode ("LED") 780. The LED 780 can have a peak wavelength of 585 nm and can be oriented 7.1° below the optic axis of the cornea 2. Light reflected from the poster surface of the cornea 2 formed the so-called fourth Pukinje image ($P_{IV}$), which is a small, inverted image of the LED. Identical achromatic collimating lenses 784, 786 magnify the Pukinje image and focus the image on the imaging plane of the camera 760. In an implementation, the camera 760 can be replaced by an eyepiece for a user to look through and observe the cornea 2. Rotating linear polarizers 781, 782 and linked to a common shaft 783 and are oriented with their axis of polarization perpendicular to one another. Thus, light from the LED 780 polarized by the first linear polarizer 781 is blocked by the second linear polarizer 782 unless the light has undergone a change in polarization.

At most polarization orientations, the double-pass through the corneal tissue converts the light emitted from the LED 780 having a polarization oriented according the first linear polarizer 781 to an elliptical polarization state. A Berek variable retarder ("BVR") 785 is located in the collimated beam between the collimated lenses 784, 786. The BVR may be acquired from New Focus of Santa Clara, CA, and may include a tiltable, rotatable plate of $MgF_2$. The BVR 785 can be adjusted in azimuth and retardance to cancel the effect of birefringence during a double pass through the corneal tissue. Estimates of the corneal birefringence may be obtained by the corneal polarimetry system shown in FIG. 7E by first setting the BVR 785 to zero retardance and observing the Pukinje image. Then, the BVR 785 is rotated until the Pukinje image disappears. The amount of rotation of the BVR 785 required to cancel the Pukinje image provides an indication of the amount of birefringence associated with the corneal tissue 2.

The angle of illumination is an important aspect in the techniques directed to measuring birefringence in the cornea 2, because it affects the observed birefringent pattern. Accordingly, in one embodiment, the polarized illumination of the eye may be varied from converging to meet the radius of curvature of the cornea 2 to providing a collimated beam. By taking images of birefringence as the angle of light is varied, one can obtain a quantitative measure of the birefringence as a function of illumination angle and de-convolve the arrangement of lamina, in addition to obtaining a measure of central corneal birefringent retardation. Advantageously, this approach uses the angle variation to differentiate anomalies in the stroma more effectively.

Furthermore, it is understood that the concepts described herein are capable of varying combinations: birefringence analysis (i.e., corneal polarimetry) only; interferometry analysis only; corneal topography analysis only; a combination of interferometry and corneal topography analysis; a combination of birefringence, interferometry, and corneal topography analysis; and so on. For example, because the beam from the interferometer converges to meet the radius of curvature of the cornea, this technique may be combined with the birefringence technique described above.

Figures 8A, 8B:
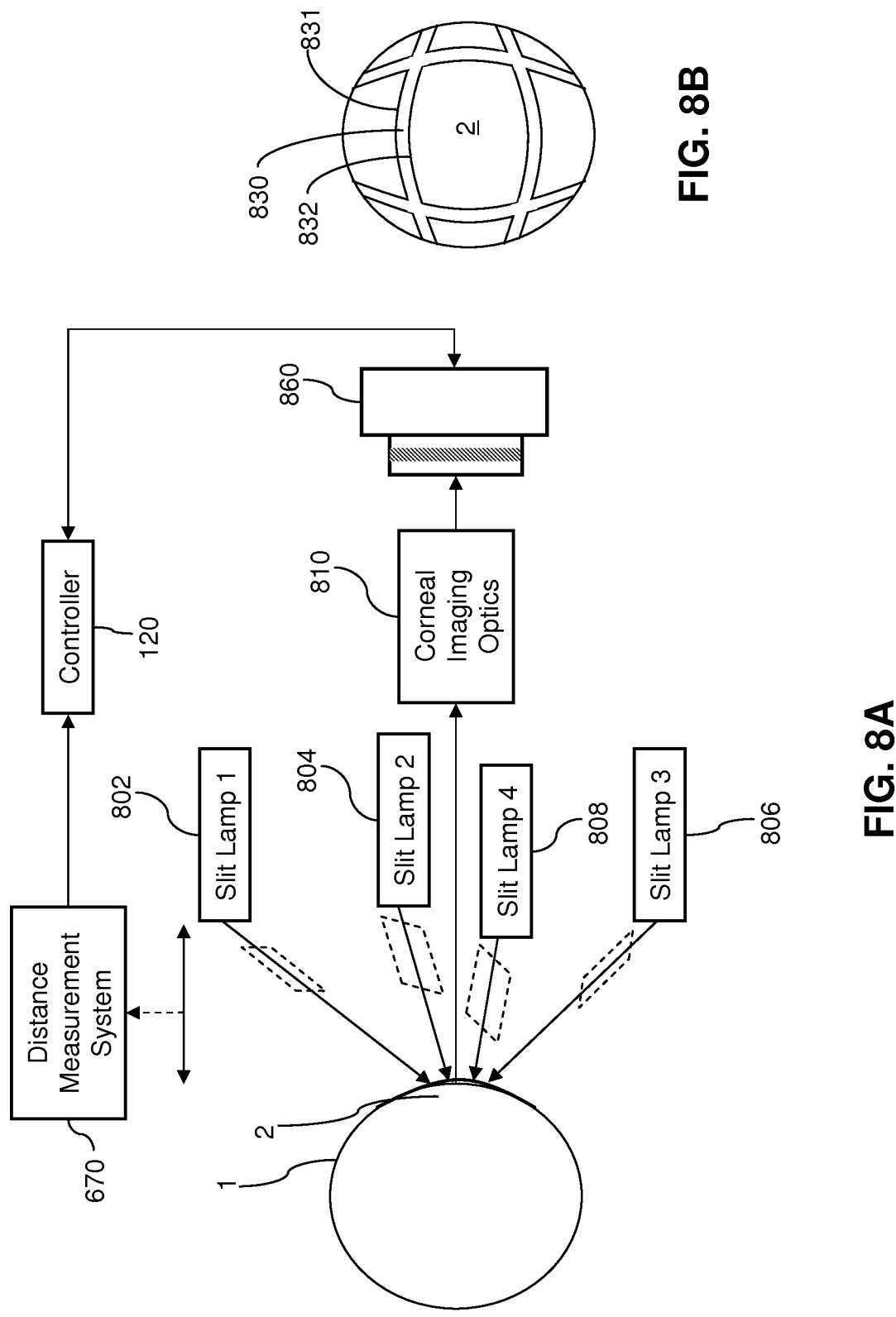
FIG. 8A illustrates a configuration utilizing multiple slit lamps to perform corneal topography and pachymetry.
FIG. 8B schematically illustrates an image of the cornea detected by the camera in a configuration utilizing four slit lamps.

FIG. 8A illustrates a configuration utilizing multiple slit lamps to perform corneal topography and pachymetry. The multiple slit lamp configuration may also provide targeting information to implementations of the feedback system 400. The multiple slit lamp configuration shown in FIG. 8A includes four slit lamps 802, 804, 806, 808. Each of the slit lamps 802, 804, 806, 808 may be similar to a conventional slit lamp employed in the field of optometry and ophthalmology to examine a patient's eye and to diagnose conditions existing in the layers of the eye. Each of the slit lamps may be adapted to illuminate a portion of the cornea 2 with light emerging from a slit. The slit may be an aperture having a narrow dimension and a broad dimension. While the narrow dimension is finite, the light emerging from the slit lamp may be approximately considered as a sheet of light, which illuminates a plane of the cornea 2. The four slit lamps 802, 804, 806, 808 may be oriented off-center from the optical axis of the cornea 2, and may be oriented with each at 45° with respect to the eye 1. Furthermore, the four slit lamps may be positioned such that they are equally spaced around the eye 1.

The first slit lamp 802 may be positioned above the eye 1 and may direct a sheet of light downward at 45° with respect to the eye 1. The second slit lamp 804 may be positioned to the left of the eye 1 and may direct a sheet of light rightward at 45° with respect to the eye 1. The third slit lamp 806 may be positioned below the eye 1 and may direct a sheet of light upward at 45° with respect to the eye 1. The fourth slit lamp 808 may be positioned to the right of the eye 1 and may direct a sheet of light leftward at 45° with respect to the eye 1. In the schematic illustration provided in FIG. 8A, the second slit lamp 804 is positioned further into the page than the first slit lamp 802 and the third slit lamp 806. The fourth slit lamp 808 is positioned further out of the page than the first slit lamp 802 and the third slit lamp 806.

The intensity pattern created by the multiple slit lamps illuminating cornea 2 is directed by the corneal imaging optics 810 to the camera 860. Intensity patterns detected by the camera 860 are then analyzed by the controller 120 to extract corneal topography and pachymetry information. An illustrative schematic of an example intensity pattern created by the four slit lamp configuration is provided in FIG. 8B.

The four slit lamps illuminate four curved lines on the cornea 2. The shape and thickness of the pattern observed on the cornea 2 provides information indicative of the shape of the corneal surface (i.e., corneal topography) and the thickness of the cornea 2 (i.e., corneal pachymetry). The thickness of the sheets of light observed with the camera 860 provide an indication of the corneal thickness when the precise parameters of the slit lamp orientation and position are known, including the thickness of the aperture of the slit lamps 802, 804, 806, 808. As the cornea 2 moves in and out relative to the position of the multiple slit lamps, the illumination pattern observed in the camera 860 changes as the sheets of light emitted from the slit lamps scan over the surface of the cornea 2. As the eye 1 moves relative to the slit lamps, the four curved lines sweep out a grid on the cornea 2. The curvature of the lines provide information indicative of the three dimensional profile of the eye surface. As the eye moves in and out with respect to the slit lamps 802, 804, 806, 808, a complete three dimensional profile of the corneal surface may be extracted.

According to an aspect of the present disclosure, the light reflected from the cornea 2 toward the corneal imaging optics 810 includes light reflected from the corneal surface (i.e., the anterior surface) and from the posterior surface of the cornea 2. With reference to FIG. 8B, in an implementation where the slit lamp 802 is oriented above the eye 1 and is directing a sheet of light downward toward the eye 1, the cornea 2 is illuminated with a line 830 having a top edge 831 and a bottom edge 832. The top edge 831 describes the anterior surface of the cornea 2, and the bottom edge 832 describes the posterior surface of the cornea 2. Similarly, other lines on the cornea have an edge closer to the direction of the associated slit lamp (a proximate edge), and an edge further from the direction of the associated slit lamp (a distal edge), and the proximate edge describes the anterior surface of the cornea 2 while the distal edge describes the posterior surface of the cornea 2. As some light is reflected from posterior (internal) surface of cornea, the light emerging from the cornea 2 and directed toward the camera 860 includes information on the position of the posterior surface and therefore the thickness of the cornea 2. The emerging light may also experience some spreading due to the diffusive optical characteristics of the corneal tissue. Ray tracing may also be employed to trace lines from slit lamps (e.g., the slit lamp 802) to the camera 860 to provide an estimate of anterior and posterior surfaces of cornea 2, and thus the shape and thickness of the cornea 2 at multiple locations may be extracted. By defining the shape and thickness of the cornea 2 at multiple locations, a three-dimensional profile of the cornea 2 may be determined. Using the camera 860, the surface estimates from the multiple slit lamp configuration may be matched to corneal surface estimates from an interferometry system (e.g., the interferometer systems of FIGS. 6A, 6D) to provide an even better estimate of the full corneal topography.

By providing a three dimensional profile of the cornea 2, the controller 120 can determine the center position of the cornea 2. The controller 120 can determine the center position by, for example, determining the apex of the three dimensional profile of the cornea surface. The determined center position may then be used in conjunction with adjustable optical and mechanical components to align any of the implementations of the feedback system 400 previously discussed.

The multiple slit lamp configuration illustrated in FIG. 8A also includes a distance measurement system 670 for determining the distance between the multiple slit lamps 802, 804, 806, 808 and the eye 1. In a configuration, the distance (or information indicative of the distance) is passed to the controller 120. The controller 120 uses the distance provided by the distance measurements system 670 in combination with the images from the camera 860 to get the radius of curvature of the eye 1, and thus the optical power of the eye 1. The distance measurement can also allow for scaling the images observed on the camera 860. The distance measurement system 670 may be implemented by two cameras focusing on the surface of the cornea 2, but oriented at an angle relative to one another, and separated by a known distance, such that the angle between the orientations of the two cameras when both are focused on the eye 1 provides an estimation of the distance according to standard trigonometric analysis. The distance measurement system 670 may be implemented as a high resolution camera capturing images from a known position. The high resolution camera may be oriented at approximately 90° to the optical axis of the eye 1, such that the edge of the eye 1 can be mapped to a pixel location of the high resolution camera, which corresponds to a distance from the slit lamps 802, 804, 806, 808. In addition, the distance measurement system 670 may be adapted according to an active ranging technique which uses reflected signals correlated with reference signals to measure time delays, such as a doppler, ultrasound, or optical ranging system.

Additionally, in a configuration where the positions of the slit lamps 802, 804, 806, 808 are well known, the distance may be estimated directly from the slit lamps, camera, and optical elements illustrated in FIG. 8A. Such a distance measurement may be performed by finely adjusting the position of the eye (e.g., via a positioning system mounted to a bite plate or head restraint similar to the micronometric positioner 772 shown in FIGS. 7B and 7C) until the intensity pattern observed by the camera 860 reflects a characteristic pattern (e.g., a cross centered on the apex of the cornea 2 formed by an overlap between the light of the upper and lower slit lamps 802, 806, and an overlap from the light of the side slit lamps 804, 808) that is indicative of a particular known distance. The position of the eye 1—or the position of the slit lamps and associated optics—may then be adjusted by known steps relative to the known distance as desired.

FIG. 8B schematically illustrates an image of the cornea 2 detected by the camera 860 in a configuration utilizing four slit lamps.

Figure 8C:
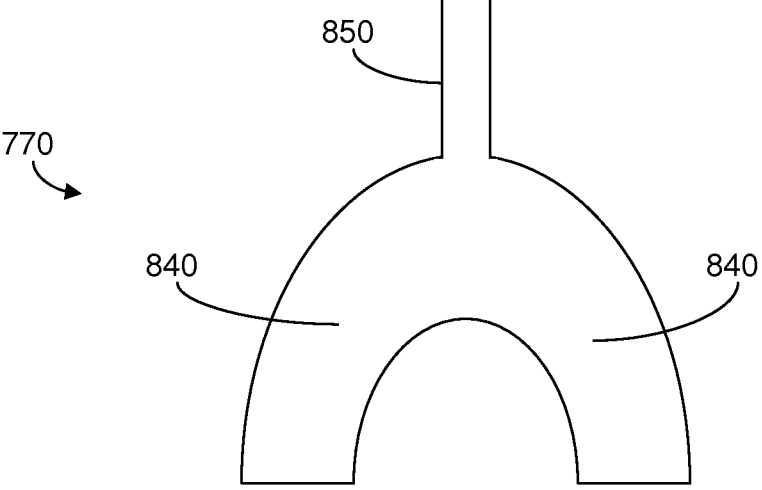
FIG. 8C illustrates an exemplary configuration of the bite plate for stabilizing a patient's eye during treatment and evaluation.

FIG. 8C illustrates an exemplary configuration of the bite plate 770 for stabilizing a patient's eye 1 during treatment and evaluation. The bite plate 770 includes a coupling 850 for connecting the bite plate 770 to an external component, such as a stationary rigid member or a member adapted to be moved by the micrometric positioner 772 of FIGS. 7B and 7C. With reference to FIG. 8C, an implementation of the bite plate 770 also includes a deformable material 840 distributed generally in a shape suitable for a user to bite on to. Alternatively, the bite plate 770 may be implemented as a bar (i.e., a bite bar). In an implementation, aspects of the bite plate 770 may resemble a protective mouth guard, a dental bite plate or bite tray, or a similar device. The bite plate 770 desirably fixes the location of a subject's head, and thereby fixes the location of the subject's eye 1, and can be replaced and/or supplemented by additional mechanical components adapted to restrain a subject's head (e.g., head restraint device(s)) and thereby fix the position of the eye 1. In implementations, the bite plate 770 and/or additional mechanical components for restraining a subject's head may be incorporated in the feedback systems (such as the exemplary interferometer systems described in connection with FIGS. 6A and 6D or the polarimetry systems described in connection with FIGS. 7B through 7E) or incorporated in cross-linking activation systems (such as the delivery system 100 described in connection with FIG. 1). By maintaining a subject's head (e.g., a patient's head) in a rigid configuration with respect to the various cross-linking activation systems and feedback systems described herein, the application of cross-linking and/or the monitoring of cross-linking activity can be more accurately performed.

With reference to the interferometer configurations shown in FIGS. 6A through 6E, to maximize the fringe contrast of the interferometer, aspects of the present disclosure may employ a positioning mechanism that fixedly positions the eye 1 and/or patient's head relative to the interferometer. The measurements of the deflections of the corneal surface 2A are more accurate when the patient's head is absolutely registered over several cardiac cycles. In one embodiment, the patient bites onto a fixed bite plate (such as the bite plate 770 illustrated in FIG. 8C) that minimizes motion of the patient's head while the images are taken by the interferometer. The bite plate 770 may be disposable and formed from a moldable material, e.g., a gel, soft plastic, a heat-moldable material, or the like. The bite plate 770 may also contain an RFID chip to monitor usage or to allow access to different diagnostic software modules. With the bite plate 770, even if the patient rotates his or her eyes, the head (skull) does not shift. As such, the rotation of the saccadic eye movements can be nulled out, e.g., by an algorithm, as a tilt in the direction of the motion. Additionally or alternatively, a chinrest and/or headrest may be employed to maintain cranial fixation and allow for the measurement of multiple frames over time.

The corneal polarimetry systems illustrated in FIGS. 7B through 7E, as well as other implementations of the feedback system 400 may also utilize the bite plate 770 to stabilize the patient's eye 1. Additionally, some embodiments may employ a visible fixation light source or object to help the patient align his or her eye relative to the interferometer. This visible fixation light source or object may be incorporated into the interferometer.

Furthermore, a camera may be employed to assist in aligning the interferometry system. The camera may be incorporated within the interferometer and may operate similar to the video camera 510 in FIG. 5A. The camera may be coaxially or non-coaxially aligned with the interferometer. The camera may also be employed to capture images that can be used for repeated future alignment. Additionally or alternatively, the camera may be employed for achieving alignment for secondary systems or procedures that are combined with the use of the interferometer. Additional mechanical, optical and or electrical control systems for course and fine alignment and adjustment of the interferometer to the corneal surface 2A may be employed, such as by manipulation of the positioning motors 617 described in connection with FIG. 6D.

Figure 9A:
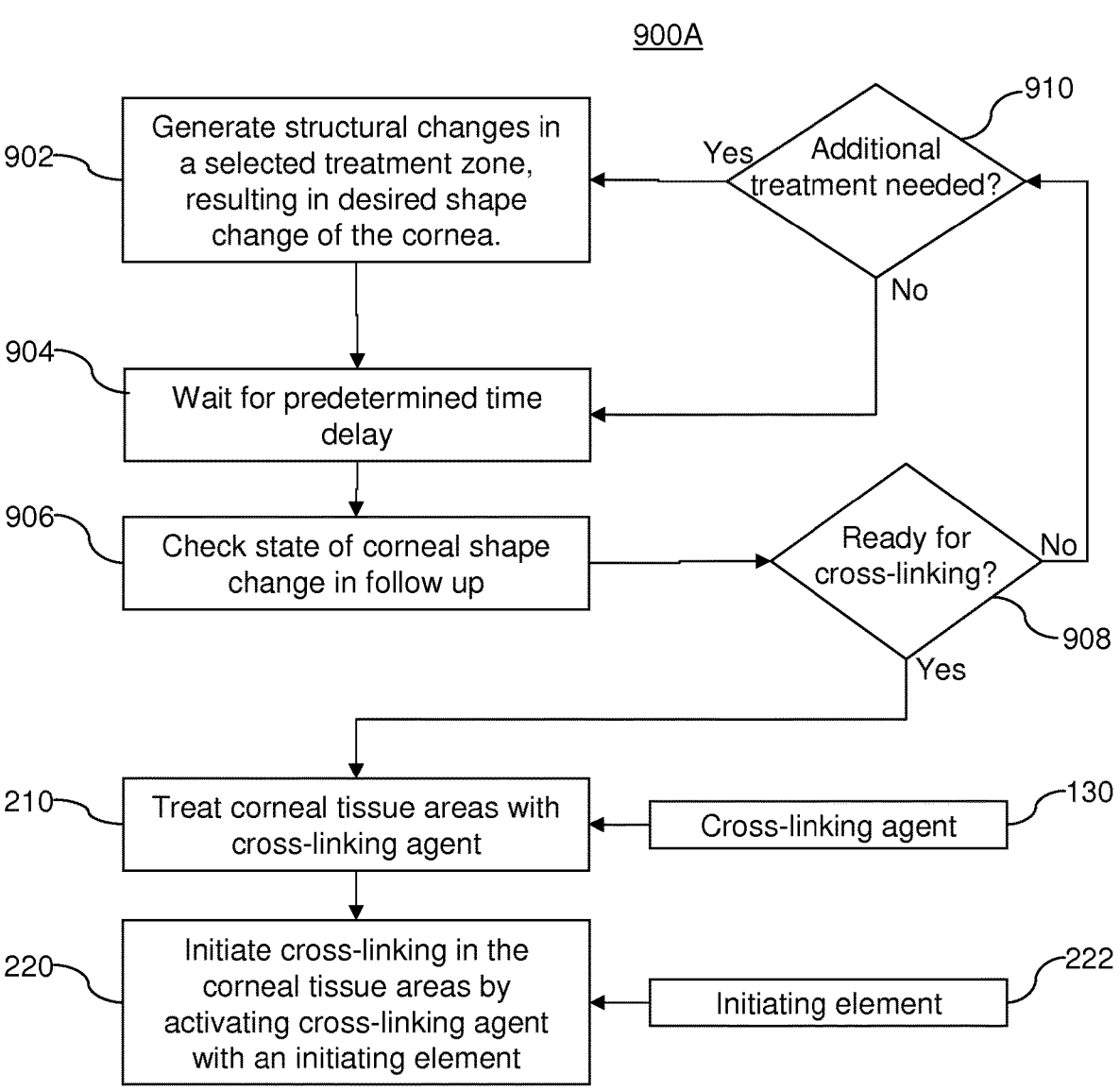
FIG. 9A provides a flowchart for activating the cross-linking agent in a staged procedure according to an aspect of the present disclosure.

FIG. 9A provides a flowchart for activating the cross-linking agent 130 in a staged procedure according to an aspect of the present disclosure. It is understood that the application of the cross-linking agent 130 and the activation of the cross-linking agent 130 described above may occur in a staged procedure. Referring to FIG. 9A, in step 902, heat is applied in a thermokeratoplasty treatment or LASIK surgery is performed to generate structural changes in the cornea 2 and produce a desired shape change in a treatment zone according to a desired pattern. In step 904, a predetermined amount of time passes. The predetermined amount of time can be, for example, a period of approximately one week and may correspond to a period of time between a patient's appointments with a doctor. In one or more steps 906 after the predetermined period of time of step 904, the changes to the corneal shape, e.g., refraction, are checked. The changes to the corneal shape can be checked with one or more of the feedback systems previously described, including a system for performing profilometry of the cornea 2, such as the interferometry systems of FIGS. 6A through 6E or the polarimetry systems of FIGS. 7B through 7E.

Figure 2C:
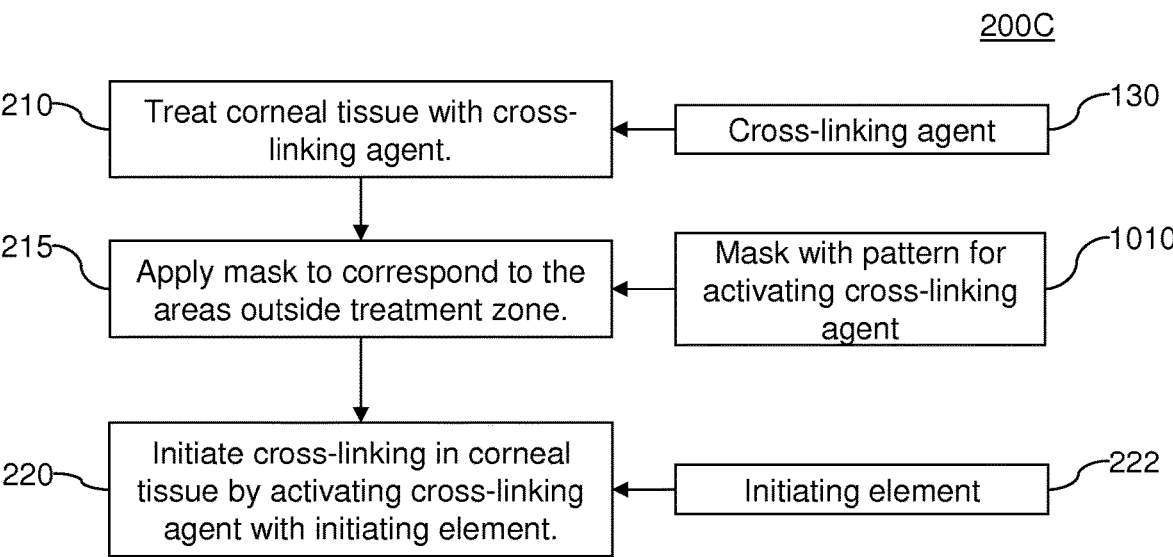
FIG. 2C provides a flowchart similar to FIG. 2A, but with an additional step for placing a mask on the eye described in FIGS. 10A and 10B.

The steps 906 may correspond to follow up, e.g., weekly, appointments with the patient after the treatment in step 902. When the patient and doctor are satisfied with the correction in vision in step 908 and it is determined the corneal structure is ready to be stabilized by cross-linking, cross-linking is generated in selected areas of the cornea 2 to stabilize the structural changes in steps 210 and 220, similarly to the techniques described in connection with FIG. 2. In some cases, the patient may be treated with a slight over-correction in step 902 to account for any reversal that may occur before the cross-linking is initiated. If necessary, additional treatment may be applied in step 902 according to decision step 910 after the treatment zone has been checked in step 906. It is noted that the staged procedure illustrated in FIG. 9A can be employed when cross-linking is activated within the treatment zone, or outside the treatment zone as described herein.

FIG. 9B provides a flowchart for using an interferometer to conduct pre-operative and post-operative examination of the corneal structure to be treated with LASIK surgery and the cross-linking agent 130. In step 912, a pre-operative examination of the eye 1 is performed. The pre-operative examination may be performed using any of the feedback systems discussed above, or may be performed according to conventional techniques for determining whether a patient requires LASIK surgery. In step 914, LASIK surgery is performed to achieve the shape change desired according to the pre-operative examination in step 912. In step 916, dynamic interferometry is employed (such as, e.g., the dynamic interferometry systems described in connection with FIGS. 6A through 6E) to determine initial structural measurements of the corneal tissue, and particularly to determine the biomechanical strength or stiffness of the corneal tissue. In steps 210 and 220, the corneal tissue is treated with the cross-linking agent 130 to and cross-linking is initiated in the corneal tissue with the initiating element 222. The determination of the corneal strength performed in step 916 may be used in part to adjust the amount of cross-linking treatment applied in step 210. In step 918, which may be similar to step 916, the corneal tissue is evaluated again with dynamic interferometry to determine the biomechanical strength of the corneal tissue. In step 920, it is determined if the measure of corneal strength or stiffness indicated in step 918 according to the dynamic interferometry system, is sufficient to halt further cross-linking treatment, or if cross-linking treatment should continue to further strengthen the corneal tissue. According to the outcome of the determination made in step 920, the cornea 2 may receive additional cross-linking therapy by a further application of the initiating element 222, and step 918 may be repeated once again. Alternatively, if it is determined in step 920 that the cornea 2 has been sufficiently strengthened by the cross-linking treatment received, then a post-operative examination of the eye 1 is conducted in step 922.

According to one approach, the Riboflavin may be the cross-linking agent 130, and may be applied topically to the corneal surface 2A, and transepithelial delivery allows the Riboflavin to be applied to the corneal stroma. In configurations where Riboflavin is the cross-linking agent 130, the application of the cross-linking agent 130 generally sufficiently introduces Riboflavin to mid-depth regions of the corneal tissue where stronger and more stable structure is desired.

Figure 9C:
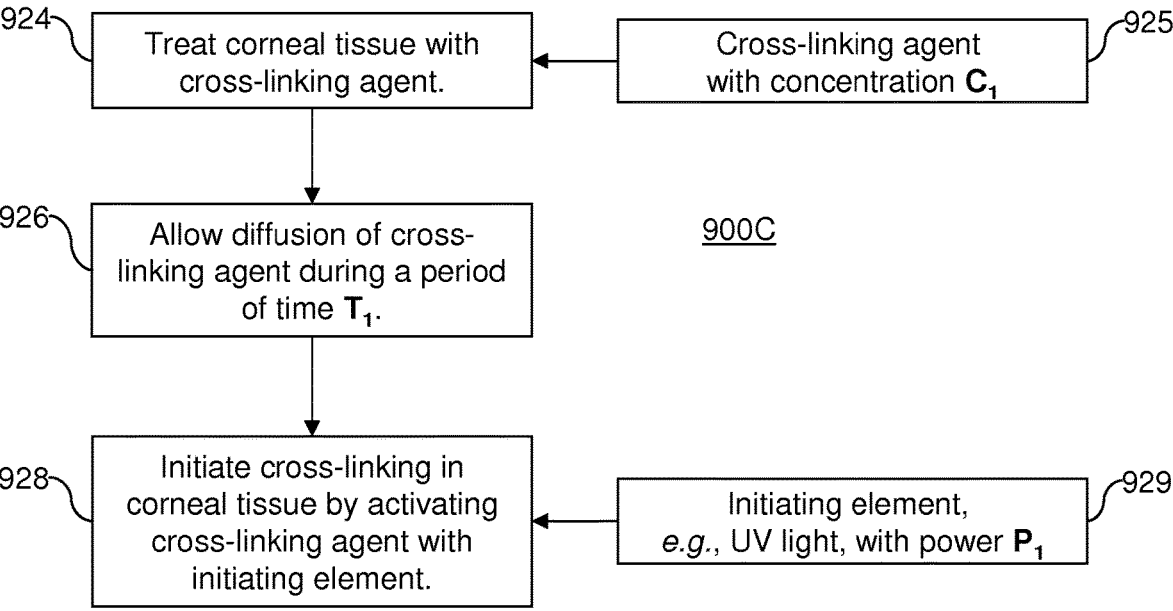
FIG. 9C provides an example embodiment for activating cross-linking while controlling the concentration of the cross-linking agent, the power of the initiating element, and the time delay between application and activation.

Referring to the example embodiment 900C shown in FIG. 9C, the cross-linking agent 925 having a concentration $C_1$ is applied to the cornea 2 in step 924. The cross-linking agent 925, for example, may be applied topically to the corneal surface 2A (e.g., the epithelium) of the cornea 2. In step 926, a period of time $T_1$ is allowed to pass. During the period of time $T_1$, the cross-linking agent 925 diffuses into the underlying corneal structure according to an exponential gradient. The distribution of cross-linking agent, i.e., concentration of cross-linking agent 925 at depths at and below the corneal surface 2A, depends at least on the concentration $C_1$ and the period of time $T_1$. The initiating element 929 is applied to the cornea in step 928 with a power $P_1$. As discussed above, in connection with FIG. 2, the initiating element 929 may be UV light. The power $P_1$ of the initiating element determines the extent to which the distribution of cross-linking agent 925 is activated. For example, an initiating element applied with a power greater than $P_1$ may reach greater depths below the corneal surface 2A and allow the cross-linking agent 925 to be activated at these depths. The power P1 may be selected according to the concentration $C_1$ and the time $T_1$. The parameters $C_1$, $P_1$, and $T_1$ may be selected to achieve the appropriate amount of cross-linking at desired depths of the cornea 2.

Figure 9D:
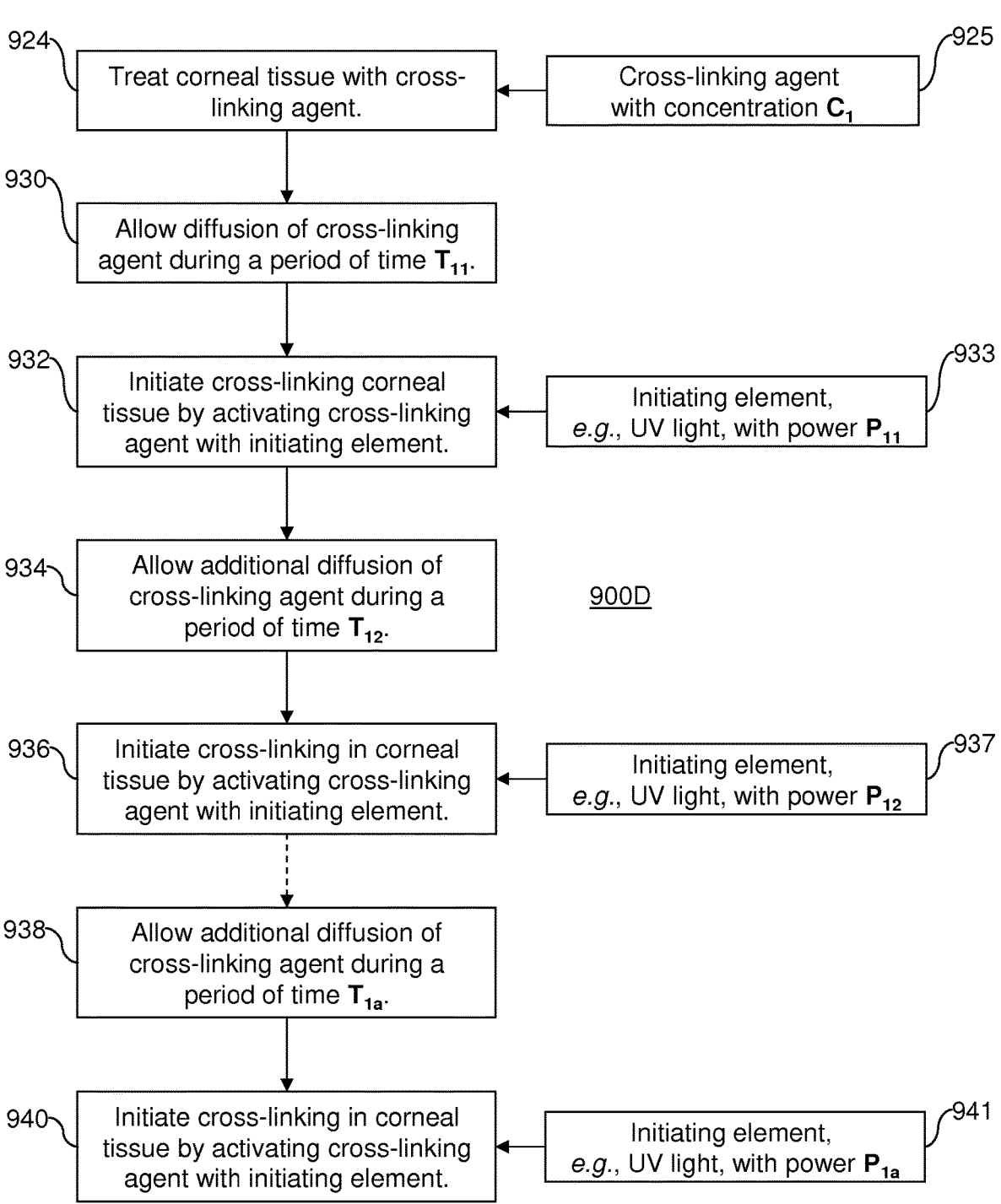
FIG. 9D provides an example embodiment for iteratively activating cross-linking and varying the power and time delay between incremental activations with the initiating element.

Referring to another embodiment 900D shown in FIG. 9D, the cross-linking agent 925 with a concentration $C_1$ is applied to the cornea in step 924. In step 930, the cross-linking agent 925 diffuses into the underlying corneal structure during a period of time $T_{11}$. The initiating element 933 with power $P_{11}$ is then applied to the cornea in step 932. Unlike the embodiment 900C described previously, however, the initiating element is also applied in one or more additional steps (936, 940) after additional periods of time are allowed to pass. For example, during step 934, the cross-linking agent 925 applied in step 924 diffuses farther into the underlying corneal structure during a second period of time $T_{12}$. The initiating element 933 with power $P_{12}$ is then applied to the cornea 2 in step 932 to provide further activation of the cross-linking agent 925. As illustrated in FIG. 9D, the initiating element may be applied in any number of additional steps. FIG. 9D illustrates the concluding steps 938 and 940 where the initiating element 941 with power $P_{1a}$ is finally applied after a period of time $T_{1a}$.

In general, each application of the initiating element occurs after periods of time $T_{11}$, $T_{12}$, ..., $T_{1a}$, respectively, have passed. During the periods of time $T_{11}$, $T_{12}$, ..., $T_{1a}$, the cross-linking agent diffuses to increasing depths in the underlying corneal structure, and is incrementally activated with each application of the initiating element with powers $P_{11}$, $P_{12}$, ..., $P_{1a}$. In other words, the cross-linking agent is activated as it moves to increasing depths in the cornea 2. The powers $P_{11}$, $P_{12}$, ..., $P_{1a}$ may include any combination of the same and/or different power values. The periods of time $T_{11}$, $T_{12}$, ..., $T_{1a}$ may include any combination of the same and/or different time values. The parameters $C_1$; $P_{11}$, $P_{12}$, ..., $P_{1a}$; and $T_{11}$, $T_{12}$, ..., $T_{1a}$ may be selected to achieve the appropriate amount of cross-linking at desired depths of the cornea 2. For example, the periods of time $T_{11}$, $T_{12}$, ..., $T_{1a}$ are selected to allow the desired amounts of cross-linking agent to reach targeted regions of the cornea 2.

Correspondingly, the powers $P_{11}$, $P_{12}$, ..., $P_{1a}$ are selected so that the desired amount of cross-linking is activated at these regions.

Figure 9E:
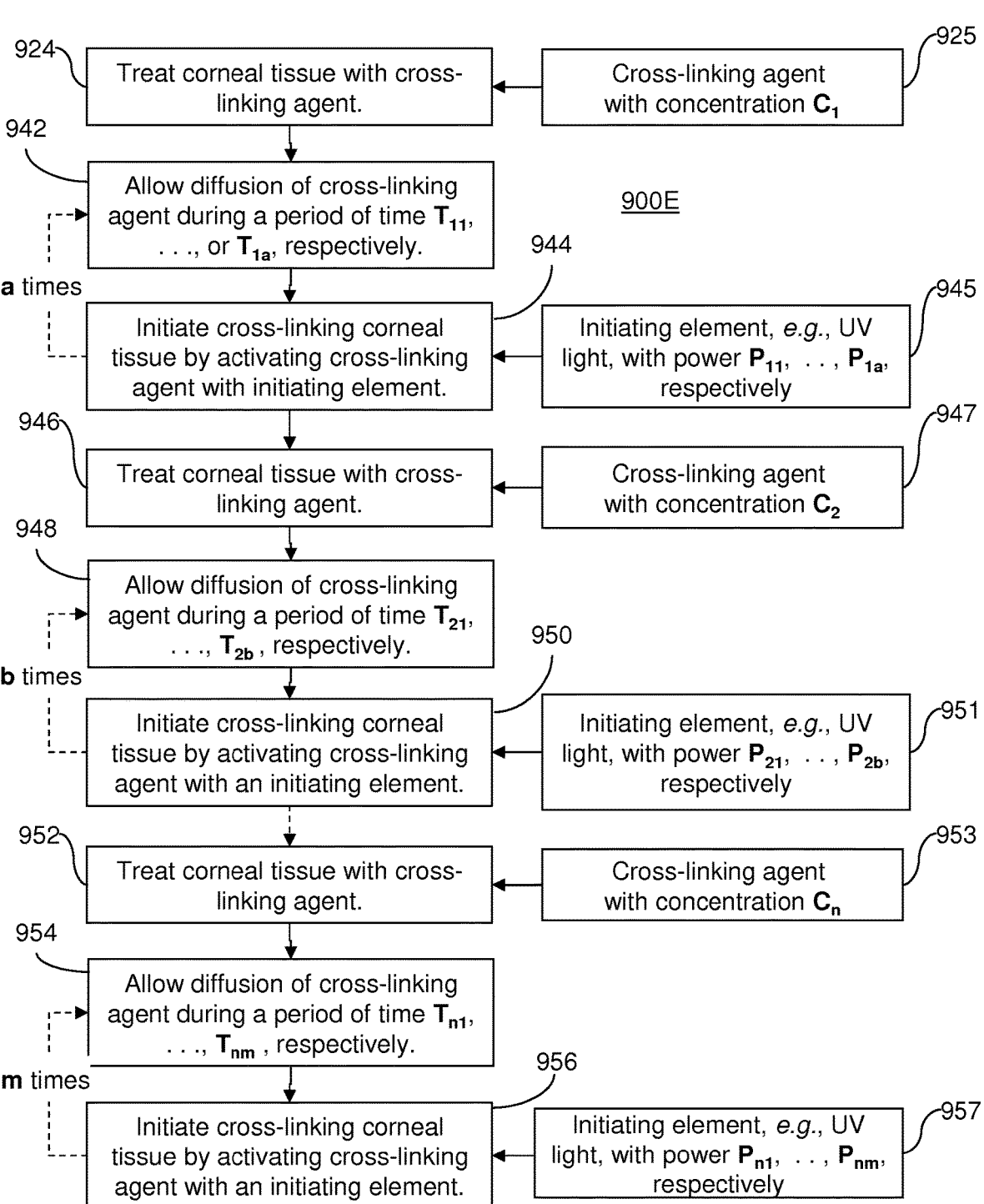
FIG. 9E provides an example embodiment for iteratively activating cross-linking similar to FIG. 9D, but where the cross-linking agent can be applied repeatedly and at different concentrations.

Referring to yet another embodiment 900E shown in FIG. 9E, the concentration of $C_1$ of the cross-linking agent 925 is applied to the cornea 2 in step 924. Similar to the embodiment 900D above, the initiating element 945 is applied one or more times in step 944 with powers $P_{11}$, $P_{12}$, ..., $P_{1a}$ after respective periods of time $T_{11}$, $T_{12}$, ..., $T_{1a}$ in step 942. However, in the embodiment 900E, additional concentrations $C_2$, ..., $C_n$ of the cross-linking agent (947, 953) may be applied to the cornea 2. For example, in step 946, the concentration of $C_2$ of the cross-linking agent 947 is applied to the cornea 2. The initiating element 951 is then applied one or more times in step 950 with powers $P_{21}$, $P_{22}$, ..., $P_{2b}$ after respective periods of time $T_{21}$, $T_{22}$, ..., $T_{2b}$ in step 948. Additional applications of the cross-linking agent may be applied until the final concentration $C_n$ of the cross-linking agent 953 is applied to the cornea 2 in step 952. The initiating element 957 is then applied one or more times in step 956 with powers $P_{n1}$, $P_{n2}$, ..., $P_{nm}$ after respective periods of time $T_{n1}$, $T_{n2}$, ..., $T_{nm}$ in step 954.

The concentrations $C_1$, $C_2$, ..., $C_n$ may include any combination of concentration values. For example, the concentrations $C_1$, $C_2$, ..., $C_n$ may be varied to combine varying distribution gradients and achieve a desired distribution of the cross-linking agent in the cornea 2. Each application of the concentrations $C_1$, $C_2$, ..., $C_n$ of the cross-linking agent may be activated by a single application of the initiating element after a period of time. In this case, the values of a, b, ..., m in FIG. 9E are equal to 1.

Alternatively, each application of the concentrations $C_1$, $C_2$, ..., $C_n$ may be activated by a series of applications of the initiating element with powers $P_{11}$, ..., $P_{1a}$; $P_{21}$, ..., $P_{2b}$; and $P_{n1}$ ..., $P_{nm}$, respectively. In this alternative case, the values of a, b, ..., m in FIG. 9E are greater than 1. However, in other embodiments, the values of a, b, ..., m may include other combinations of values. For example, a may equal 1 for a single application of the initiating element 945 for concentration $C_1$; b may equal 3 for three applications of the initiating element 951 for concentration $C_2$; ...; and m may equal 1 for a single application of the initiating element 957 for concentration $C_n$. Each application of the initiating element occurs after respective periods of time $T_{11}$, ..., $T_{1a}$; $T_{21}$, ..., $T_{2b}$; and $T_1$, ..., $T_{nm}$ to allow the cross-linking agent to move to increasing depths before being activated. For example, step The powers $P_{11}$, ..., $P_{1a}$; $P_{21}$, ..., $P_{2b}$; and $P_{n1}$, ..., $P_{nm}$ may include any combination of power values. The periods of time $T_{11}$, ..., $T_{1a}$; $T_{21}$, ..., $T_{2b}$; and $T_{n1}$, ..., $T_{nm}$ may include any combination of time values. The parameters $C_1$, $C_2$, ..., $C_n$, $P_{21}$, ..., $P_{2b}$; and $P_{n1}$, ..., $P_{nm}$; $T_{11}$, ..., $T_{1a}$; $T_{21}$, ..., $T_{2b}$; and $T_{n1}$, ..., $T_{nm}$ may be selected to achieve the appropriate amount of cross-linking at desired depths of the cornea 2. For example, the periods of time $T_{11}$, ..., $T_{1a}$; $T_{21}$, ..., $T_{2b}$; and $T_{n1}$, ..., $T_{nm}$ are selected to allow the desired amounts of cross-linking agent at concentrations $C_1$, $C_2$, ..., $C_n$ to reach targeted regions of the cornea 2. Correspondingly, the powers $P_{11}$, ..., $P_{1a}$; $P_{21}$, ..., $P_{2b}$; and $P_{n1}$, ..., $P_{nm}$ are selected so that the desired amount of cross-linking is activated at these regions. In general, varying the combination of concentrations, periods of time, and power allows the dosage of cross-linking to be spatially tailored.

The combination of concentrations, periods of time, and power may also be chosen based in part on feedback information 404 provided by the feedback system 400 shown in FIG. 4. In addition, the combination of concentrations, periods of time, and power may be computed by the controller 120 automatically based on the feedback information 404 or may be manually input by an operator (such as a doctor) after studying the feedback information 404. As described above, the feedback information 404 may include images from a video camera (FIG. 5A), from an interferometer (FIG. 6), from a polarimetry system (FIG. 7), or from any combination of these.

In some embodiments, the cross linking agent may be dissolved in a different carrier to promote delivery across the corneal surface 2A. For example, the cross-linking agent may be combined in varying concentrations with another agent, such as EDTA, benzalkonium chloride, or an alcohol, to promote further delivery across the corneal surface 2A.

In other embodiments, a second (neutral) compound may be applied after any of the concentrations $C_1$, $C_2$, . . . , $C_n$ of the cross-linking agent has been applied. The second compound applies a pressure to the cross-linking agent and promotes diffusion of the cross-linking agent to depths of the cornea 2. For example, in FIG. 9F, which provides an embodiment 900F similar to the embodiment 900C, the neutral compound 959 is applied in step 958 after the cross-linking agent 925 has been applied. However, the neutral compound 959 may be applied at any time during the embodiments described herein. For example, the neutral compound 959 may be applied at a time when diffusion of the cross-linking agent has slowed and needs to be encouraged by the neutral compound.

In embodiments where the initiating element is UV light, the UV light is applied according to frequencies (or wavelengths) that correspond with an absorption spectrum of the cross-linking agent, e.g., Riboflavin. Effective absorption of the UV light by the cross-linking agent results in activation of the cross-linking agent. The absorption spectrum indicates the amount of absorption exhibited by a given concentration of cross-linking agent as a function of frequency. An absorption peak in the absorption spectrum indicates the frequencies at which the UV light is most effectively absorbed by the cross-linking agent.

In some cases, a spectrophotometer may be employed to apply the UV light according to frequencies within a narrow bandwidth, e.g., approximately 0.1 nm resolution. The Beer-Lambert law states that the absorption of the UV light is directly proportional to the concentration of the absorbing material. At sufficiently high concentrations, however, the absorption spectra show absorption flattening, where the absorption peak appears to flatten because close to 100% of the UV light is already being absorbed (saturation). The phenomenon of absorption flattening can result in deviations from the Beer-Lambert law. Such deviation may occur when concentrations of cross-linking agent used in the embodiments are exposed to a narrow bandwidth of frequencies, e.g., approximately 0.1 nm resolution. With this narrow bandwidth, saturation occurs and the cross-linking agent reaches a point where no more UV light can be absorbed.

Alternatively, a light-emitting diode (LED) may be employed to apply the UV light to the cross-linking agent. The bandwidth of frequencies from the LED is typically broader than the bandwidth of frequencies from the spectrophotometer. For example, the resolution from the LED may be approximately 10 nm. The absorption behavior is different when the greater resolution of the LED is employed. The activation of the cross-linking agent increases with the absorption of additional frequencies in the bandwidth. Accordingly, the absorption may be controlled by increasing the bandwidth of the excitation source (e.g., the light source 110 in FIG. 1), particularly as a function of concentration of the cross-linking agent (or corneal depth as described previously).

Figure 9G:
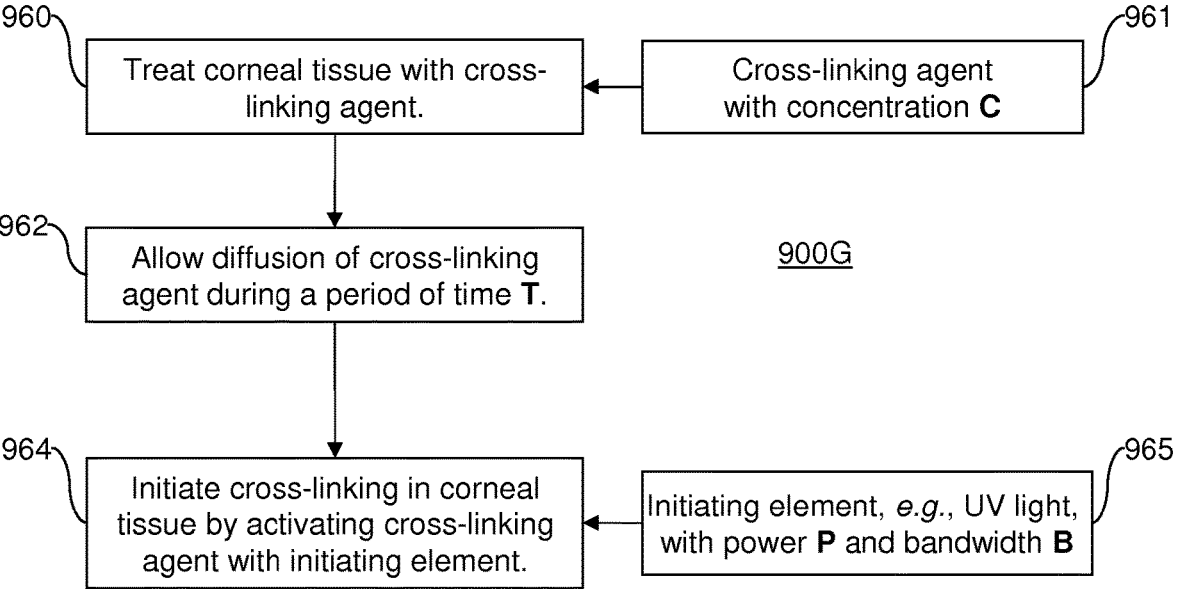
FIG. 9G provides an example embodiment similar to the embodiment shown in FIG. 9C, and where the bandwidth of the initiating element is also controlled.

Referring to the example embodiment 900G shown in FIG. 9G, the cross-linking agent 961 is applied to the cornea 2 in step 960 with a concentration C. The cross-linking agent 961, for example, may be applied topically to the corneal surface 2A of the cornea 2. In step 962, a period of time T is allowed to pass. During the period of time T, the cross-linking agent 961 diffuses into the underlying corneal structure according to an exponential gradient. The distribution of cross-linking agent, i.e., concentration of cross-linking agent at depths at and below the epithelium, depends at least on the concentration C and the period of time T. The initiating element 965 is applied to the cornea 2 in step 964. As discussed above, the initiating element 965 may be UV light. As such, the initiating element 965 in FIG. 9G is applied with a power P and a bandwidth B. The power P and bandwidth B with which the initiating element is applied determines the extent to which the distribution of cross-linking is activated.

For example, an initiating element applied with a power greater than P may reach greater depths below the corneal surface 2A and allow the cross-linking agent to be activated at these depths. Additionally, an initiating element applied according to a relatively greater bandwidth B of frequencies, e.g., from an LED source with approximately 10 nm resolution, results in greater absorption of the UV light and activation of the cross-linking agent. The selection of the power P and bandwidth B may depend on the concentration C and the time T. The parameters C, P, T, and B may be selected to achieve the appropriate amount of cross-linking at desired depths of the cornea.

As described previously with reference to FIGS. 9D and 9E, the initiating element may be applied in one or more additional steps after additional applications of cross-linking agent at one or more concentrations and/or after one or more periods of time to allow the cross-linking agent to diffuse into the corneal tissue. In addition to selecting a power for each application of the initiating element, the initiating element, e.g., UV light, may be applied in the examples above according to one or more selected bandwidths to control the activation of the cross-linking agent further.

In embodiments where the initiating element is UV light, the UV light may be delivered with laser scanning technologies, such as by a laser scanning device 300 described in connection with FIG. 3. For example, embodiments may employ aspects of single photon laser scanning or Digital Light Processing™ (DLP®) technologies. Advantageously, the use of laser scanning technologies allows cross-linking to be activated more effectively beyond the surface of the cornea 2, at depths where stronger and more stable corneal structure is desired. In particular, treatment may activate cross-linking at a mid-depth region after the cross-linking agent has moved to this region through diffusion after a period of time. Thus, the application of the initiating element may be applied precisely according to a selected three-dimensional pattern. The power and bandwidth with which the UV light is applied determines in part how deeply the scanning laser penetrates into the cornea 2, and as such, may be varied as described previously.

In sum, embodiments stabilize a three-dimensional structure of corneal tissue through controlled application and activation of cross-linking in the corneal tissue. For example, the cross-linking agent and/or the initiating element are applied in a series of timed and controlled steps to activate cross-linking incrementally. Moreover, the delivery and activation of the cross-linking agent at depths in the cornea 2 depend on the concentration(s) of the cross-linking agent and the power(s) of the initiating element.

Furthermore, embodiments provide systems, methods, and devices for monitoring cross-linking activity in the cornea 2 and for monitoring the position of the cornea 2 and the biomechanical strength of the cornea 2. In embodiments employing any of the incremental approaches to providing eye therapy and activating cross-linking shown in FIGS. 9A through 9G, the incremental steps may be informed, at least in part, by feedback information 404 from the feedback system 400. The various choices in the incremental approach relating to decisions whether to perform additional eye therapy or cross-linking treatment can be determined partially or completely based on the feedback information 404 from the feedback system 400. Additionally, the various choices relating to the proper amounts of eye therapy treatment, the concentrations of the cross-linking agent 130, the power, bandwidth, duration, and time delay of the initiating element 222 can each be determined partially or completely based on the feedback information 404 from the feedback system 400. As described above, the feedback system 400 may include a video camera, an interferometer, a polarimetry system, a wavefront sensor, a Shack-Hartmann sensor, or any combination of these.

In a still further embodiment of the incremental approaches for activating cross-linking in the cornea 2 and employing the feedback system 400, the controller 120 may automatically determine adjustments to parameters (e.g., power, bandwidth, time delay duration, concentration, etc.). Furthermore, the controller 120 may be adapted to activate the cross-linking agent in incremental steps according to the automatically determined adjustments without intervention from a user of the system. Alternatively, the controller 120 may be adapted to automatically determine the adjustments and to prompt the user before activating the cross-linking agent before each incremental step, or may prompt the user after a pre-determined number of incremental activations with no user intervention. The prompt may display, for example, the proposed parameters with which to apply the next incremental step(s) and allow the user to either approve, deny, or modify the proposed automatically determined parameters. In an implementation, the prompt may be displayed via a user interface system coupled to the controller 120.

Embodiments may apply a mask to ensure that cross-linking activity is limited to selected areas of the cornea. As illustrated in the system 1000 in FIG. 10A, a mask 1010 may be positioned over the corneal surface 2A before the initiating element 222, i.e., the UV light, from the light source 110 is applied. FIG. 10B illustrates an example pattern 1014 for the mask 1010. In particular, the mask 1010 may be a device similar to a contact lens that is approximately 5 mm in diameter. In an example, a zone of structural changes in the cornea 2 may be in an annular pattern. To stabilize the structural changes in the treatment zone, cross-linking is initiated outside this annular treatment zone. For example, cross-linking may be initiated in areas in the center and/or periphery of this annular treatment zone. Cross-linking in the areas outside the annular treatment zone provides the corresponding corneal tissue with sufficient strength to stabilize the changes to the new structure in the annular treatment zone. Thus, cross-linking does not have to be initiated directly in the annular treatment zone to preserve the structural changes in the annular treatment zone.

Figure 10A:
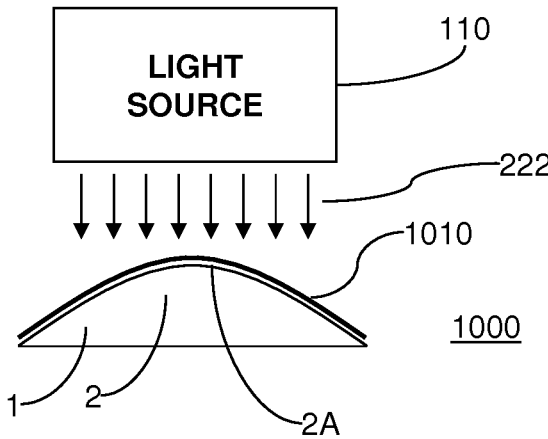
FIG. 10A illustrates a system having a mask positioned over the corneal surface to control the application of the initiating element.
Figure 10B:
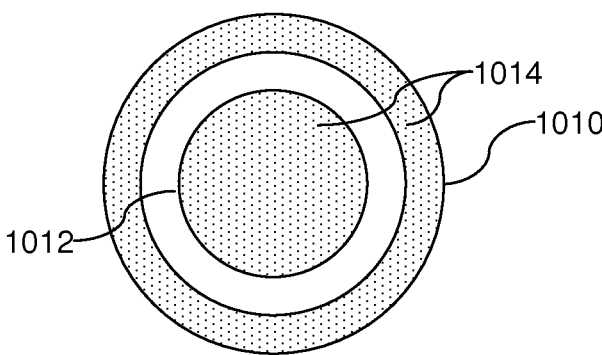
FIG. 10B illustrates an example pattern for the mask.

As a result, the mask 1010 of FIG. 10A only allows UV light from the light source 110 to pass to the cornea 2 and the cross-linking agent 130, e.g., Riboflavin, is activated in areas outside the treatment zone according to the pattern 1014. In particular, a UV-blocking material 1012 helps to define the pattern 1014 on the mask 1010. This UV-blocking material 1012 corresponds with the treatment zone to minimize the activation of cross-linking within the treatment zone. In alternative embodiments, the pattern 1014 may be structurally defined as a cut-out from the mask 1010. In any case, any UV light from the light source 110 outside this pattern 1014 is blocked by the mask 1010. Accordingly, the mask 1010 provides more precise activation of the cross-linking agent 130. Accordingly, referring to FIG. 2C, the cross-linking agent 130 in step 210 may be applied more broadly to the corneal surface 2A. With the appropriate delivery of the cross-linking agent 130 to the stroma, the mask 1010 is applied to the eye 1 in step 215 and the initiating element 222 is delivered in step 220 to initiate cross-linking according to the pattern in the mask 1010. In other words, the controlled application of the initiating element 222 determines the areas of cross-linking.

Although the mask 1010 is employed to deliver the initiating element 222 to the cornea 2 according to a particular pattern, masks may also be employed in some embodiments to deliver the cross-linking agent according to the specific pattern. Thus, the light source 110 of the initiating element 222 shown in FIG. 10A would be replaced by a source of the cross-linking agent 130 (such as the applicator 132 of FIG. 1).

Figure 11A:
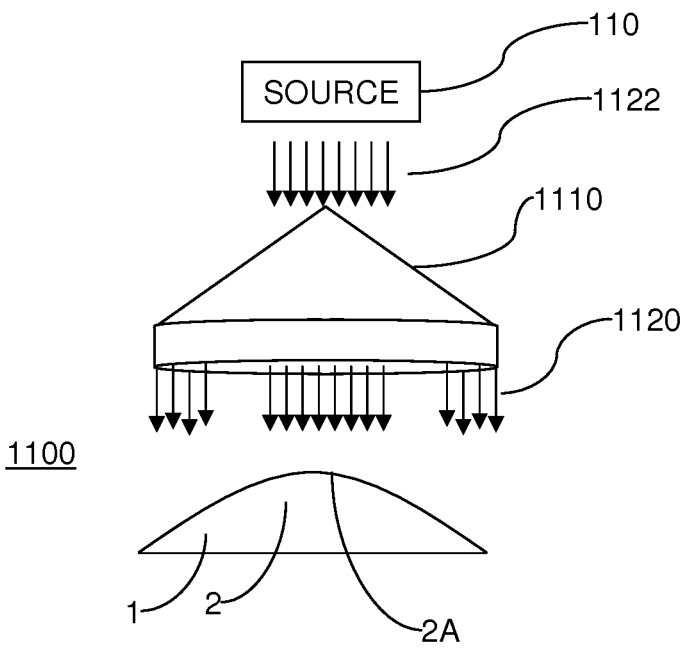
FIG. 11A illustrates a system having an optical element positioned between the light source and the eye for applying light to an eye according to a desired pattern.
Figure 11B:
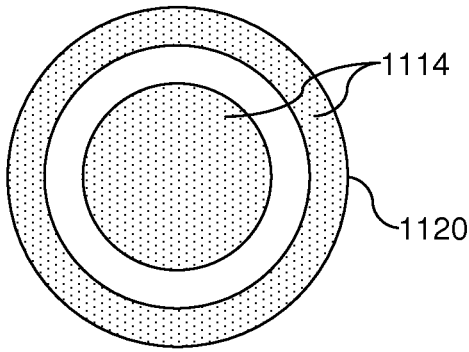
FIG. 11B illustrates an example desired pattern for applying the initiating element to the eye.

Moreover, although the system 1000 may employ a mask 1010, the devices employed for patterned initiation of a cross-linking agent is not limited to the use of such masks. Embodiments include more general systems and methods that activate a cross-linking agent according to a precise pattern, regardless of the type of device that actually directs the initiating element to specific areas of the cornea. For example, as shown in FIG. 11A, a system 1100 transforms the initiating element 222, e.g., UV light, from the light source 110 to define a desired pattern 1114 as shown in FIG. 11B. In contrast to the system 1000, the system 1100 does not block the initiating element 222 from the light source 110 from reaching areas outside a pattern. As illustrated in FIG. 11A, an optical device 1110 receives UV light as a collimated beam 1122 from the light source 110 and transforms the collimated beam 1122 into the desired pattern of light 1120. The pattern of light 1120 thus delivers the UV light to the cornea 2 according to a pattern 1114 that corresponds to areas outside the treatment zone. In other words, the pattern 1114 matches the areas where initiation of the cross-linking agent is desired. In general, any number or types of optical devices, such as lenses, beam-splitters, and the like, may be employed to achieve the desired shape for delivering an initiating element. Moreover, in some embodiments, the use of a mask 1010 as illustrated in FIG. 10A may be combined with the use of an optical device 1110.

Although cross-linking agents, such as Riboflavin, may be effectively applied to the stroma by removing the overlying epithelium before application, it has been shown that cross-linking agents can chemically transition across the epithelium into the stroma. Indeed, Riboflavin may also be delivered to the stroma by applying it topically on the epithelium. Moreover, in some cases, the epithelium may be treated to promote the transition of the cross-linking agent through the epithelium. Accordingly, in the embodiments described herein, no removal of the epithelium is required. Advantageously, this eliminates the post-operative pain, healing period, and other complications associated with the removal of the epithelium.

The use of Riboflavin as the cross-linking agent and UV light as the initiating element in the embodiments above is described for illustrative purposes only. In general, other types of cross-linking agents may be alternatively or additionally employed according to aspects of the present disclosure. Thus, for example Rose Bengal (4,5,6,7-tetrachloro-2',4',5',7'-tetraiodofluorescein) may be employed as the cross-linking agent 130, or as the cross-linking agent delivered in varying concentrations 925, 947, 953. Rose Bengal has been approved for application to the eye as a stain to identify damage to conjunctival and corneal cells. However, Rose Bengal can also initiate cross-linking activity within corneal collagen to stabilize the corneal tissue and improve its biomechanical strength. Like Riboflavin, photoactivating light may be applied to initiate cross-linking activity by causing the Rose Bengal to convert $O_2$ in the corneal tissue into singlet oxygen. The photoactivating light may include, for example, UV light or green light. The photoactivating light may include photons having energy levels sufficient to individually convert $O_2$ into singlet oxygen, or may include photons having energy levels sufficient to convert $O_2$ into singlet oxygen in combination with other photons, or any combination thereof.

As described herein, aspects of the present disclosure may be employed in combination with LASIK surgery. In LASIK surgery, an instrument called a microkeratome is used to cut a thin flap in the cornea. The flap is peeled back and the underlying corneal tissue is reshaped by the application of an excimer laser. After the desired reshaping of the cornea is achieved, the cornea flap is put back in place to complete the surgery. According to aspects of the present disclosure, a cross-linking agent is applied to the regions of the cornea treated by the LASIK surgery.

In one embodiment, the outer surface of the cornea, e.g., in the area of the flap, is treated with a cross-linking agent, e.g., Riboflavin, after the flap is put back in place. The cross-linking agent is then activated with an initiating element. Activation of the cross-linking agent, for example, may be triggered thermally by the application of microwaves or light to corresponding areas of the cornea. Cross-linking occurs in the area of application. Although the cross-linking agent is applied to the outer surface of the cornea, i.e., the epithelium, it has been shown that cross-linking agents can chemically transition across the outer surface into the underlying corneal tissue, i.e., the stroma. Thus, in some embodiments, the cross-linking agent may be delivered to the underlying corneal tissue by applying the cross-linking agent topically to the outer surface of the cornea. Moreover, in further embodiments, the outer surface may be treated to promote the transition of the cross-linking agent therethrough.

In another embodiment, after the flap is peeled back, inner surfaces of the cornea are exposed for the application of a cross-linking agent. In particular, the inner surface of the flap as well as the underlying corneal tissue are exposed. Therefore, the inner surface of the flap and/or the underlying corneal tissue are treated with a cross-linking agent. In other words, the cross-linking agent may be applied to (i) the inner surface of the flap only, (ii) the underlying corneal tissue only, or (iii) both the inner surface of the flap and the underlying corneal tissue. The cross-linking agent is then activated with an initiating element. Again, activation of the cross-linking agent may be triggered thermally by the application of microwaves or light. Although the initiating element may be applied before the flap is put back, the initiating element additionally or alternatively may be applied to the treated areas after the flap is put back in place. In this case, the initiating element can be delivered through the outer surface of the cornea.

According to yet another embodiment, the inner surface of the flap and/or the underlying corneal tissue are treated with a cross-linking agent after the flap is peeled back. The cross-linking agent is then activated with an initiating element. As in the previous embodiment, the cross-linking agent may be applied to (i) the inner surface of the flap only, (ii) the underlying corneal tissue only, or (iii) both the inner surface of the flap and the underlying corneal tissue. In addition, the outer surface of the cornea, e.g., in the area of the flap, is treated with a cross-linking agent after the flap is put back in place. The cross-linking agent is then activated in step with an initiating element. Again, activation of the cross-linking agent may be triggered thermally by the application of microwaves or light. In a variation of this embodiment, the cross-linking agent may be activated with an initiating element according to a single act, rather than two separate acts. Thus, the initiating element may be delivered in the single act after the flap is put back in place.

Accordingly, a cross-linking agent may be applied and activated in different regions at different points during LASIK treatment. For example, the cross-linking agent may be applied to any combination of the outer surface of the cornea, the inner surface of the flap, and the exposed underlying corneal tissue. Moreover, specially tailored concentrations of cross-linking agent may be applied in combination with varying levels of initiating element to these regions to achieve the appropriate amount of stability and strength in the cornea.

Figure 12A:
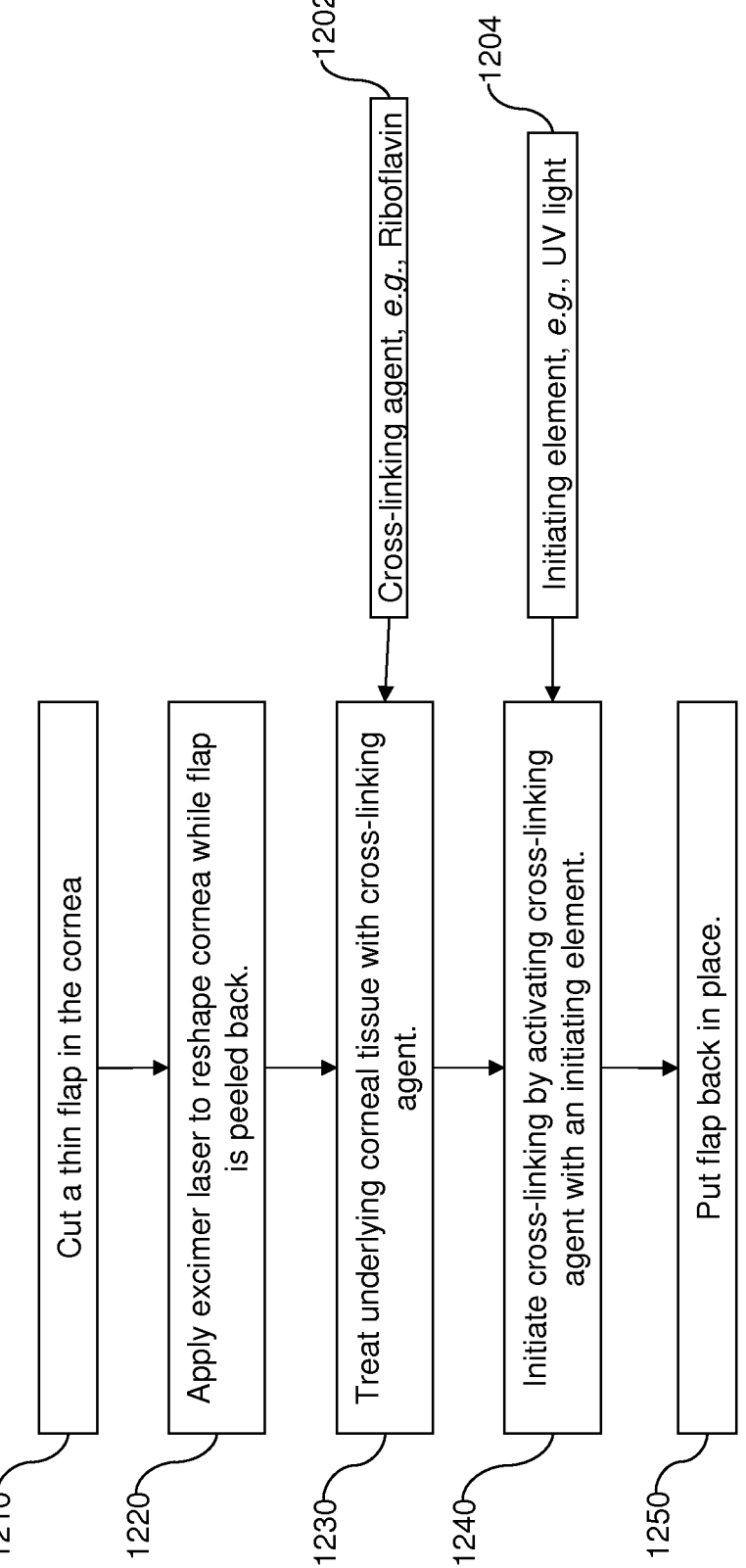
FIG. 12A illustrates an example approach for stabilizing changes in corneal structure after LASIK treatment.

FIG. 12A illustrates the activation of cross-linking in the regions of the cornea treated by the LASIK surgery. After the flap is peeled back in act 1210, inner surfaces of the cornea are exposed for the application of a cross-linking agent. In particular, the underlying corneal tissue is exposed. Therefore, in act 1230, the underlying corneal tissue is treated with a cross-linking agent 1202 after act 1220. The cross-linking agent 1230 may be applied, for example, by dripping a measured amount and concentration of the cross-linking agent 1202 topically onto the exposed underlying corneal tissue. The cross-linking agent 1202 is then activated in act 1240 with an initiating element 1204 while the flap remains peeled back. Activation of the cross-linking agent 1202 may be triggered thermally by the application of microwaves or light.

In an example embodiment, Ribloflavin may be applied as the cross-linking agent 1202 to the corneal tissue. In addition, a photoactivating light, such as ultraviolet (UV) light, may be applied as an initiating element 1204 to initiate cross-linking in the corneal areas treated with Ribloflavin. To achieve optimal results, an appropriate amount of Riboflavin is applied to the targeted regions of the cornea and an appropriate amount of UV light is applied to match the application of Riboflavin. In some cases, damage to the eye may result if too much Riboflavin and UV light reach the endothelium. This may occur, in particular, if too much time passes between the application of the Riboflavin in act 1230 and the application of the UV light in act 1240. The passage of time allows the Riboflavin to diffuse more deeply into the corneal tissue to the endothelium, and the UV light may reach the Riboflavin at the endothelium.

Figure 12B:
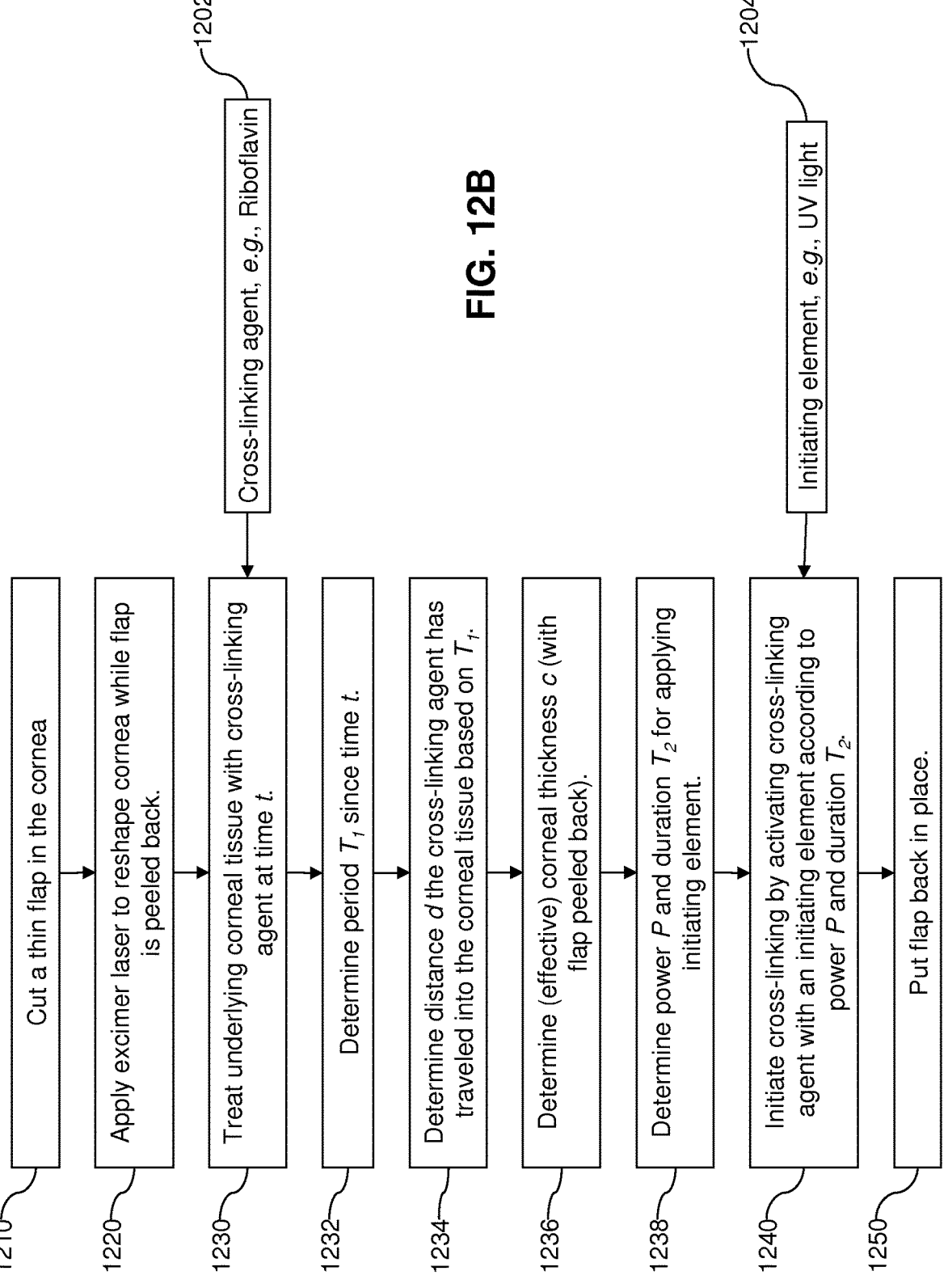
FIG. 12B illustrates another example approach for stabilizing changes in corneal structure after LASIK treatment.

Thus, according to aspects of the present invention further illustrated in FIG. 12B, embodiments apply the UV light in act 1240 according to a power and duration that ensure that the application of the UV light does not damage the endothelium. The resulting energy determines the depth to which the UV light penetrates in the corneal tissue. The power and duration are based in part on the amount of time that has passed since the application of the cross-linking agent. Because the rate of diffusion for a given concentration of the cross-linking agent is known, embodiments can use the time data to calculate how far the cross-linking agent has traveled into the corneal tissue. Therefore, in act 1232, a time period $T_1$ is determined from the time t when the cross-linking agent 1202 is applied in act 1230. Based on this time period $T_1$, a distance d representing how far the cross-linking agent has traveled into the corneal tissue is determined in act 1234.

Moreover, the power and duration are also based on the distance that the cross-linking agent and the UV light can travel though the cornea before reaching the endothelium. This distance generally corresponds with the thickness of the cornea. Therefore, in act 1236, the corneal thickness c is determined. By determining the diffusion distance d of the cross-linking agent and determining the thickness c of the cornea, the appropriate power P and duration $T_2$ can be determined in act 1238. The embodiments can apply the UV light to the cross-linking agent in the cornea in act 1240 while preventing damage to the endothelium.

When the cross-linking agent is applied and activated while the corneal flap remains peeled back during LASIK surgery, the amount of corneal tissue through which the cross-linking agent and the UV light can travel decreases. The risk of damage to the endothelium may be greater during LASIK surgery. Thus, to ensure that the UV light does not reach the endothelium, act 1236 may determine an "effective" thickness c by adjusting for the fact that the corneal flap is peeled back. For example, peeling back the flap may reduce the effective thickness of the cornea to 120 μm, and embodiments may apply the UV light according to a power P and duration $T_2$ that delivers the UV light to a depth of 100 μm.

Figure 13:
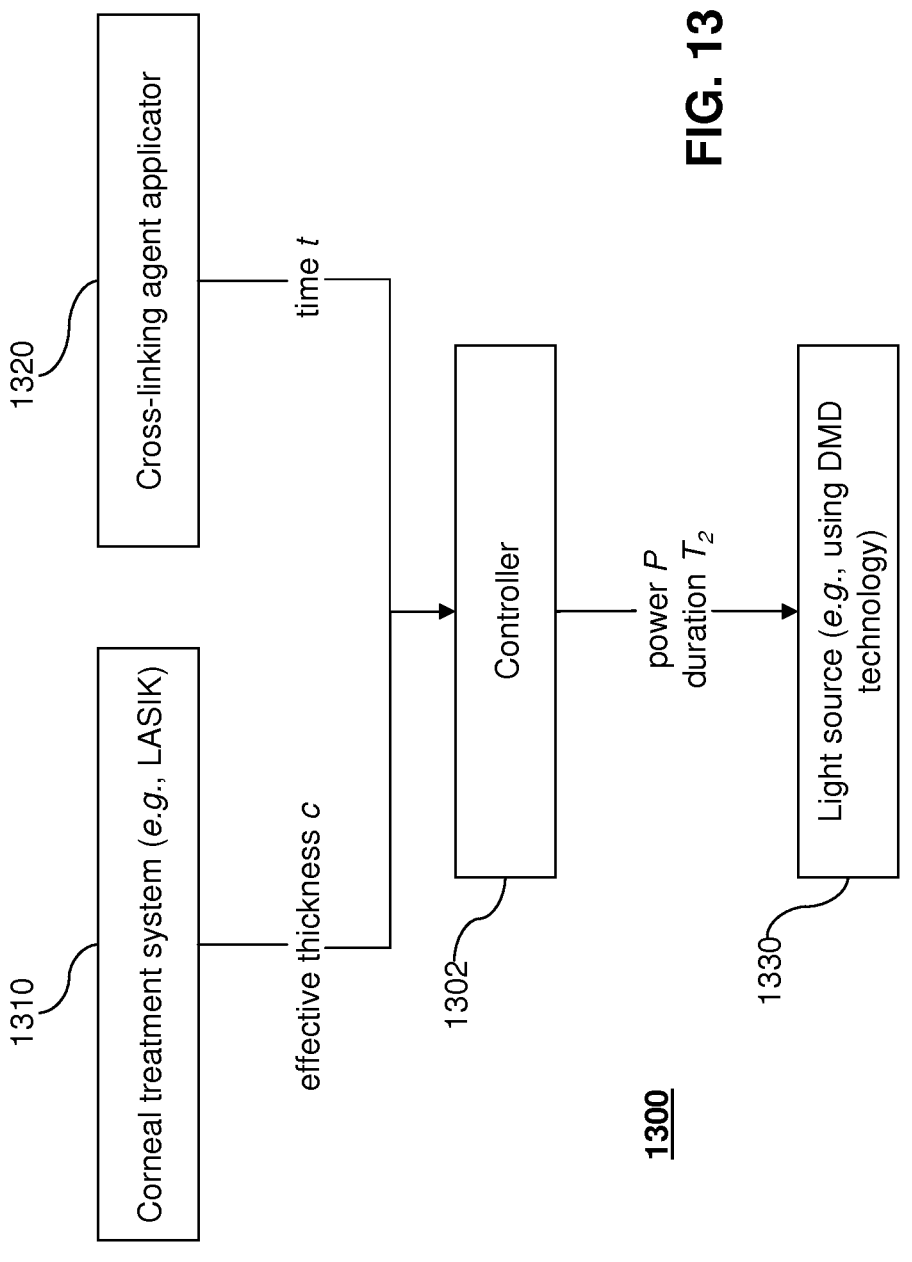
FIG. 13 illustrates an example system for stabilizing changes in corneal structure after eye treatment.

Referring to FIG. 13, an embodiment 1300 may employ a corneal treatment system 1310 (e.g., for applying LASIK surgery), a cross-linking agent applicator 1320 (e.g., for applying Riboflavin to the cornea), and a light source 1330 (e.g., for delivering the UV light to the cornea). Advantageously, aspects of the present invention integrate the operation of the treatment system 1310, the cross-linking agent applicator 1320, and the light source 1330. A controller 1302, e.g., a computer or other processing device, receives input data from the treatment system 1310 and the cross-linking agent applicator 1320 and determines parameters for the operation of the light source 1330. In particular, the controller 1302 determines the appropriate power P and duration $T_2$ for the controlled light source 1330 to apply light to activate the cross-linking agent.

Referring to FIG. 13, the treatment system 1310 creates a flap that is peeled back and reduces the cornea's effective thickness c, and the cross-linking agent applicator applies the cross-linking agent at a particular time t. The controller 1302 receives the effective thickness c and the time t as input data. Applying the process described in FIG. 12B, the controller 1302 then determines the appropriate power P and duration $T_2$ for the application of the light by the light source 1330.

Although embodiments of the present disclosure may describe stabilizing corneal structure after treatments, such as LASIK surgery and thermokeratoplasty, it is understood that aspects of the present disclosure are applicable in any context where it is advantageous to form a stable three-dimensional structure of corneal tissue through cross-linking.

The present disclosure includes systems having controllers for providing various functionality to process information and determine results based on inputs. Generally, the controllers (such as the controller 120 described throughout the present disclosure) may be implemented as a combination of hardware and software elements. The hardware aspects may include combinations of operatively coupled hardware components including microprocessors, logical circuitry, communication/networking ports, digital filters, memory, or logical circuitry. The controller may be adapted to perform operations specified by a computer-executable code, which may be stored on a computer readable medium.

As described above, the controller 120 may be a programmable processing device, such as an external conventional computer or an on-board field programmable gate array (FPGA) or digital signal processor (DSP), that executes software, or stored instructions. In general, physical processors and/or machines employed by embodiments of the present disclosure for any processing or evaluation may include one or more networked or non-networked general purpose computer systems, microprocessors, field programmable gate arrays (FPGA's), digital signal processors (DSP's), micro-controllers, and the like, programmed according to the teachings of the exemplary embodiments of the present disclosure, as is appreciated by those skilled in the computer and software arts. The physical processors and/or machines may be externally networked with the image capture device(s) (e.g., the CCD detector 660, camera 760, or camera 860), or may be integrated to reside within the image capture device. Appropriate software can be readily prepared by programmers of ordinary skill based on the teachings of the exemplary embodiments, as is appreciated by those skilled in the software art. In addition, the devices and subsystems of the exemplary embodiments can be implemented by the preparation of application-specific integrated circuits or by interconnecting an appropriate network of conventional component circuits, as is appreciated by those skilled in the electrical art(s). Thus, the exemplary embodiments are not limited to any specific combination of hardware circuitry and/or software.

Stored on any one or on a combination of computer readable media, the exemplary embodiments of the present disclosure may include software for controlling the devices and subsystems of the exemplary embodiments, for driving the devices and subsystems of the exemplary embodiments, for enabling the devices and subsystems of the exemplary embodiments to interact with a human user, and the like. Such software can include, but is not limited to, device drivers, firmware, operating systems, development tools, applications software, and the like. Such computer readable media further can include the computer program product of an embodiment of the present disclosure for performing all or a portion (if processing is distributed) of the processing performed in implementations. Computer code devices of the exemplary embodiments of the present disclosure can include any suitable interpretable or executable code mechanism, including but not limited to scripts, interpretable programs, dynamic link libraries (DLLs), Java classes and applets, complete executable programs, and the like. Moreover, parts of the processing of the exemplary embodiments of the present disclosure can be distributed for better performance, reliability, cost, and the like.

Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the present disclosure has been described in connection with a number of exemplary embodiments, and implementations, the present disclosure is not so limited, but rather cover various modifications, and equivalent arrangements.

What is claimed is:

1. A system for activating a cross-linking agent applied to a cornea of an eye, comprising:

a light source including a light emitting diode for emitting a non-ablative photoactivating light, the light source emitting linearly polarized light or a beam of light capable of being filtered to pass linearly polarized light;

a digital micromirror device (DMD) including a plurality of mirrors arranged in a matrix, the plurality of mirrors configured to selectively reflect the photoactivating light from the light source to provide a pixelated illumination to be directed to a cornea of an eye, the pixelated illumination including pixels defined by the mirrors in the DMD;

one or more optical elements positioned to direct the pixelated illumination from the DMD to the cornea;

a controller configured to control the DMD to programmatically select which of the mirrors reflect the photoactivating light to provide the pixelated illumination to a selected region of the cornea, wherein, at one particular instant in time, the pixelated illumination is defined by a two-dimensional array of the pixels, the controller being configured to control the light source to determine a duration for the pixelated illumination to generate cross-linking activity in the selected region of the cornea; and a feedback system configured to provide the controller with feedback information for controlling the DMD, the feedback system including an eye-tracking system having a video camera, wherein the feedback system is further configured to measure changes in biomechanical strength or stiffness in response to a corneal deflection, and wherein the controller is further configured to determine an amount of cross-linking based on the feedback information, and controlling the light source comprises modulating the DMD spatially and temporally at least partially based on the determination.

2. A system for activating a cross-linking agent applied to a cornea of an eye, comprising:

a light source including a light emitting diode for emitting a non-ablative photoactivating light, the light source emitting linearly polarized light or a beam of light capable of being filtered to pass linearly polarized light, wherein the light source is configured to be applied with a power of between 30 mW and 1 W and deliver the photoactivating light so that a dose between 5 J/cm$^2$ and 30 J/cm$^2$ can be absorbed by the cornea;

a digital micromirror device (DMD) including a plurality of mirrors arranged in a matrix, the plurality of mirrors configured to selectively reflect the photoactivating light from the light source to provide a pixelated illumination to be directed to a cornea of an eye, the pixelated illumination including pixels defined by the mirrors in the DMD;

one or more optical elements positioned to direct the pixelated illumination from the DMD to the cornea;

a controller configured to control the DMD to programmatically select which of the mirrors reflect the photoactivating light to provide the pixelated illumination to a selected region of the cornea, wherein, at one particular instant in time, the pixelated illumination is defined by a two-dimensional array of the pixels, the controller being configured to control the light source to determine a duration for the pixelated illumination to generate cross-linking activity in the selected region of the cornea; and a feedback system configured to provide the controller with feedback information for controlling the DMD, the feedback system including an eye-tracking system having a video camera, wherein the feedback system is further configured to measure changes in biomechanical strength or stiffness in response to a corneal deflection, and wherein the controller is further configured to determine an amount of cross-linking based on the feedback information, and controlling the light source comprises modulating the DMD spatially and temporally at least partially based on the determination.

3. The system of claim 2, further comprising an applicator configured to apply the cross-linking agent to the cornea, wherein the cross-linking agent includes Riboflavin.

4. The system of claim 2, wherein the light source emits ultraviolet light.

5. The system of claim 2, wherein the one or more optical elements includes an objective lens, and the controller is further configured to generate one or more signals to control a focal plane of the objective lens and thus the depth within the cornea that the pixelated illumination is focused.

6. The system of claim 5, further comprising an objective lens motor configured to adjust the location of the objective lens relative to the mirror array, the controller being configured to adjust the focal plane of the objective lens via the objective lens motor to provide the pixelated illumination in three dimensions to a plurality of different planes between a corneal surface of the cornea and a mid-depth region within the corneal stroma of the cornea.

7. The system of claim 2, wherein each pixel defining the pixelated illumination is associated with a respective one or more mirrors of the DMD.

8. The system of claim 2, wherein the controller is configured to control the DMD to programmatically select which of the mirrors reflect the photoactivating light to direct the pixelated illumination to the selected region of the cornea according to a particular pattern.

9. The system of claim 8, wherein the controller is configured to programmatically control the DMD to modify which of the mirrors reflect the photoactivating light to adjust the pixelated illumination and continue directing the pixelated illumination to the selected region of the cornea according to the particular pattern.

10. The system of claim 9, wherein the eye-tracking system includes a camera configured to provide images indicating the movement of the eye, and the controller is further configured to determine the movement of the eye based on the images.

11. The system of claim 8, wherein the power or the duration for the pixelated illumination determine a dose of photoactivating light to generate cross-linking activity in the selected region of the cornea according to the particular pattern, and the controller is further configured to programmatically modify, during delivery of the dose, which of the mirrors of the DMD reflect the photoactivating light to direct the pixelated illumination to the selected region of the cornea according to the particular pattern.

12. The system of claim 2, wherein the controller is configured to control the DMD to programmatically select any combination of the mirrors to reflect the photoactivating light to provide the pixelated illumination according to a desired pattern.

13. The system of claim 2, wherein the controller is configured to control the DMD to programmatically select the mirrors to reflect the photoactivating light to provide the pixelated illumination according to a non-circular pattern.

14. The system of claim 2, wherein the controller is configured to control at least one of the light source or the one or more optical elements to generate a three-dimensional pattern of the photoactivating light based on the pixelated illumination extending from a surface of the cornea to a depth in a stroma of the cornea.

15. The system of claim 2, further comprising a head restraint device for restraining a head associated with the eye.

16. The system of claim 2, further comprising an interferometer configured to measure a surface shape of the cornea including two quarter-wave plates configured to convert linearly polarized light to circularly polarized light, by receiving a signal beam, the interferometer having a polarizing mask capable of changing following exposure to the signal beam.

17. The system of claim 2, wherein modulating the DMD comprises adjusting the two-dimensional array of the pixels.

*    *    *    *    *